US009396486B2

(12) United States Patent
Stivoric et al.

(10) Patent No.: US 9,396,486 B2
(45) Date of Patent: *Jul. 19, 2016

(54) USING AGGREGATED SENSED DATA OF INDIVIDUALS TO PREDICT THE MENTAL STATE OF AN INDIVIDUAL

(71) Applicant: BodyMedia, Inc., Pittsburgh, PA (US)

(72) Inventors: John M. Stivoric, Pittsburgh, PA (US); Eric Teller, Palo Alto, CA (US); David Andre, San Francisco, CA (US); John A. Monocello, III, Pittsburgh, PA (US)

(73) Assignee: BodyMedia, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/060,072

(22) Filed: Oct. 22, 2013

(65) Prior Publication Data

US 2014/0156698 A1 Jun. 5, 2014

Related U.S. Application Data

(63) Continuation of application No. 12/033,722, filed on Feb. 19, 2008.

(60) Provisional application No. 60/901,952, filed on Feb. 16, 2007.

(51) Int. Cl.
*G06F 17/30* (2006.01)
*G06Q 30/02* (2012.01)
(Continued)

(52) U.S. Cl.
CPC ............ *G06Q 30/0251* (2013.01); *A61B 5/021* (2013.01); *A61B 5/0826* (2013.01);
(Continued)

(58) Field of Classification Search
CPC .................. G06F 17/30002; G06F 17/30017; G06F 17/30286; G06F 17/30292; G06F 19/3431; G06F 19/3437; G06F 19/3443; G06F 19/345; G06F 19/36; G06F 19/10; G06F 19/322; G06F 19/24; G06F 17/30985; G06F 17/30722; G06F 17/30557; G06F 17/30528; G06F 17/30598; G06Q 50/24; G06Q 30/0251; G06Q 30/0242; G06Q 30/0269; G06Q 30/0277; G06Q 30/0271; G09B 19/00; G09B 5/00; G06N 5/04; G06N 99/005; A61B 5/16; A61B 5/6801; A61B 5/7278; A61B 5/6802; A61B 5/72; A61B 5/7475; A61B 5/7275; A61B 5/747; A61B 5/1118; A61B 5/168; A61B 5/4806; A61B 5/4833; A61B 5/4836; A61B 5/742; A61B 5/021; A61B 5/0826; A61B 5/1123; A61B 5/4812; A61B 5/4818; A61B 5/746; A61B 5/04; A61B 5/806
USPC ......... 707/793, 803, 805, 705, 755, 758, 766, 707/802; 705/1.1, 2, 3, 7.29, 7.31; 600/372, 600/386, 387, 388, 389, 390, 301, 384, 509
See application file for complete search history.

(56) References Cited

U.S. PATENT DOCUMENTS 4,052,979 A 10/1977 Scherr et al.
4,129,125 A 12/1978 Lester et al.
(Continued)

*Primary Examiner* — Greta Robinson
(74) *Attorney, Agent, or Firm* — Kokka & Backus, PC

(57) ABSTRACT

The methods and systems described herein may involve determining at least one lifeotype of at least one individual, analyzing the at least one lifeotype, and delivering content to at least one individual based on the analysis. The methods and systems described herein may involve providing a game, determining at least one lifeotype of at least one player of the game, analyzing the at least one lifeotype, and affecting the game play based on the analysis. The methods and systems described herein may involve providing an interactive space, determining at least one lifeotype of at least one individual in the space, analyzing the at least one lifeotype, and modifying at least one attribute of the space based on the analysis.

9 Claims, 36 Drawing Sheets

(51) Int. Cl.

| | | |
|---|---|---|
| *G06Q 40/08* | (2012.01) | |
| *G06Q 50/22* | (2012.01) | |
| *G06Q 50/24* | (2012.01) | |
| *G09B 19/00* | (2006.01) | |
| *A61B 5/16* | (2006.01) | |
| *A61B 5/00* | (2006.01) | |
| *G06F 19/10* | (2011.01) | |
| *G06N 5/04* | (2006.01) | |
| *A61B 5/11* | (2006.01) | |
| *G09B 5/00* | (2006.01) | |
| *A61M 21/02* | (2006.01) | |
| *A61B 5/021* | (2006.01) | |
| *A61B 5/08* | (2006.01) | |
| *G06N 99/00* | (2010.01) | |
| *G06F 19/24* | (2011.01) | |
| *G06F 19/00* | (2011.01) | |
| *A61M 21/00* | (2006.01) | |

(52) U.S. Cl.
CPC .......... *A61B5/1118* (2013.01); *A61B 5/1123* (2013.01); *A61B 5/16* (2013.01); *A61B 5/168* (2013.01); *A61B 5/4806* (2013.01); *A61B 5/4812* (2013.01); *A61B 5/4815* (2013.01); *A61B 5/4818* (2013.01); *A61B 5/4833* (2013.01); *A61B 5/4836* (2013.01); *A61B 5/6801* (2013.01); *A61B 5/6802* (2013.01); *A61B 5/72* (2013.01); *A61B 5/7275* (2013.01); *A61B 5/7278* (2013.01); *A61B 5/7282* (2013.01); *A61B 5/742* (2013.01); *A61B 5/746* (2013.01); *A61B 5/747* (2013.01); *A61B 5/7475* (2013.01); *A61M 21/00* (2013.01); *A61M 21/02* (2013.01); *G06F 17/30528* (2013.01); *G06F 17/30554* (2013.01); *G06F 17/30557* (2013.01); *G06F 17/30598* (2013.01); *G06F 17/30722* (2013.01); *G06F 17/30985* (2013.01); *G06F 19/10* (2013.01); *G06F 19/24* (2013.01); *G06F 19/322* (2013.01); *G06F 19/345* (2013.01); *G06F 19/3443* (2013.01); *G06F 19/36* (2013.01); *G06N 5/04* (2013.01); *G06N 99/005* (2013.01); *G06Q 30/0242* (2013.01); *G06Q 30/0269* (2013.01); *G06Q 30/0271* (2013.01); *G06Q 30/0277* (2013.01); *G06Q 40/08* (2013.01); *G06Q 50/22* (2013.01); *G06Q 50/24* (2013.01); *G09B 5/00* (2013.01); *G09B 19/00* (2013.01); *A61M 2021/005* (2013.01); *A61M 2021/0027* (2013.01); *G06F 19/3431* (2013.01); *G06F 19/3437* (2013.01)

(56) References Cited

U.S. PATENT DOCUMENTS

| | | |
|---|---|---|
| 5,445,149 A | 8/1995 | Rotolo et al. |
| 5,458,123 A | 10/1995 | Unger |
| 5,474,090 A | 12/1995 | Begun et al. |
| 5,476,103 A | 12/1995 | Nahsner |
| 5,484,389 A | 1/1996 | Stark et al. |
| 5,491,651 A | 2/1996 | Janik |
| 5,507,288 A | 4/1996 | Bocker et al. |
| 5,511,553 A | 4/1996 | Segalowitz |
| 5,515,858 A | 5/1996 | Myllymaki |
| 5,515,865 A | 5/1996 | Scanlon |
| 5,523,730 A | 6/1996 | Van Zeeland |
| 5,524,618 A | 6/1996 | Pottgen et al. |
| 5,555,490 A | 9/1996 | Carroll |
| 5,559,497 A | 9/1996 | Hong |
| 5,564,429 A | 10/1996 | Bornn et al. |
| 5,566,679 A | 10/1996 | Herriott |
| 5,581,238 A | 12/1996 | Chang et al. |
| 5,581,492 A | 12/1996 | Janik |
| 5,583,758 A | 12/1996 | McIlroy |
| 5,611,085 A | 3/1997 | Rasmussen |
| 5,617,477 A | 4/1997 | Boyden |
| 5,622,180 A | 4/1997 | Tammi et al. |
| 5,645,068 A | 7/1997 | Mezack et al. |
| 5,663,703 A | 9/1997 | Pearlman et al. |
| 5,666,096 A | 9/1997 | Van Zeeland |
| 5,670,944 A | 9/1997 | Myllymaki |
| 5,673,691 A | 10/1997 | Abrams et al. |
| 5,673,692 A | 10/1997 | Schulze et al. |
| 5,686,516 A | 11/1997 | Tzur |
| 5,687,734 A | 11/1997 | Dempsey et al. |
| 5,697,791 A | 12/1997 | Nashner et al. |
| 5,704,350 A | 1/1998 | Williams, III et al. |
| 5,719,743 A | 2/1998 | Jenkins et al. |
| 6,986,347 B2 * | 1/2006 | Hickle .................. 128/200.24 |
| 7,616,110 B2 * | 11/2009 | Crump et al. ............ 340/539.11 |
| 8,275,635 B2 * | 9/2012 | Stivoric et al. .................... 705/3 |
| 2005/0182659 A1 * | 8/2005 | Huttin ................. 705/2 |
| 2006/0200010 A1 * | 9/2006 | Rosales et al. .............. 600/300 |
| 2006/0218046 A1 * | 9/2006 | Carfi ................... G06Q 30/02 705/26.43 |
| 2007/0112598 A1 * | 5/2007 | Heckerman et al. ............. 705/2 |
| 2008/0051839 A1 * | 2/2008 | Libbus et al. .................... 607/2 |

* cited by examiner

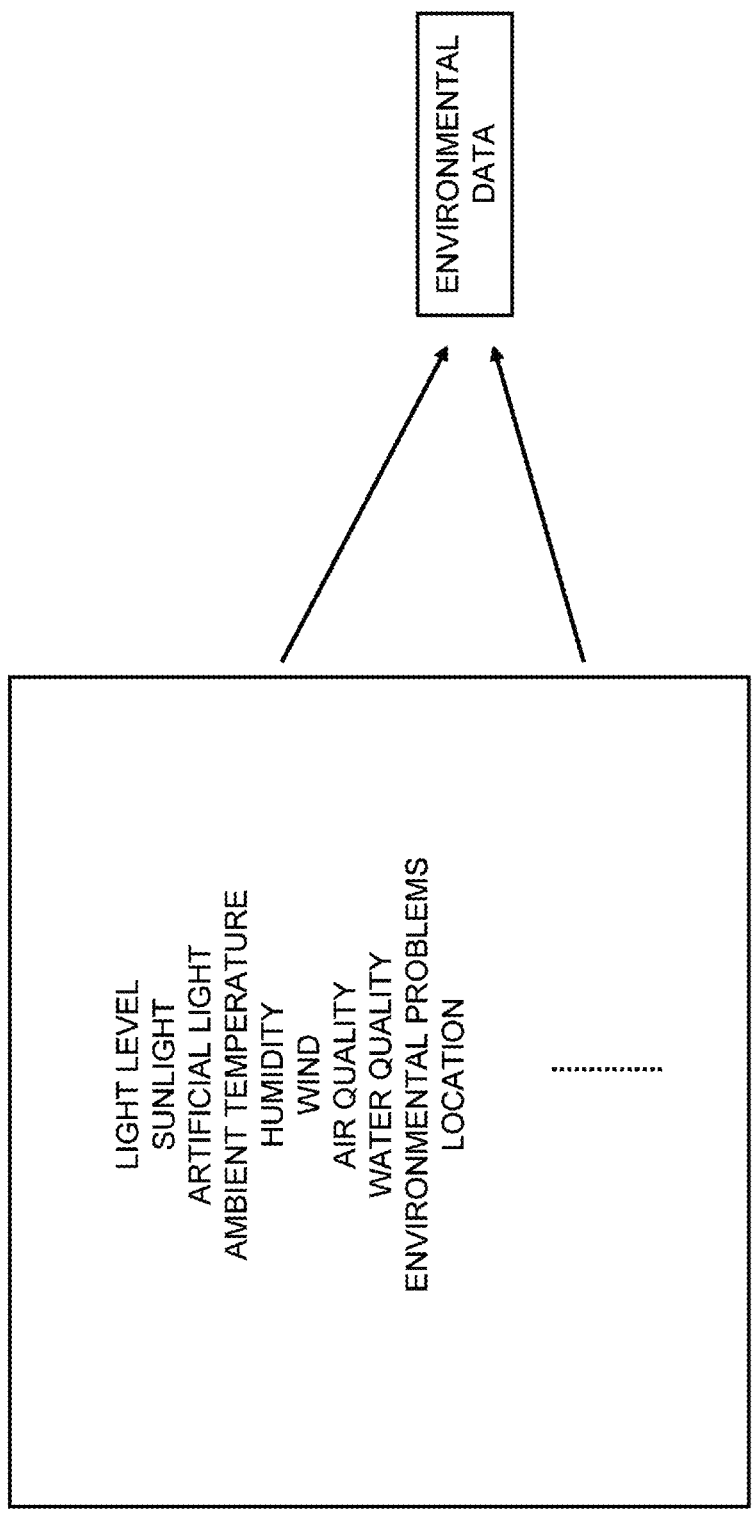

Raw sensed/observed live events are O(x,t), observation of x at time t.

Derived facts or summaries of individual life events are
Q(x,Y,t,t',...) -- some fact derivable from a set of O(x,t)'s, still "about" the time range of the t's.

Patterns of life events. as a person, you typically do X, e.g. p( Q(x,Y,t,t', you, ...) | H),
That is, the probability that some thing is true about you given your history (given your Lifeotype)

Implications of life patterns are P ( some future event | H) , e.g. statements about how H affects your future

Fig. 25

USING AGGREGATED SENSED DATA OF INDIVIDUALS TO PREDICT THE MENTAL STATE OF AN INDIVIDUAL

CROSS-REFERENCE TO RELATED APPLICATIONS

This application is a continuation of U.S. Ser. No. 12/033,722, filed Feb. 19, 2008 which claims the benefit of the following provisional application, which is hereby incorporated by reference in its entirety:

Ser. No. 60/901,952, SYSTEMS AND METHODS FOR UNDERSTANDING AND APPLYING THE PHYSIOLOGICAL AND CONTEXTUAL LIFE PATTERNS OF AN INDIVIDUAL OR SET OF INDIVIDUALS filed Feb. 16, 2007.

BACKGROUND

1. Field

The invention relates to the field of data informatics, and more specifically to systems and methods for analyzing, and parsing information relating to information monitored about subjects, including human lifestyle information.

2. Description of the Related Art

Vast resources have been devoted to the sequencing of the human genetic code and to cataloging the influence of genes and other physiological traits. However, a major component of health and wellness can be attributed to the interactions of subjects with their environment, including their lifestyles. Despite the widely accepted view that lifestyle activities, such as those related to diet, exercise, sleep habits and the like, affect health and wellness, efforts to catalog those effects to date have been limited. A need exists for methods and systems that systematically catalog the effects of various human lifestyles on a wide range of outcomes: that is, a need exists to sequence the human lifestyle. The low cost and ready availability of sensors has reduced costs of collecting data. In addition, improved data integration and processing methods have allowed for use of existing data sources. However, this wealth of data has not yet led to a better overall understanding of the influence of particular lifestyles; instead, the wealth of data has overwhelmed existing systems and methods. A need exists for methods and systems that allow for systematic analysis of lifestyle data.

SUMMARY

The invention may include methods and systems involving assembling data from at least one data source into at least one life bit, assembling the at least one life bit into at least one life byte and analyzing the at least one life byte to determine at least one lifeotype. In one embodiment, each life byte consists of a plurality of life bits, and life bytes are organized into sequences, each of which can be characterized as a life byte sequence. In turn, life byte sequences can be analyzed to identify ones of interest, such as for clinical research, wellness, or the like, such sequences of interest being characterized or expressed as lifeotypes (as described below).

At least one data source rendering a life bit may be a body monitor, such as one that includes one or more sensors. Examples of body monitors and other systems, devices, and methods that can be used to generate the data rendering life bits and ultimately lifeotype data are described in described in Stivoric et al., U.S. Pat. No. 7,020,508, issued Mar. 28, 2006, entitled Apparatus for Detecting Human Physiological and Contextual Information; Teller et al., pending U.S. patent application Ser. No. 09/595,660, for System for Monitoring Health, Wellness and Fitness; Teller, et al., pending U.S. patent application Ser. No. 09/923,181, for System for Monitoring Health, Wellness and Fitness; Teller et al., pending U.S. patent application Ser. No. 10/682,759, for Apparatus for Detecting, Receiving, Deriving and Displaying Human Physiological and Contextual Information; Andre, et al., pending U.S. patent application Ser. No. 10/682,293, for Method and Apparatus for Auto-Journaling of Continuous or Discrete Body States Utilizing Physiological and/or Contextual Parameters; Stivoric, et al., pending U.S. patent application Ser. No. 10/940,889, Stivoric, et al., pending U.S. patent application Ser. No. 10/940,214 for System for Monitoring and Managing Body Weight and Other Physiological Conditions Including Iterative and Personalized Planning, Intervention and Reporting, and Stivoric et al., pending U.S. patent application Ser. No. 11/582,896 for Devices and Systems for Contextual and Physiological-Based Detection, Monitoring, Reporting, Entertainment, and Control of Other Devices, each of which are incorporated, in their entirety, herein by reference.

The data may include physiological data, contextual data and environmental data. The data may also include derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data.

In an embodiment, at least one of the assembly and analysis of lifotypes may utilize a wide range of techniques applied to a life byte sequence, a life byte, a life bit, or a lifeotype, in order to yield a prediction, inference, or the like. Such techniques may include, without limitation, iterative optimization, genetic programming, stochastic simulations, model generation, model use, simulated annealing, Markov methods, reinforcement learning, partial programming, stochastic beam search, model based search, goal-based search, goal-based methods, feedback loops and artificial intelligence. In embodiments, the method may be applied to medical decision making, disease management, auto-publishing, automatic completion of forms, filtering search results, delivering content, dating, social networking and e-commerce. In embodiments, the at least one lifeotype and any related information may be represented in a spider map or the like or may be superimposed on a map. In embodiments, the method may further comprise determining the numbers and types of life bits and life bytes required to fully determine a lifeotype.

The methods and systems disclosed herein may include a method or system involving classifying data concerning a population of individuals into lifeotypes that correspond to certain combinations of aspects of at least one of the human lifestyle, human status and the human condition, such combinations optionally including combinations of life bytes, life byte sequences, life bits, or combinations of other lifeotypes. In an embodiment, the method or system may also involve analyzing patterns within and across lifeotypes to draw conclusions, draw inferences, or make predictions about individuals with a certain lifeotype or groups of individuals that share a certain lifeotype. At least one data source may be a body monitor including at least one sensor. The data may include any of the data sources described herein or in documents incorporated by reference herein, including, for example, physiological data, contextual data and environmental data. The data may also include derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data.

The classification process used to identify a lifeotype may utilize a wide range of techniques disclosed herein, in the documents incorporated by reference herein, or known to those of ordinary skill in the art, including, without limitation iterative optimization, genetic programming, stochastic simulations, model generation, model use, simulated annealing, Markov methods, reinforcement learning, partial programming, stochastic beam search, model based search, goal-based search, goal-based methods, feedback loops and artificial intelligence. In embodiments, the method or system may be applied to medical decision making, disease management, auto-publishing, automatic completion of forms, filtering search results, delivering content, dating, social networking and e-commerce. In embodiments, the at least one lifeotype and any related information may be represented in a spider map or the like or may be superimposed on a map. In one embodiment, the more than one life byte may be organized into a life byte sequence.

The methods and/or systems disclosed herein may include a system containing a facility for assembling data from at least one data source into at least one life bit, a facility for assembling the at least one life bit into at least one life byte, and a facility for analyzing the at least one life byte, or a sequence of life bytes, to determine at least one lifeotype. At least one data source rendering a life bit may be a body monitor, such as including one or more sensors. The data may include physiological data, contextual data and environmental data. The data may also include derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data.

In an embodiment, at least one of the facility for assembly and the facility for analysis of lifotypes may utilize a wide range of techniques applied to a life byte sequence, a life byte, a life bit, or a lifeotype, in order to yield a prediction, inference, or the like. Such techniques may include, without limitation, iterative optimization, genetic programming, stochastic simulations, model generation, model use, simulated annealing, Markov methods, reinforcement learning, partial programming, stochastic beam search, model based search, goal-based search, goal-based methods, feedback loops and artificial intelligence. In embodiments, the system may be applied to medical decision making, disease management, auto-publishing, automatic completion of forms, filtering search results, delivering content, dating, social networking and e-commerce. In embodiments, the at least one lifeotype and any related information may be represented in a spider map or the like or may be superimposed on a map. The system may also include a facility for determining the numbers and types of life bits and life bytes required to fully determine a lifeotype.

The methods and systems disclosed herein may include a system with a facility for classifying data concerning a population of individuals into lifeotypes that correspond to certain combinations of aspects of at least one of the human lifestyle, human status and the human condition, such combinations optionally including combinations of life bytes, life byte sequences, life bits, or combinations of other lifeotypes. In an embodiment, the system may also involve analyzing patterns within and across lifeotypes to draw conclusions, draw inferences, or make predictions about individuals with a certain lifeotype or groups of individuals that share a certain lifeotype. At least one data source may be a body monitor including at least one sensor. The data may include any of the data sources described herein or in documents incorporated by reference herein, including, for example, physiological data, contextual data and environmental data. The data may also include derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data. The data may data related to family history, genes, diagnoses, medical knowledge, polygraphs and the like. The data may be collected over time. The data may be data relevant to a certain measure at various points in time.

The facility for classifying data may utilize a wide range of techniques disclosed herein, in the documents incorporated by reference herein, or known to those of ordinary skill in the art, including, without limitation iterative optimization, genetic programming, stochastic simulations, model generation, model use, simulated annealing, Markov methods, reinforcement learning, partial programming, stochastic beam search, model based search, goal-based search, goal-based methods, feedback loops and artificial intelligence. In embodiments, the system may be applied to medical decision making, disease management, auto-publishing, automatic completion of forms, filtering search results, delivering content, dating, social networking and e-commerce. In embodiments, the at least one lifeotype and any related information may be represented in a spider map or the like or may be superimposed on a map. In one embodiment, the more than one life byte may be organized into a life byte sequence.

The methods and systems described herein may involve determining at least one lifeotype of at least one individual, analyzing the at least one lifeotype, and delivering content to at least one individual based on the analysis. In embodiments, the content may consist of video, audio, images, text, advertisements, movies, music, music videos, games, ring tones, print media, books, art, fine art and user generated content. In embodiments, the content may be from an Internet site and may be delivered to an individual based on a lifeotype of the individual or the content is from an Internet site and may be recommended for delivery to an individual based on a lifeotype of the individual.

In embodiments, the content may be tagged and the tags may facilitate delivery of the content based on at least one lifeotype. In embodiments, the analysis may include consideration of recommendations by at least one other individual with at least one similar lifeotype as the individual to which the content is to be delivered. In embodiments, the version of the content to be delivered may be determined based on the analysis. In embodiments, the less stressful of two versions of content may be selected for delivery based on the analysis. In embodiments, the analysis may consider data from a device worn by the at least one individual or data from a device carried in proximity to the at least one individual.

The methods and systems described herein may involve providing a game, determining at least one lifeotype of at least one player of the game, analyzing the at least one lifeotype, and affecting the game play based on the analysis. In embodiments, at least one lifeotype of a player of the game may affect the abilities of the player's character in the game based on the analysis or the outcome of the game based on the analysis. In embodiments, a lifeotype of an individual associated with a healthy state may enable a higher performing character in the game than the character that would be enabled by a less healthy lifeotype. In embodiments, the game may be an online game, a multiplayer game or a massively multiplayer game. In embodiments, the methods and systems may further comprise providing feedback to the at least one player to affect changes in the player's lifeotype. In embodiments, the game play experience of the user may be customized based on the lifeotype of the user. In embodiments, the analysis may consider data from a device worn by the at least one player or data from a device carried in proximity to the at least one player.

The methods and systems described herein may involve providing an interactive space, determining at least one lifeotype of at least one individual in the space, analyzing the at least one lifeotype, and modifying at least one attribute of the space based on the analysis. In an embodiment, the space may be a meeting room, an auditorium, an interactive gaming environment or an interactive entertainment environment. In embodiments, the attribute of the space that is modified may be selected from the group consisting of: brightness, color, volume, sound, audio, temperature, air quality, pressure, distance between objects, protection from outside, status of entries, status of exits, status of a device, presence of objects and absence of objects. In embodiment, the analysis may consider the proximity of various lifeotypes, changes in various lifeotypes, the compatibility of various lifeotypes, data from a device worn by the at least one individual or data from a device carried in proximity to the at least one individual. In embodiments, the systems and methods may further include providing feedback to the at least one individual.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures:

FIG. 11 depicts the types of data that may comprise environmental data.
FIG. 18 depicts a lifeotype spider map or the like.
FIG. 25 depicts a particular embodiment of a statistical model concerning lifeotypes.

DETAILED DESCRIPTION OF THE PRESENTLY PREFERRED EMBODIMENT

Figure 1:
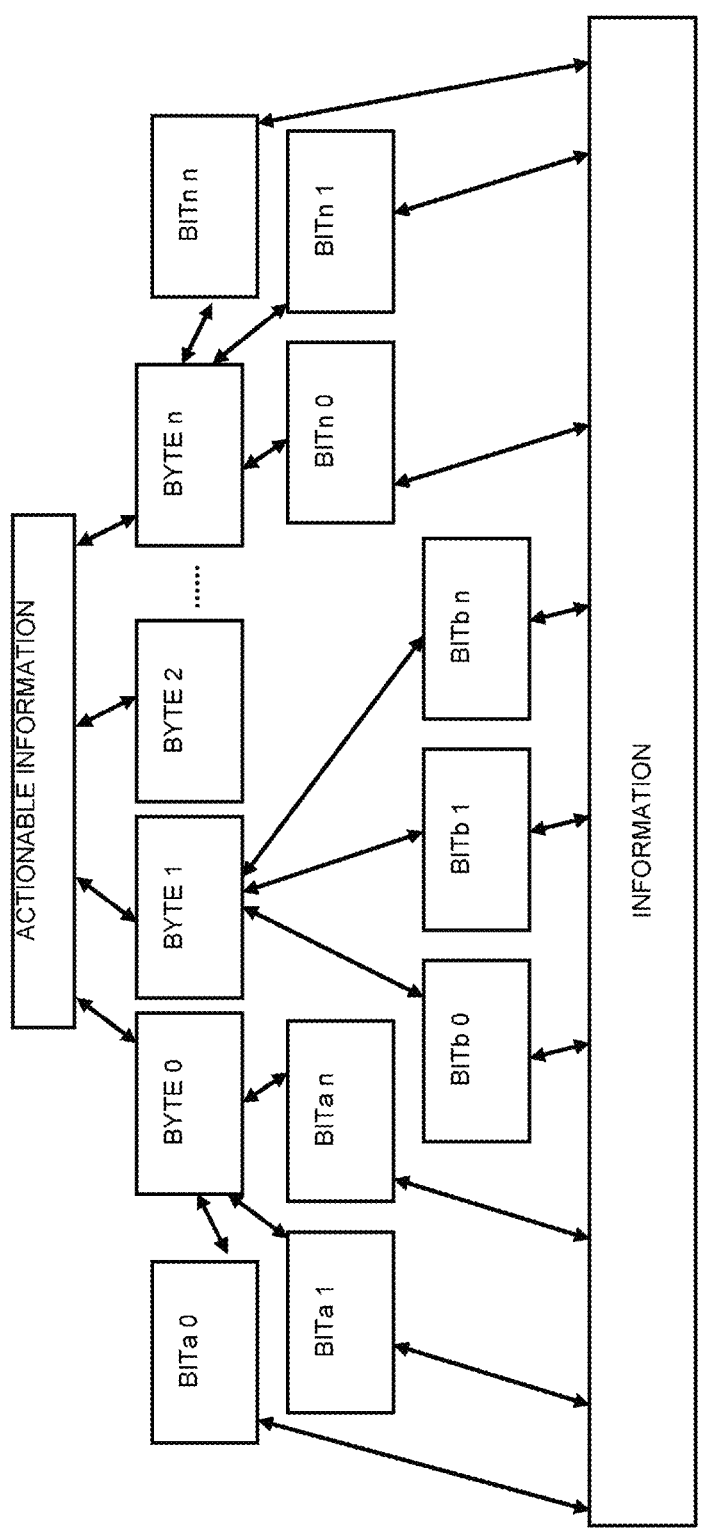
FIG. 1 depicts a hierarchy of data.

Humankind has sequenced the human genetic code, resulting in the identification of sequences of genes that are related to particular conditions, outcomes or the like. Thus, a certain genotype can be associated with outcomes, allowing the prediction of outcomes for individuals or groups that share that genotype. However, despite a wealth of information collected about lifestyles, similar efforts have not been undertaken to sequence data related to the human lifestyle in order to allow the drawing of the same kinds of inferences about individuals or groups that share the same lifestyle. The low cost and ready availability of sensors has reduced costs of collecting data. In addition, improved data integration and processing methods have allowed for use of existing data sources. The availability of this wealth of data creates a unique opportunity for data analytics and data processing, which may be used to analyze and parse the wealth of human lifestyle information. Importantly, methods and systems are disclosed herein for organizing data about lifestyles into meaningful sequences of information, allowing analysis and drawing of inferences about the effects of human lifestyles. Among other advantages, data processing and data analytics, applied to life bits, life bytes, life byte sequences and lifotypes, may also allow for the creation or identification of new surrogate measures, sensors and vital signs, as well as predictors of certain conditions.

Thus, the concept of a "lifeotype" encompasses classifying human state data, or other data concerning a population or sub-population of individuals, into "types" that correspond to certain combinations of traits or aspects of human lifestyle, human status and/or human condition. In embodiments, the concept of a lifeotype may also be applied to other organisms. By analyzing patterns within and across the lifeotypes, one can draw conclusions, make inferences, and make predictions about each type that apply to the members of the type or to groups of individuals of that type. The possible types may be composed of combinations of individual data types which may be measured continuously over time or at discrete intervals.

Referring to FIG. 1, the concept of a lifeotype may be further understood by analogy to bits and bytes of information in the data world. Information may be organized into bits, bits may be organized into bytes, bytes may be organized into sequences, and any of the foregoing may be organized into, or provide, actionable information. Actionable information may be composed of any number, including none, of bits and/or bytes. The inclusion of bit 0 and byte 0 in FIG. 1 illustrates that it is possible that there are no bits and/or bytes in a particular embodiment. That is, it is possible that the information itself is a byte or that a bit is actionable information, that the information itself is actionable and the like.

By analogy to the bits and bytes of FIG. 1, a life bit may be a bit of data for a trait or aspect at a point in time. A life byte may be a collection of life bits. In an embodiment, the bits may be values of certain parameters, with bits of certain types (such as derived from certain data sources, including the ones described herein) being arranged in a predetermined way to form a byte. The byte may be an aggregate of the bits, which may for example, correspond to a particular type of information, such as a type of file, a message, a command, or the like, in the same way that a particular type of life byte may correspond to a particular type of information collected about a human state. The bytes may be sequenced or otherwise combined to form actionable information, such that a higher level system, such as an operating system, application, program, service or the like can take a byte or series of bytes and perform an operation based on the nature of the byte or sequence of bytes and in particular the bits that populate that byte.

Figure 2:
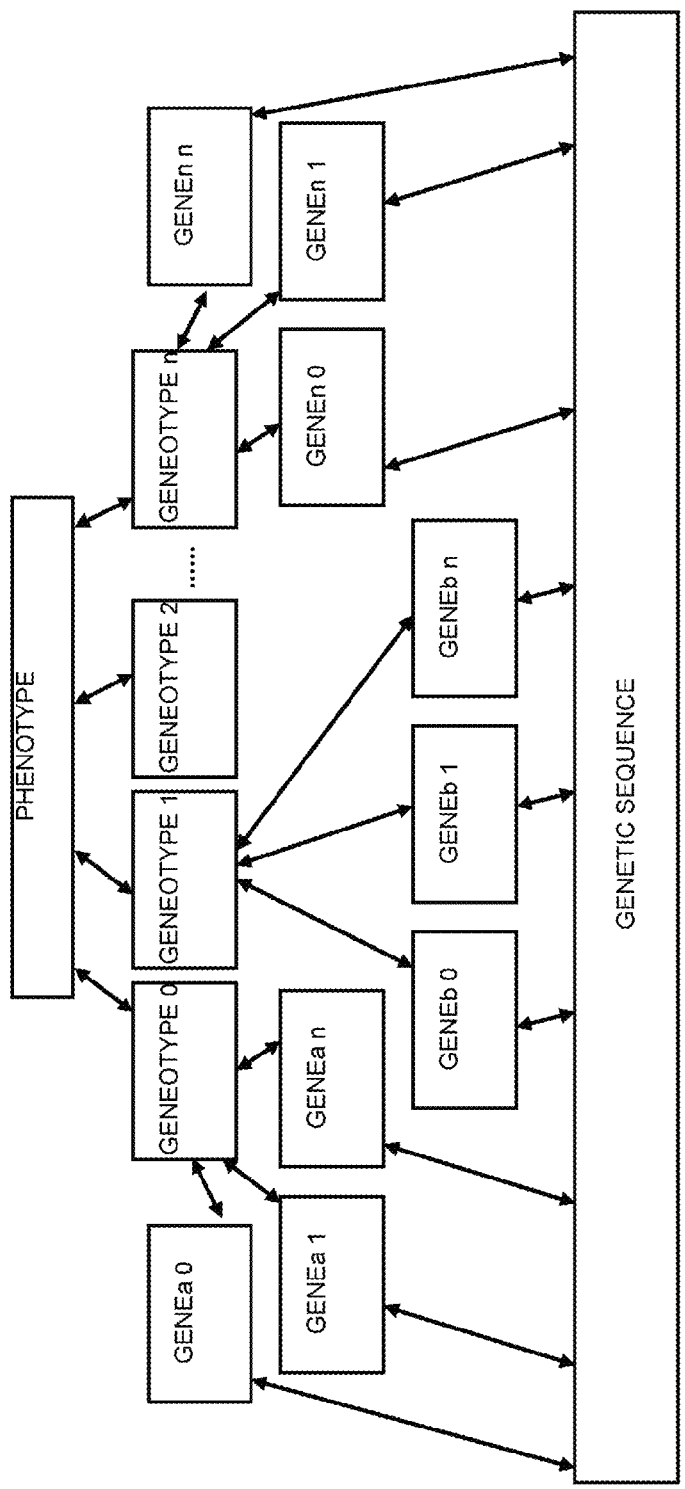
FIG. 2 depicts a hierarchy of genetics data.

Referring to FIG. 2, the concept of a lifeotype may be further understood by analogy to genetics. Genetic information may be organized in base pairs or genetic sequences and in their totality comprise the genotype. Life bits can be thought of as analogous to genes, which are organized according to the sequence of the genotype, but may or may not be expressed in a given individual, or may be expressed to a different extent in a particular individual. Particular genes or sequences of genes that are expressed (including, in some cases, expressed to a particular extent) and that, taken together, are of interest, may be assembled into genotypes, in the same way that life bytes or sequences of life bytes that are of interest may be assembled into lifeotypes. The genotypes in turn, through the interaction with the environment in some cases, may present as an overall phenotype, analogous to actionable information. As with FIG. 1, the inclusion of the subscript zeros in FIG. 2 indicates that a particular level of the hierarchy may be absent in certain embodiments.

Figure 3:
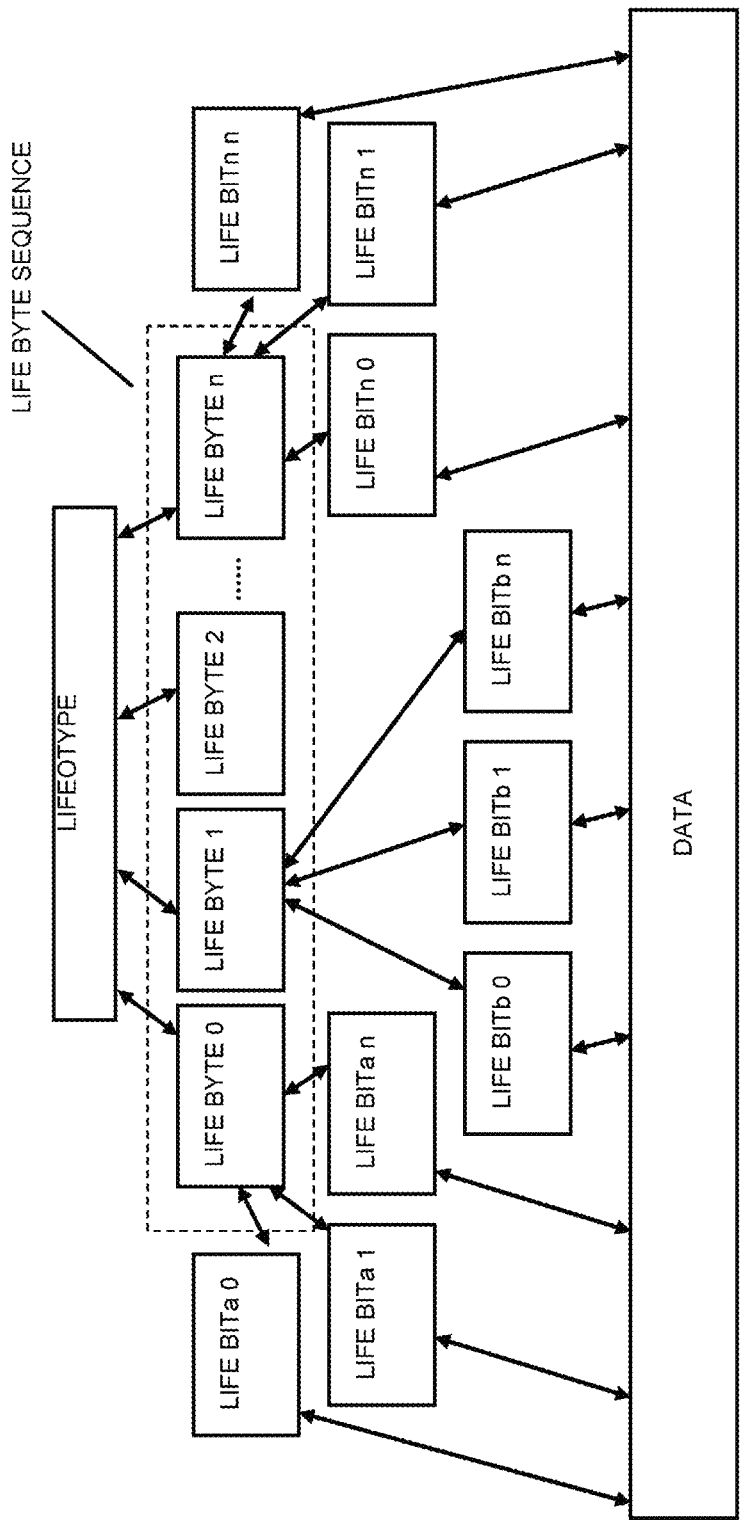
FIG. 3 depicts a hierarchy of lifeotype data.

FIG. 3 depicts the organization structure of FIGS. 1 and 2 applied to lifeotypes. Referring to FIG. 3, the information or genetic sequences may be data, such as any of the data described herein, from any of the sources described herein. The data may be combined, used or accessed to create life bits. The life bits may be combined, used or accessed to create life bytes. A grouping or sequence of lifebytes may form a lifebyte sequence. Lifebytes and/or one or more lifebyte sequences may comprise or be organized into lifeotypes. The amount of information, number of life bits and/or number of life bytes included in a lifeotype may be determined based on many factors, such as user selection or the number of data points required to obtain uniqueness. As in FIGS. 1 and 2, the inclusion of the subscript zeros indicates that a particular level of the hierarchy may be absent in certain embodiments.

The entire range of data collected about an individual may be analogous to the entire genotype of an individual, and particular combinations in the data patterns may be analogous to genes or collections of genes that code for particular traits. As with a particular genotype, a particular lifeotype may code for or represent a particular set of traits. A lifeotype may change over time, including reasons such random change reasons due to therapy, such as behavior modification therapy, reasons due to other changes in an individual's behavior, how the individual interacts with his environment and vice-verse, and due to modifications, or additions to the amount and type of information being collected about an individual. This process may be analogous to gene mutations and gene therapy in genetics. Regarding therapeutics, the therapeutics process may be intentional or non-intentional and/or prescribed or self-administered. The pool of data may be less than the total pool of data, which may be analogous to sequencing less than all of the genetic code of an individual in genetics. Referring again to FIGS. 1, 2 and 3, it may be possible to move in both directions in the hierarchies depicted in the figures. For example, in FIG. 3, the data or life bits may be determined from a life byte or lifeotype. In FIG. 1, it may be possible to work from actionable information back to information.

In an embodiment, a life bit may be body positional data, such as sitting or standing. A related life byte may be standing more than sitting. This life byte may contribute to the determination of a lifeotype which may be characterized as one relating to the condition of varicose veins. In another embodiment, the data may include financial and transaction data. The related life bits may include certain transactions and financial data. These life bits may be aggregated into a financial status life byte.

In another embodiment, a particular lifeotype may be that of a depressive. The data on which this lifeotype is based may include survey data, financial data, transaction data, medical data and sensor data. Sensors, such as the type described in United States patent applications incorporated herein by reference provide sensed data from which a derivation could be made regarding an individual's activity level, food intake, mood, and interaction with others. All of such sensed data in each patent application incorporated herein by reference is relevant to this and all other embodiments described herein. A relevant life bit may be composed of credit card purchases, and a relevant life byte may reveal that the majority of purchases were online and few were at point of sale terminals, thus revealing that the individual tends to stay in one location. The survey data may result in a life byte that indicates the individual is depressed. The sensor data may show that the individual spends most of his time in one location due to low levels of activity, and that the individual has limited interaction with others. These factors together may be a lifeotype or marker for a depression, analogous to a genetic marker or the genotype of an individual that is depressed.

In another embodiment, a lifeotype may be a hypertensive, diabetic runner. The data on which this lifeotype is based may include survey data, medical data and sensor data. Certain of the relevant life bytes may include age related information, bone density related information and a diabetic life byte. The values of these life bytes may indicate a high likelihood of hypertension and low bone density. The Platform may suggest additional data that should be collected for further investigation. A sensor may provide many activity life bits, which may indicate an overall active life byte. The Platform may sequence the life bytes to find the lifeotype to be a runner with low bone density, hypertension and diabetes.

In another embodiment, a particular lifeotype may be that of an active diabetic. This lifeotype may be a 4 byte lifeotype, where life byte 1 is a glucose reading, life byte 2 is a pancreas function measurement of some kind, life byte 3 is total calories consumed in a day and life byte 4 is total calories burned in exercise. Each byte may be composed of several life bits. In an embodiment, total calories burned may be determined from life bits including activity level data as determined by sensor data and food intake data as determined from a survey or any of the systems, devices or methods described in the patent application which are incorporated herein by reference. Certain of the life bytes may originate directly from the data, such as glucose readings determined directly from a glucose meter. The resulting life bits and life bytes may be packaged into their own data structures, such as a packet header In an embodiment, a lifeotype may be a pattern of behavior and sensed values that indicates that an individual is at a very high risk of becoming diabetic later in life. In an embodiment, the lifeotype may be defined by four lifebytes. The first life byte may be composed of sensed health data life bits such as yearly blood pressure readings administered at a doctor's office and extracted from the individual's electronic medical record or personal health record. The second life byte may be residence data revealing that the individual lives in an urban area that is not conducive to year-round exercise and that is characterized by very long commute times. The third life byte may consist of data from a medical record and may indicate that the individual is Mexican-American and that two of the individual's four grandparents were diabetic before they died. The fourth life byte may consist of survey data and may indicate that the individual exercises very vigorously, but only occasionally with a frequency of 1.2 times per week and only for average of 75 minutes each time. In an alternative embodiment, a life byte may be that an individual is at a very high risk of becoming diabetic later in life and the life bits may be sensed health data, residence data, medical record data and survey data. In another embodiment, the lifeotype may be related to diabetes, hemorrhagic shock or hypertension. The data bits may related to genetic markers, diagnoses, plans for therapy, sensed data regarding physical activity, such as from a wearable device, energy expenditure, nutritional data and the like.

A genotype may be conceived of as an encoding of what may happen to a person through the process of developmental biology, similar to a blueprint for a house. This genetic blueprint may also be thought of as the gold-standard for the house, the platonic house, or the default house, based on all of which variation will occur. The genotype may also set the basic rules for how that physical body will function in response to particular kinds of changes to that body. By analogy, this may be like the house having a built in furnace and thermostat and being set to turn on the heat when the thermostat drops below a particular temperature.

A genotype may have various levels of abstractions that are useful to understand about the way that encoding (that blueprint) is translated into a physical system or the basic rules of operation of that physical system. A genotype in a human is made up of atoms, but that is often too fine grained a level of detail and is not usually considered a useful way to talk about the genotype. The lowest level of abstraction normally used for a genotype are the base pairs that make it up ("A T C and G").

The state of your body at some point in the future may not entirely be determined by its genetic make up. Genetics may have, over time, only a minority impact on the state of a person's body. The other relevant elements may be the things that happen to a body. A simple illustrative example is as follows: if a car side-swipes a person and breaks the person's leg, the body has changed dramatically and not because of genetics (although genetics may affect the extent of the break, the time to heal and the like). Similarly, if a person eats too much over a long period of time and becomes obese, this was not a fact solely related to the person's blue print (genotype) but of the complex web of cause and effect interactions that the person has with the world as the person lives his life (although genetics may affect that person's interaction with the world, such as by determining at least in part the effects that food has on the person's body). In one particular embodiment, this data collected about a person that corresponds to the series of things that happens to a person or because of a person's choices which determines to a large extent what will happen to a person in the future can be thought of as a lifeotype. In certain embodiments, a lifeotype may also include or be based on genetics-related information (as bits, bytes, life byte sequences, etc.), as well as any of the other information discussed herein.

Figure 24A:
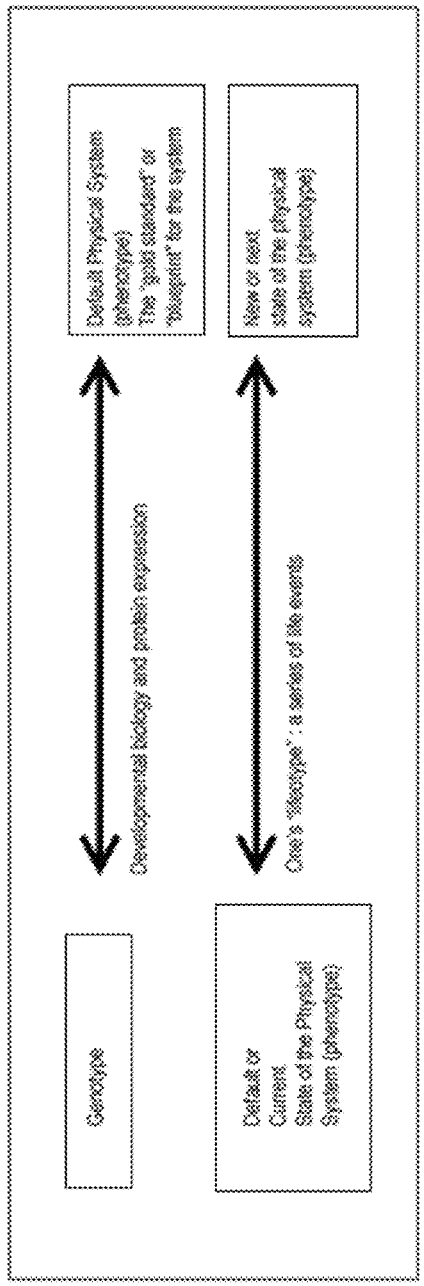
FIGS. 24A and 24B depict a particular embodiment of an analogy between a lifeotype and genetics.
Figure 24B:
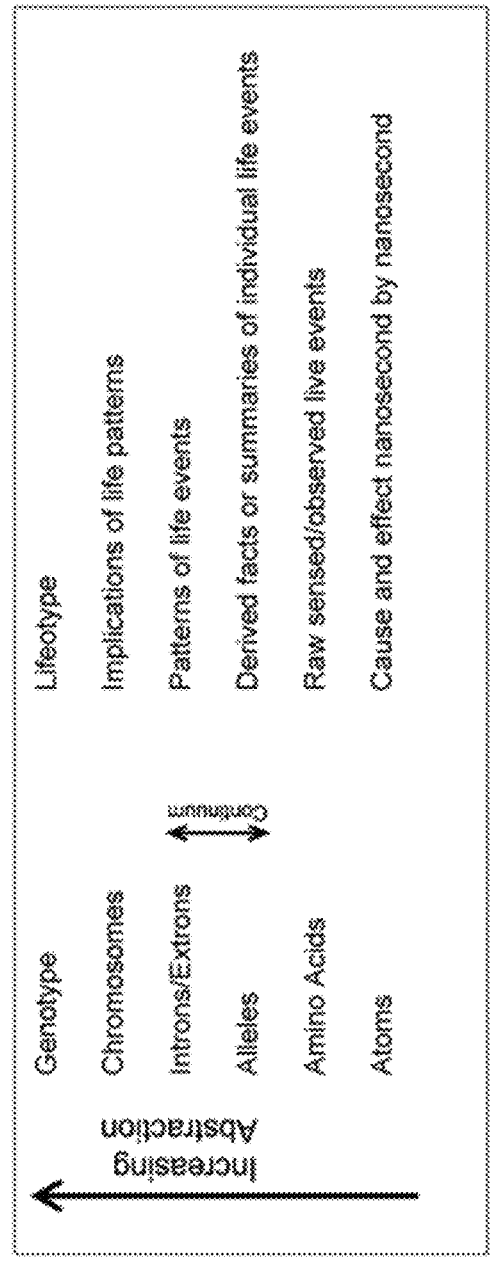

Referring to FIGS. 24A-24B, in one particular embodiment, like the human genotype, the human lifeotype may have various levels of abstraction. In this particular embodiment, at the lowest level (the equivalent to the base pairs), are all the facts of what happened to a person expressed in their raw "sensed" values. An example is as follows: each key stroke that a person made at his/her computer, each acceleration a person's body experiences as it moves about daily life, a person's heart rate at each minute of the day, and the like. In this particular embodiment, the equivalent to the alleles and their relative importance (intron vs. extron) may be the notion of a continuum from "derived data" through "patterns of data." So for example, thinking about many of the sensed values about a person's body not in isolation but taken together in a model of energy expended may be a "derived" lifeotype fact in this particular embodiment. In this particular embodiment, at a higher level of derivation or pattern finding might be that over a period of time energy expenditure is high enough to qualify as an "active person." And, in this particular embodiment, up at the level, by analogy, of a chromosome for a lifeotype may be the notion of the implication of major patterns of the data of your life upon the future state of your body. For example, being an active person makes obesity, diabetes, depression, and heart disease all some what less likely to occur to you. In this particular embodiment, just like gene therapy is an attempt to improve a person's body in the future by changing some of the genetic blue print, an individual could also receive a suggested change to his lifeotype that would tend to improve his body's future state as well. For example, "a person may not be an active person and if he was to exercise an additional 60 minutes per week, raising him into the state of being an active person, he is less likely to develop the following diseases within the next two decades . . . " This type of suggested action may be an action type, or A-type. FIG. 25 depicts a particular embodiment of a statistical model involving lifeotypes. In this embodiment, conditional probabilities may be determined based on lifeotypes. One skilled in the art will appreciate that the analogies described herein are for illustrative purposes and should not serve to limit the meaning of terms described herein. None of the usages of the terms in the analogies or examples herein are intended to contradict the meaning of any term in this disclosure, but rather as alternate meanings or nuanced meanings of the terms.

Figure 4:
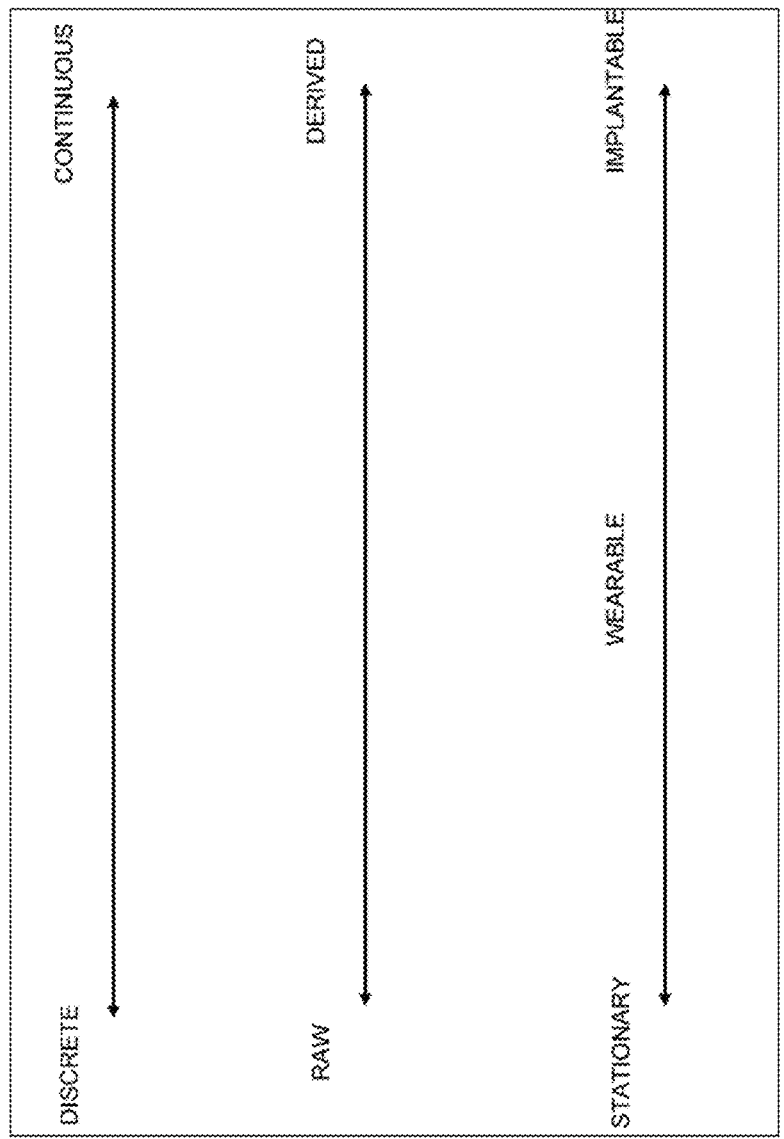
FIG. 4 depicts certain spectra of certain lifeotype data sources.
Figure 5:
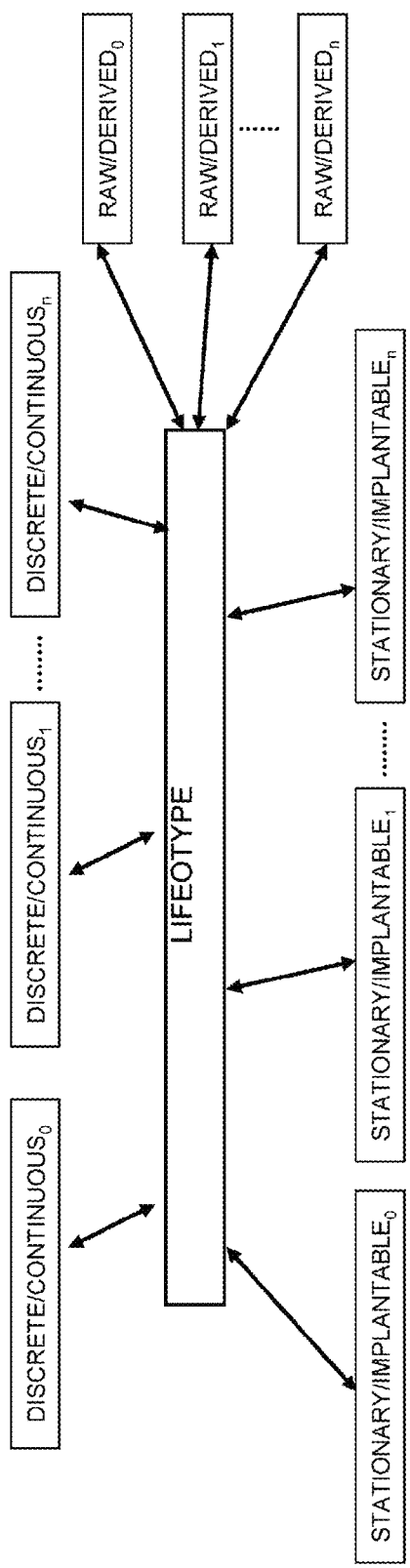
FIG. 5 depicts lifeotype data sources.

Referring to FIG. 4, the data may include continuous or discrete data or any form of data that may be found along this spectrum. In an embodiment, the data may be continuous temperature data and/or a discrete measure such as a voltage. The data may include raw or derived data or any form of data that may be found along this spectrum. The raw data may be unprocessed. The derived data may be derived from the raw data, other derived data or a combination of both. The data may be sensed by a body monitor and/or a sensor, which may be stationary, wearable or implantable, or any form that may be found along this spectrum. A stationary sensor may be housed in an item of fitness equipment, such as a treadmill. A wearable sensor may be included as part of an arm band, shirt or shoe. In an embodiment, an implantable sensor may be a heart rate sensor implanted near the heart. Referring to FIG. 5, a lifeotype may or may not be constructed from at least one item of discrete or continuous data, raw or derived data and/or data sensed by a body monitor and/or sensor which may be stationary, wearable or implantable. The inclusion of the subscript zeros in FIG. 5 indicates that a particular level of the hierarchy may be absent in certain embodiments.

A lifeotype may be static or dynamic or may exist in a form found along this spectrum. That is, a lifeotype may consist of data that is more static over time or data that is more dynamic over time. A lifeotype may be high resolution or low resolution or may exist in a form along this spectrum. That is, a lifeotype may consist of a variety of life bytes, life bits and data, which would make it a lifeotype of a higher resolution when compared to a lifeotype that is based on relatively few life bytes, life bits and data instances. A static lifeotype and a high resolution lifeotype may respond in similar ways to changes in the data on which each is based. This behavior similarity may be due to a greater number and variety of life bytes, life bits and data instances being involved, so it requires a greater change in the underlying factors and data to produce a change at the lifeotype level. A dynamic lifeotype and a low resolution lifeotype may respond in similar ways to changes in the data on which each is based. This behavior similarity may be due to a lower number and low variety of life bytes, life bits and data instances being involved, so it requires only a change in one or a few values of the underlying factors and data to produce a change at the lifeotype level. In embodiments, a low resolution and/or dynamic lifeotypes, or the life byte sequences, life bytes, life bits and/or data upon which they are based, may include angry, aroused, tired, fatigued, current spending, location, restless, stressed and the like. In embodiments, a high resolution and/or static lifeotypes, or the life byte sequences, life bytes, life bits and/or data upon which they are based, may include depressed, addict, diabetic (type I and II), insomniac, cardiac condition and the like. In certain embodiments a high resolution lifeotype may change rapidly over time and a low resolution lifeotype may change more slowly over time. Lifeotypes can be true or representative at specific points or ranges of time in a person's life. Lifeotypes may reflect different time scales.

The Platform may be able to determine and/or display the direction of a lifeotype. In this way, the direction of trend of a lifeotype and/or group of lifeotypes can be determined. This information may be useful for identifying and/or predicting changes in high resolution and/or static lifeotypes. In an embodiment, due to the possibly variable nature of a low resolution and/or dynamic lifeotypes, such lifeotypes may be conceived of or reported with a tolerance band based on related trend information and predictions. In another embodiment, the trend information and predictions may be useful in predicting emergencies in connection with low resolution and/or dynamic lifeotypes and disease states in connection with high resolution and/or static lifeotypes. Lifeotype trend information, including trend directions, may be useful for treating certain conditions for which certain parameters need to be kept in a certain range. In an embodiment, certain lifeotypes of bipolar individuals may need to be kept within a certain range for a certain parameter, such as mood or endorphin levels. Using the trend direction functionality it may be possible to affect the trend as the lifeotype value approaches the boundary of the range.

A system for creating, analyzing and making use of lifeotypes may contain various layers, facilities and/or functionalities (the "Platform").

Figure 6:
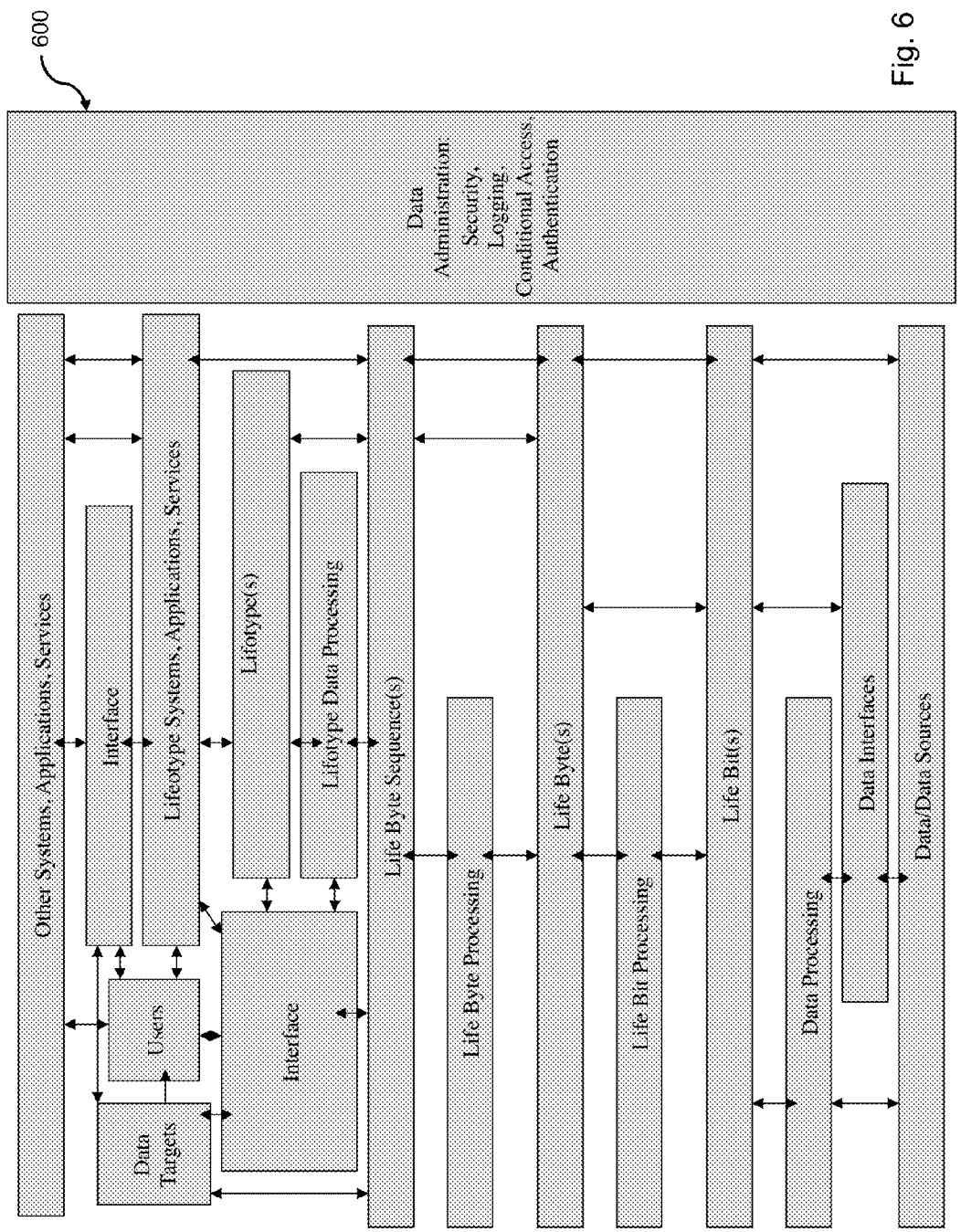
FIG. 6 depicts the Platform.

FIG. 6 depicts one particular embodiment of the Platform. The various layers, facilities and/or functionalities may appear in an order or arrangement different from that shown in FIG. 6. Referring to FIG. 6, the Platform may contain data and/or data sources, a data interface, data processing, life bits, life bit processing, life bytes, life byte processing, life byte sequences, lifeotype data processing, interfaces, lifeotypes, lifeotype systems, applications and/or services, users, data targets, other systems applications and/or services and data administration, including security, logging, conditional access and/or authentication.

The data and/or data sources may be any of the data described herein or may be from any of the sources described herein. The data and/or data sources may include data from sensors, user input and/or other sources as described herein. The data and/or data sources may include physiological data, contextual data and/or environmental data as described herein.

The data interfaces layer may contain adaptors and/or connectors which allow the Platform to communicate with various disparate data sources. In an embodiment, a connector may permit the Platform to obtain patient data from a particular hospital database, such as a patient admission database. The data interfaces layer may be or contain an interface to sources and targets. The data interfaces layer may be based on a push model, pull model or both. The data interfaces layer may include search/filter/cluster functionality.

The data processing layer may enable analytics and derivation. The data processing layer may create, generate, identify and/or discover lifebits. The data processing layer may search for patterns in the data to create lifebits. The data processing layer may mine data. The data processing layer may identify missing information, which may assist in the creation, generation, identification and/or discovery of life bits. In an embodiment, the data processing layer may identify a life bit the knowledge of which may be germane to a particular purpose and may also identify the data that is required to be collected in order to determine that life bit. The data processing layer may analyze life bits and related data. The data processing layer may generate conclusions, predictions and/or recommendations. The data processing layer may identify patterns in the life bits. The data processing layer may sequence the life bits.

The data processing layer may generate reports. The data processing layer may auto-publish information, such as reports and studies. The data processing layer may auto-complete forms, such as medical records and insurance forms. The data processing layer may process, organize and manage life bits. The data processing layer may clean and de-duplicate life bits data. The data processing layer may perform extractions, transformations and loads of the life bits data. The data processing layer may convert life bits data to a common format. The data processing layer may aggregate, combine and collect life bits data. The data processing layer may request missing data. The data processing layer may create databases and datamarts of life bits data and/or other data. The data processing layer may associate metadata with the life bits data.

The data processing layer may filter and/or apply contextual structures to life bits data. The data processing layer may apply algorithms to life bits data. The data processing layer may enable annotation of, or may auto-annotate, life bits data. The data processing layer may be based on a push model, pull model or both. The data processing layer may process and/or clean data. The data processing layer may allow data from multiple sources to be combined. The data processing layer may organize and manage data. The data processing layer may enable storage and/or retrieval of data. The data processing layer may enable storage and retrieval of information based on or derived from the data. The data processing layer may store and/or retrieve metadata. The data processing layer may read and/or write data and metadata. The data processing layer may enable versioning and/or partitioning. The data processing layer may predict future life bits. The data processing layer may compare a set of life bits to the genotype and determine the degree of presence of other life bits.

Life bit(s), as described herein, may be determined directly from the data, from a data interface and/or through data processing. A life bit processing layer may enable analytics and derivation. The life bit processing layer may create, generate, identify and/or discover life bytes. The life bit processing layer may search for and identify patterns in the data to create life bytes. The life bit processing layer may mine data. The life bit processing layer may identify missing information, which may assist in the creation, generation, identification and/or discovery of life bytes. In an embodiment, the life bit processing layer may identify a life byte the knowledge of which may be germane to a particular purpose and may also identify the data that are required to be collected for that life byte. The life bit processing layer may analyze life bits and related data. The life bit processing layer may generate conclusions and/or recommendations. The life bit processing layer may identify patterns in the life bits and life bytes. The life bit processing layer may identify missing information.

The life bit processing layer may generate reports. The life bit processing layer may auto-publish information, such as reports and studies. The life bit processing layer may auto-complete forms, such as medical records and insurance forms. The life bit processing layer may process, organize and manage life bits. The life bit processing layer may clean and de-duplicate life bits data. The life bit processing layer may perform extractions, transformations and loads of the life bits and life bytes data. The life bit processing layer may convert life bits and life bytes data to a common format. The life bit processing layer may aggregate, combine and collect life bits and life bytes data. The life bit processing layer may request missing data. The life bit processing layer may create databases and datamarts of life bits, life bytes and/or other data. The life bit processing layer may associate metadata with the life bits and life bytes.

The life bit processing layer may filter and/or apply contextual structures to life bits and life bytes data. The life bit processing layer may apply algorithms to life bits and life bytes data. The life bit processing layer may enable annotation of, or may auto-annotate, life bits and life bytes data. The life bit processing layer may be based on a push model, pull model or both. The life bit processing layer may process and/or clean data. The life bit processing layer may allow data from multiple sources to be combined. The life bit processing layer may organize and manage data, such as life bits and life bytes data. The life bit processing layer may aggregate and/or collect data, such as life bits and life bytes data. The life bit processing layer may enable storage and/or retrieval of data, such as life bits and life bytes data. The life bit processing layer may enable storage and/or retrieval of information based on or derived from data, such as life bits and life bytes data. The life bit processing layer may store and/or retrieve metadata. The life bit processing layer may read and/or write data and metadata. The life bit processing layer may enable versioning and/or partitioning.

Life byte(s), as described herein, may be determined directly from the data, from a data interface and/or through data processing. A life byte, as described herein, may be a life bit and/or may be determined through life bit processing. A life byte processing layer may sequence life bytes. The life byte processing layer may determine lifeotypes. The life byte processing layer may enable analytics and derivation. The life byte processing layer may create, generate, identify and/or discover life bytes and/or life byte sequences. The life byte processing layer may search for and identify patterns in the data to create life bytes and/or life byte sequences. The life byte processing layer may mine data. The life byte processing layer may identify missing information, which may assist in the creation, generation, identification and/or discovery of life bytes and/or life byte sequences. In an embodiment, the life byte processing layer may identify a life byte and/or life byte sequence the knowledge of which may be germane to a particular purpose and may also identify the data that are required to be collected for that life byte and/or life byte sequence. The life byte processing layer may analyze life bytes and/or life byte sequences and related data. The life byte processing layer may generate conclusions and/or recommendations. The life byte processing layer may identify patterns in the life bytes and/or life byte sequences. The life byte processing layer may generate a genotype of life byte sequences. The life byte processing layer may identify missing information.

The life byte processing layer may generate reports. The life byte processing layer may auto-publish information, such as reports and studies. The life byte processing layer may auto-complete forms, such as medical records and insurance forms. The life byte processing layer may process, organize and manage life bytes and/or life byte sequences data. The life byte processing layer may clean and de-duplicate life bytes and/or life byte sequences data. The life byte processing layer may perform extractions, transformations and loads of the life bytes and/or life byte sequences data. The life byte processing layer may convert life bytes and/or life byte sequences data to a common format. The life byte processing layer may aggregate, combine and collect life bytes and/or life byte sequences data. The life byte processing layer may request missing data. The life bit processing layer may create databases and datamarts of life bytes, life byte sequences data and/or other data. The life byte processing layer may associate metadata with the life bytes and/or life byte sequences data.

The life byte processing layer may filter and/or apply contextual structures to life bytes and/or life byte sequences data. The life byte processing layer may apply algorithms to life bytes and/or life byte sequences data. The life byte processing layer may enable annotation of, or may auto-annotate, life bytes and/or life byte sequences data. The life byte processing layer may be based on a push model, pull model or both. The life byte processing layer may process and/or clean data. The life byte processing layer may allow data from multiple sources to be combined. The life byte processing layer may organize and manage data, such as life bytes and/or life byte sequences data. The life byte processing layer may aggregate and/or collect data, such as life bytes and/or life byte sequences data. The life byte processing layer may enable storage and/or retrieval of data, such as life bytes and/or life byte sequences data. The life byte processing layer may enable storage and/or retrieval of information based on or derived from data, such as life bytes and/or life byte sequences data. The life byte processing layer may store and/or retrieve metadata. The life byte processing layer may read and/or write data and metadata. The life byte processing layer may enable versioning and/or partitioning.

A life byte sequence, as described herein, may be determined directly from the data, from a data interface and/or through data processing, may be a life bit and/or may be determined through life bit processing, may be a life byte and/or may be determined though life byte processing. A lifeotype data processing layer may identify lifeotypes. The lifeotype data processing layer may enable analytics and derivation. The lifeotype data processing layer may create, generate, identify and/or discover lifeotypes. The lifeotype data processing layer may search for and identify patterns in the data to create lifeotypes. The lifeotype data processing layer may mine data. The lifeotype data processing layer may identify missing information, which may assist in the creation, generation, identification and/or discovery of lifeotypes. In an embodiment, the lifeotype data processing layer may identify a lifeotype the knowledge of which may be germane to a particular purpose and may also identify the data that are required to be collected for that lifeotype. The lifeotype data processing layer may analyze life byte sequences, lifeotypes and related data. The lifeotype data processing layer may generate conclusions and/or recommendations. The lifeotype data processing layer may identify patterns in the life byte sequences and/or lifeotypes. The lifeotype data processing layer may generate a "genome" of lifeotypes. The lifeotype data processing layer may identify missing information.

The lifeotype data processing layer may generate reports. The lifeotype data processing layer may auto-publish information, such as reports and studies. The lifeotype processing layer may assemble lifeotypes into a "genome". The lifeotype data processing layer may auto-complete forms, such as medical records and insurance forms. The lifeotype data processing layer may process, organize and manage life byte sequences and/or lifeotypes data. The lifeotype data processing layer may clean and de-duplicate life byte sequences and/or lifeotypes data. The lifeotype data processing layer may perform extractions, transformations and loads of the life byte sequences and/or lifeotypes data. The lifeotype data processing layer may convert life byte sequences and/or lifeotypes data to a common format. The lifeotype data processing layer may aggregate, combine and collect life byte sequences and/or lifeotypes data. The lifeotype data processing layer may request missing data. The lifeotype data processing layer may create databases and datamarts of life byte sequences, lifeotypes data and/or other data. The lifeotype data processing layer may associate metadata with the life byte sequences and/or lifeotypes data.

The lifeotype data processing layer may filter and/or apply contextual structures to life byte sequences and/or lifeotypes data. The lifeotype data processing layer may apply algorithms to life byte sequences and/or lifeotypes data. The lifeotype data processing layer may enable annotation of, or may auto-annotate, life byte sequences and/or lifeotypes data. The lifeotype data processing layer may be based on a push model, pull model or both. The lifeotype data processing layer may process and/or clean data. The lifeotype data processing layer may allow data from multiple sources to be combined. The lifeotype data processing layer may convert data to a common format. The lifeotype data processing layer may organize and manage data, such as life byte sequences and/or lifeotypes data. The lifeotype data processing layer may aggregate and/or collect data, such as life byte sequences and/or lifeotypes data. The lifeotype data processing layer may enable storage and/or retrieval of data, such as life byte sequences and/or lifeotypes data. The lifeotype data processing layer may enable storage and/or retrieval of information based on or derived from data, such as life byte sequences and/or lifeotypes data. The lifeotype data processing layer may store and/or retrieve metadata. The lifeotype data processing layer may read and/or write data and metadata. The lifeotype data processing layer may enable versioning and/or partitioning.

A lifeotype, as described herein, may be determined directly from the data, from a data interface and/or through data processing, may be a life bit and/or may be determined through life bit processing, may be a life byte and/or may be determined though life byte processing, may be a life byte sequence and/or may be determined through lifeotype data processing. The Platform may contain an interface which may be an interface layer or interface facility. The interface may contain a user interface and/or presentation facility. The interface may publish reports, studies, conclusions and/or reports. The interface may automatically complete reporting documents and forms, such as medical records and insurance forms. The interface may auto-publish information, such as reports and studies. The interface may contain adaptors and/or connectors which allow the Platform to communicate and/or interface with other systems, facilities, data sources and the like. The interface may interface with an outside workflow, which may allow the platform to affect, optimize or improve efficiency of the outside workflow.

The interface may generate different views of the lifeotype data and/or other data. The interface may filter the lifeotype data and/or other data. The filtering may be done by sorting on a particular life bit, life byte and/or lifeotype, such as a medical condition or a state of activity. The filtering may also be done by sorting for a particular combination or combinations of life bits, life bytes or lifeotypes, such as sorting for all diabetics who are between the ages of 25 and 30 years old, engage in at least 10 hours of physical activity per week and eat more than 3 servings of vegetables per day. Filtering may allow for the identification of subsets of the data, which may be used for further studies. The interface may include an interface to sources and targets. The interface may function as a data clearinghouse.

The interface may include and/or be enabled or facilitated by a lifeotype markup language ("LML"). The interface may use or permit communication through LML. LML may facilitate the identification, creation, processing, manipulation and use of lifeotypes. LML may be a protocol. LML may be embodied in a header. LML may allow interfaces with other systems, platforms and the like, or may allow interfaces between elements of the Platform. LML may contain tags, which may function as connectors or links. The tags may link to other relevant data, or to data sources or sources of data values used in a particular calculation, derivation or analysis. A tag may link to other data, measured values or information that may be relevant or related, such as information recorded or created around the same time as the other data. A tag may link to information about mood or food consumption. In an embodiment, the LML corresponding to an energy expenditure calculation may contain links to data concerning the mood of the subject, food consumed by the subject and/or other medical values recorded at the time. A tag may enable a user to quickly locate or query data that form the basis of other information, derived measures and/or lifeotypes.

In one embodiment, LML may allow the specification of statements that include information about who the statement is about (at multiple levels of detail); what facts, if any, the statement is about; what patterns, if any, the statement is about; what actions or action sequences the statement is about; what time points or time periods the statement is about; what time points or time periods apply to the facts; any groups, patterns, or actions/action sequences; and the like. Abstraction to different levels of detail may be allowed for various features of LML. Abstraction to different levels of detail may be optional for each statement and certain fields may be optional in respect of a certain statement. In an embodiment, LML may utilize XML and may include the ability to have functional links and the like which may perform operations on a lifeotypes database.

A user interface may be tailored based on the user's lifeotype. A user interface may contain sliders, pistons or other means to adjust parameters. The user interface may show the effects of changes of certain parameters, such as on other parameters, or on lifeotype, medical conditions and the like. The user interface may show the effects of perturbing the system. Through the user interface it may be possible to tweak one or more sliders or adjust parameters in other ways and see the effect or predicted effect of those adjustments on other values and/or lifeotypes. Parameters that can be adjusted include the parameters in Table 3 of Andre, et al., pending U.S. patent application Ser. No. 10/682,293, for Method and Apparatus for Auto-Journaling of Continuous or Discrete Body States Utilizing Physiological and/or Contextual Parameters. The parameters disclosed therein apply to all embodiments herein utliziing sensed or measured data. The user interface may present reports, which may be auto-published, may include a comparison to other members of population and/or a comparison to other members of same or similar lifeotype profiles. A report may contain predictions, such as the probability of breaking a bone, having a stroke, having a major depressive episode and the like and may include recommendations on behavior, medication and the like. The report may include an interface with sliders that allow a user to perturb the recommendations and/or other aspects of the report and see the effects.

The Platform may contain users, which may be any of the users, consumers or parties described herein. The Platform may include data targets, which may be any of the databases or data structures described herein, including third party data sources. The Platform may contain a lifeotype systems, applications and/or services layer or facility which may enable any of the systems, methods, apparatuses, applications and/or services described herein. The Platform may also contain other systems, applications and/or services, which may be any of the systems, methods, applications and/or services described herein. The Platform may include a data administration layer, which may prohibit, restrict, enable and/or allow access to the Platform or particular aspects of the Platform based on certain factors. The data administration layer may enable conditional access. In an embodiment, access may be restricted by time, log-in location, whether the user is a participant in current study and the like. The data administration layer may enable differential levels of access. In embodiments, certain users may have access to only certain information, functions, data, results and the like. The data administration layer may enable logging, identification, authentication, security and privacy protection. The data administration layer may contain an anonymizer or one or more systems and/or methods by which users can opt-in and/or opt-out of certain aspects of the Platform or uses of information related to them. The opt-in/opt-out decision may be linked to a royalty system as discussed herein.

Figure 7:
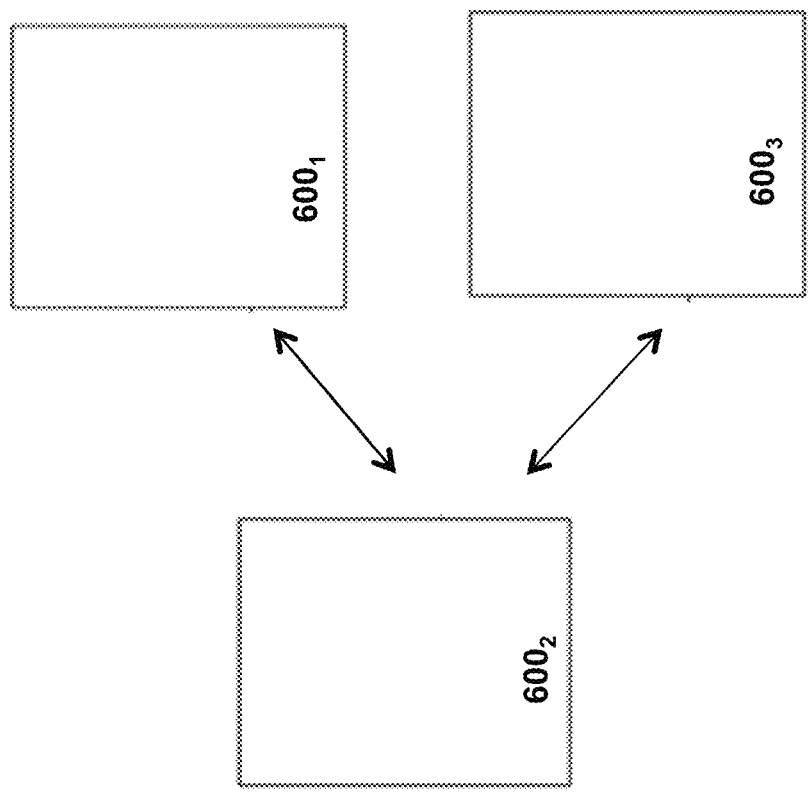
FIG. 7 depicts the scalability of the Platform.
Figure 8:
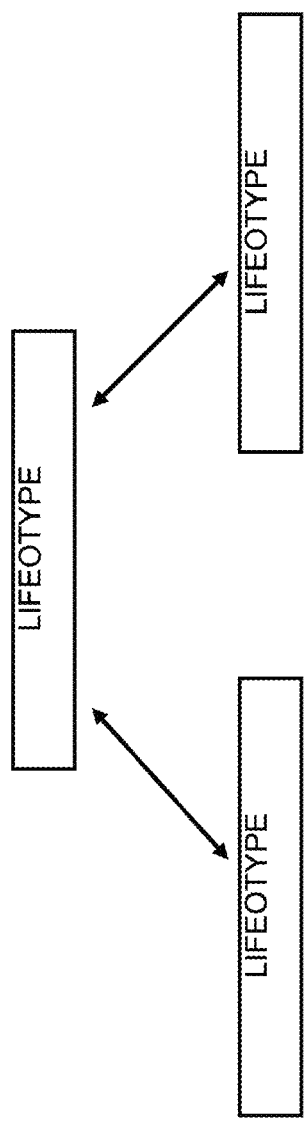
FIG. 8 depicts the scalability of lifeotypes.

Referring to FIG. 7 and elements $600_1$, $600_2$, and $600_3$ therein, the Platform may be scalable. In this regard, several different Platforms could be linked together or linked Platforms could be separated. Various different lifeotypes or lifeotypes of different people could be linked together or separated. Referring to FIG. 8, two or more lifeotypes can be linked or aggregated together to create new lifeotypes. In addition, a lifeotype may be separated into two or more lifeotypes.

Figure 9:
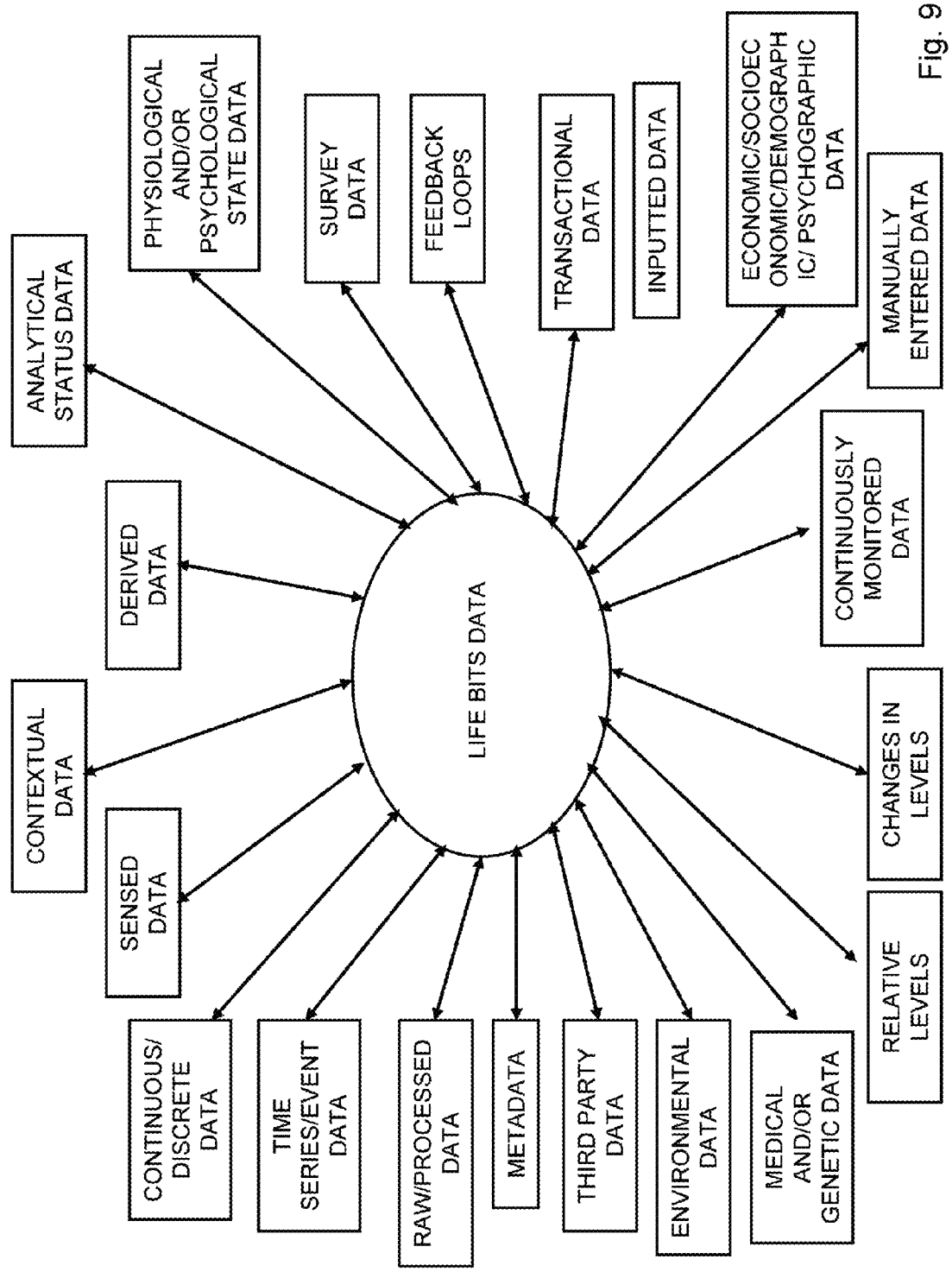
FIG. 9 depicts the types of data that may comprise life bits data.

The data discussed herein may be any measurable, describable or quantifiable aspect of the human condition and/or environment. The data may be human state data. The data may be energy expenditure data-energy expenditure data, which may act as a surrogate for vital sign data. Referring to FIG. 9, the data may fall into one or more general categories of data, including derived data, analytical status data, contextual data, continuous data, discrete data, time series data, event data, raw data, processed data, metadata, third party data, data regarding physiological state, data regarding psychological state, survey data, medical data, genetic data, environmental data, transactional data, economic data, socioeconomic data, demographic data, psychographic data, sensed data, continuously monitored data, manually entered data, inputted data, relative levels, changes in levels and feedback loop data. In embodiments, the data may be constructed of derived data and a basic parameter to determine an inverse. In embodiments, the data may be constructed of derived data and environmental data. In embodiments, the data may be constructed of derived data and physiological data. The physiological data may include information regarding a disease condition and the progress of the disease (becoming better or worse).

Figure 10:
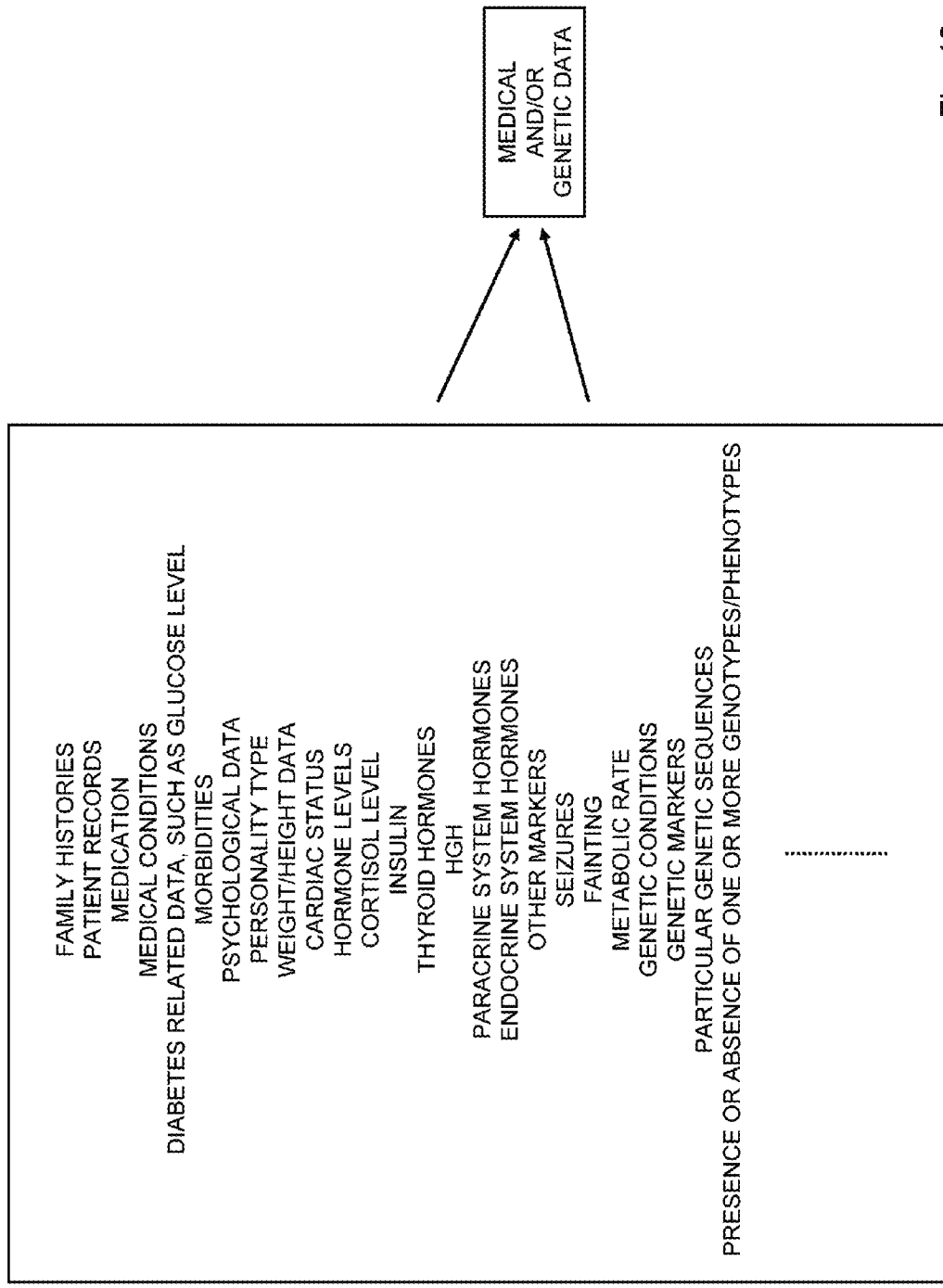
FIG. 10 depicts the types of data that may comprise medical and/or genetic data.
Figure 12A:
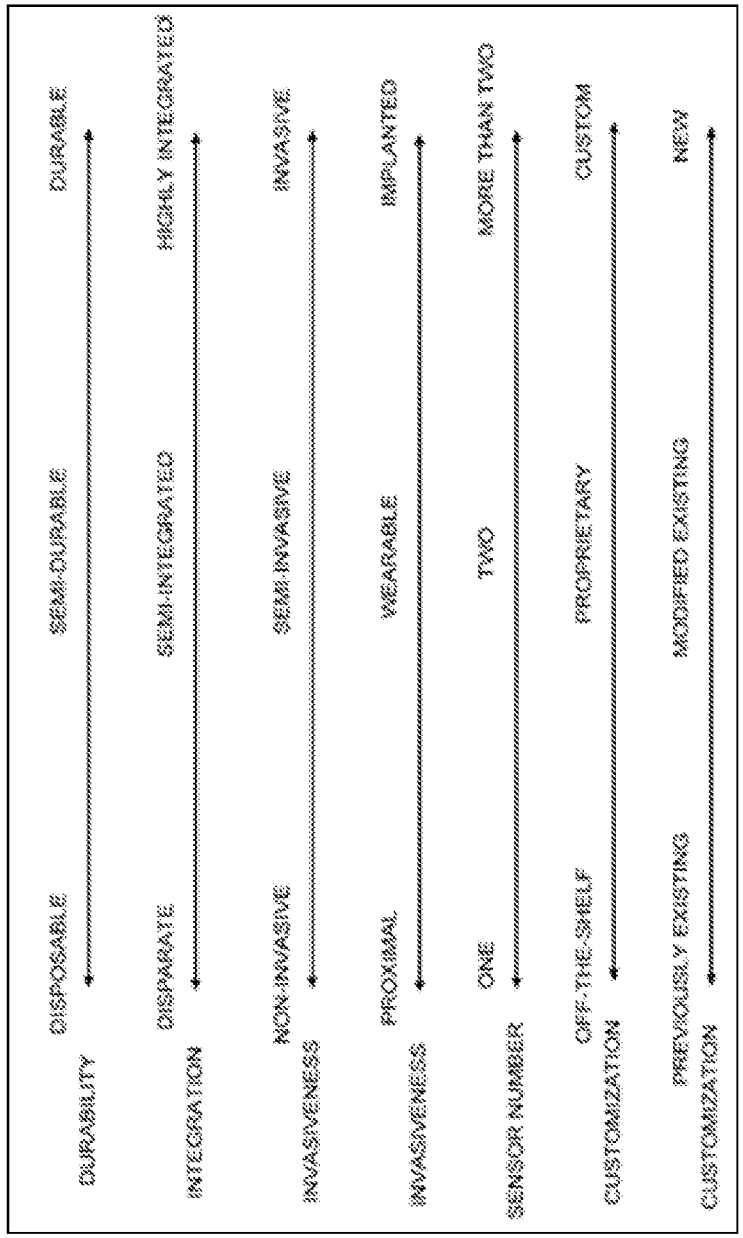
FIGS. 12A, 12B, 12C and 12D depict the types of data that may comprise derived data as well as various spectra applicable to sensors, data and/or the Platform.
Figure 12B:
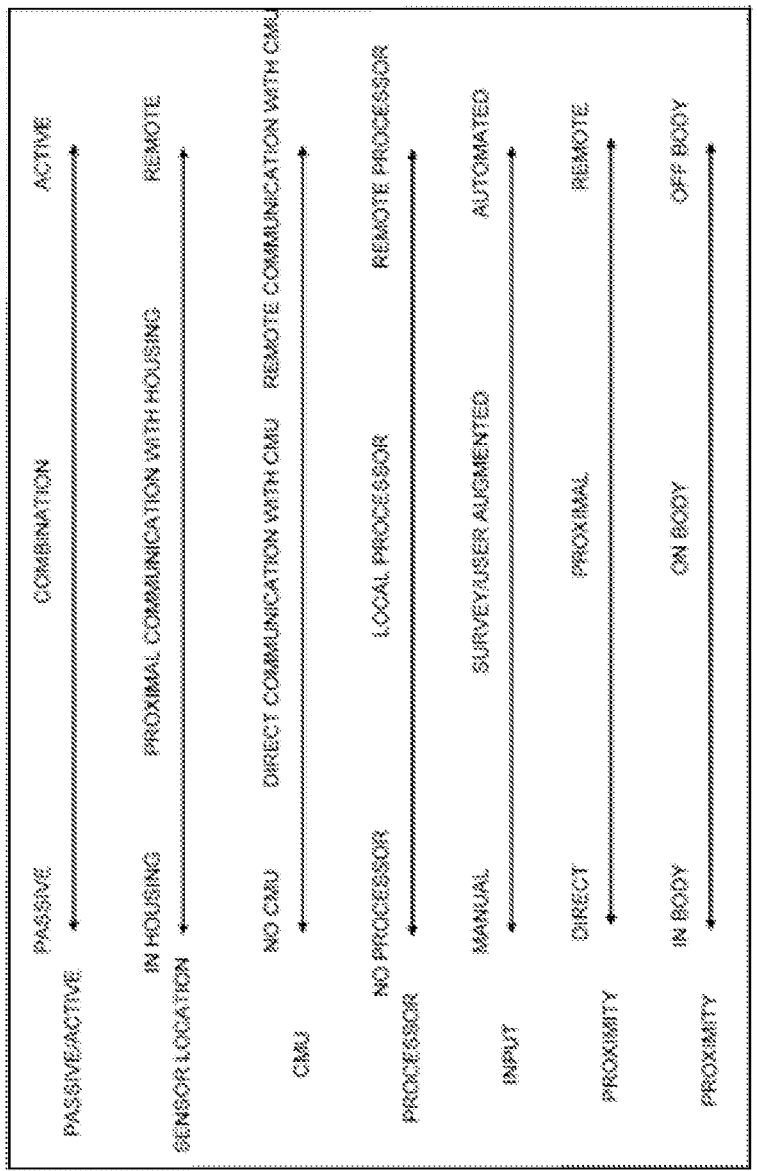
Figure 12C:
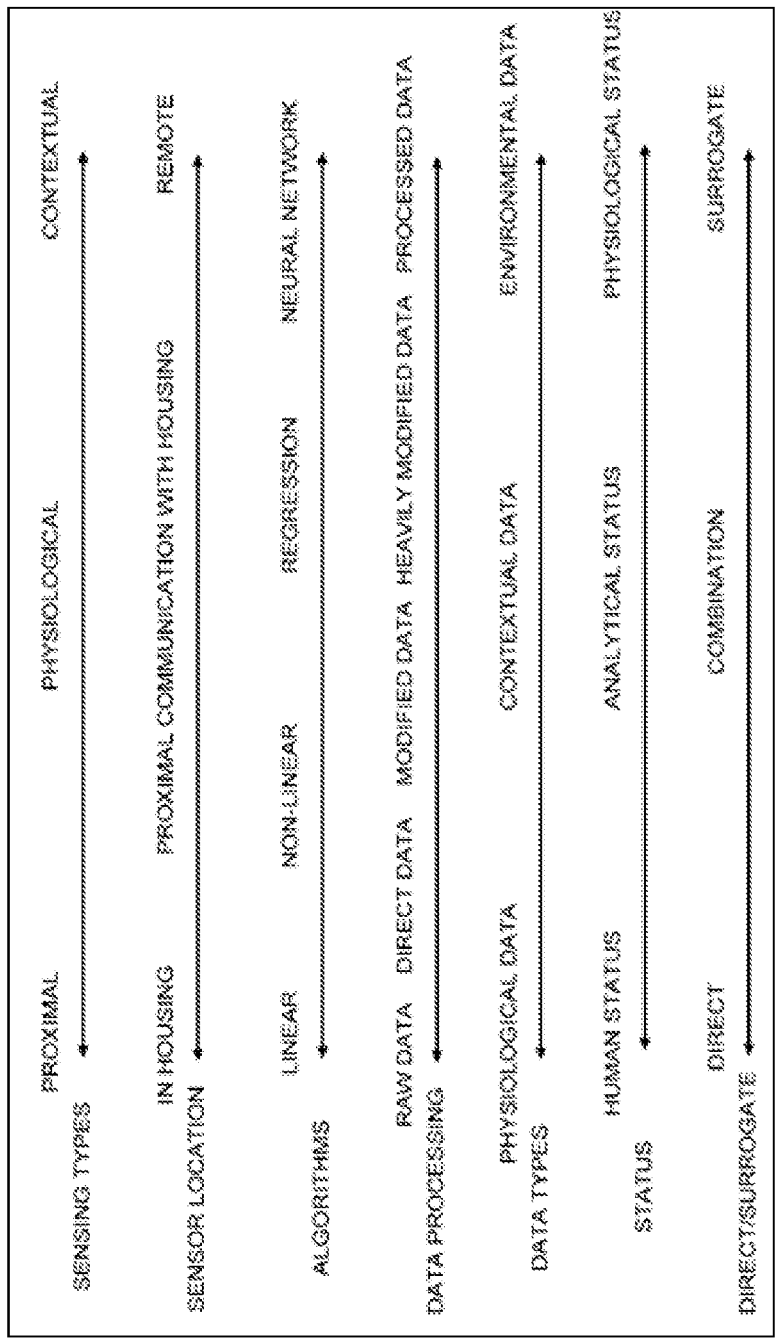
Figure 12D:
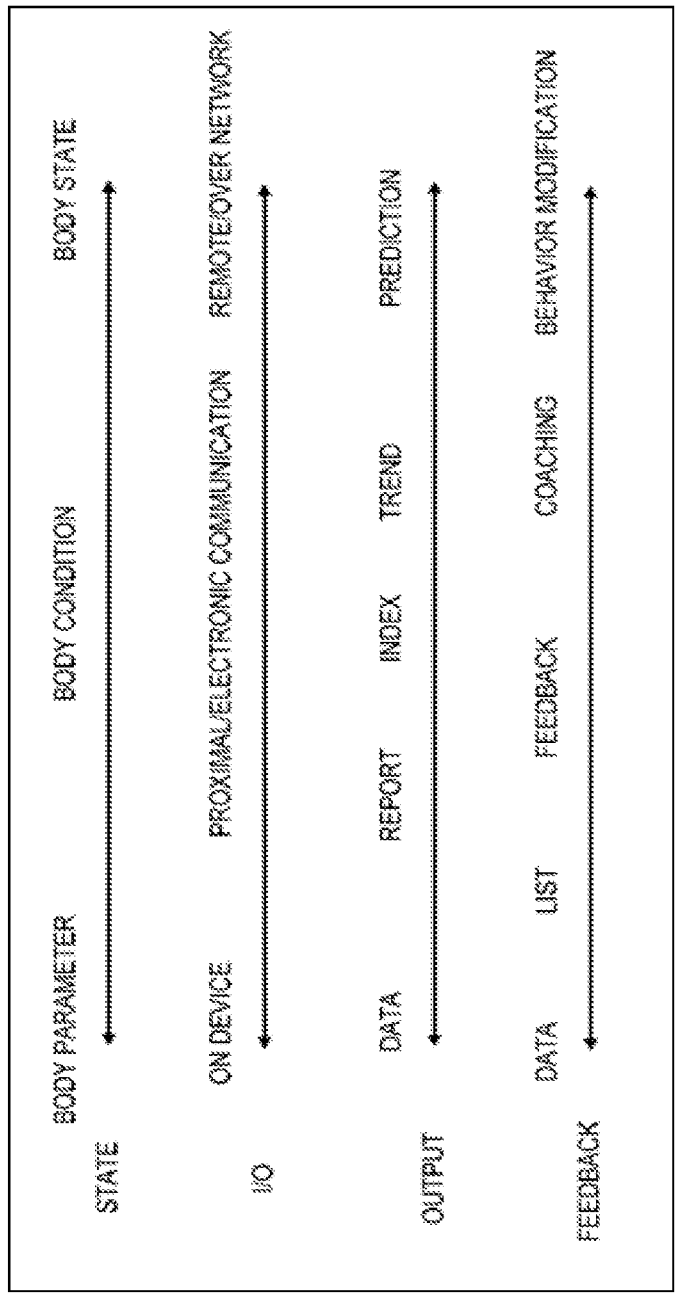

The data may also be specific instances of data, such as any variable or field of the Platform. A specific instance of data may be data regarding physiological and/or psychological state. Referring to FIG. 10, the data may be medical data. The medical data may be diabetes related data (such as glucose level), family histories, patient records, medication, medical conditions, morbidities, psychological data (such as personality type), weight data, height data, cardiac status data, hormone level data (such as for cortisol, insulin, thyroid hormones, HGH, paracrine system hormones and/or endocrine system hormones), data relating to medical conditions (such as type I diabetes, type II diabetes or a particular syndrome), data relating to markers, data relating to seizures, data relating to fainting, metabolic rate data, data relating to physical measurements and/or conditions (such as a weakened heart wall), genetic data (such as data concerning genetic conditions, genetic markers, particular genetic sequences and presence or absence of one or more genotypes and/or phenotypes) and/or data relating to diagnostics.

The data may be transactional data, such as data concerning goods or services purchased, consumed and/or desired. The transactional data may be from credit or debit card purchases, from third party databases, from manually entered data (such as user entered data), from a purchasing program associated with the Platform, from internet browsing history, from items placed on layaway, from needs anticipated or predicted by the Platform, from a record of online purchases and the like. The transactional data may relate to grocery purchases, usage of different utilities (such as water, hydro, gas and the like) and the like. The transactional data may include predictions based on past data. The data may be measured with sensor-packages monitoring multiple individuals.

Referring to FIG. 11, the data may include environmental data. Environmental data may include data relating to light level (such as for sunlight and/or artificial light), weather, ambient temperature, humidity, wind, air quality, atmospheric conditions, water quality, environmental problems, location and/or nutrition (such as concerning food, beverages, vitamins and/or diet). The data may include contextual and/or situational data. The contextual and/or situational data may relate to social context. In an embodiment, the social context may be out with friends or at home alone. The contextual and/or situational data may relate to life-cycle context. In an embodiment, the life-cycle context may be in college, in the workforce, married with children and the like. The contextual and/or situational data may relate to activity level (such as sedentary or exercising), meditation state, body position, travel (such as in a car, on a plane, on a train, at sea and the like), shopping, entertainment level (such as at a concert, movie and the like), location (such as determined by GPS or triangulation), miles driven as a passenger, miles driven as a driver, where driven, travel destinations, type of work (such as physical labor or deskwork), hours worked, sleeping, resting and/or arguing.

The data may include personality and/or psychological data. The personality and/or psychological data may include data relating to entertainment choices, mood, amount of time spent reading, books read, topics of material read, authors of material read, amount of fiction read, amount of non-fiction read, amount of time spent watching television and movies, television programs watched, movies watched, topics of television programs watched, topics of movies watched, moods of television programs watched, moods of movies watched, amount of time spend playing games and videogames, games or videogames played, topics of games or videogames played, moods of games or videogames played, skill level of games or videogames played, levels obtained in games or videogames played, activity level determined from games or videogames played (such as for a Nintendo Wii console), amount of time spent on certain websites, language context typed into keyboard, voice stress levels, entertainment choices, leisure choices, choice of sports, choice of active lifestyle versus sedentary lifestyle, estimated mental state data (such as data concerning intentions) and the like.

Referring to FIGS. 12A-12D, the data may be derived data. The derived data may relate to stress, cortisol level, activity level, energy expenditure, heart rate variability, hydration, pulse oximetry, profusion of small vessels, sleep state, sleep onset, VO2 from energy expenditure, glucose from energy expenditure, pain from energy expenditure, combinations of derived parameters and the like.

The data may also include metadata. The metadata may include data regarding when a particular item of data was measured, how the item was measured, where a particular item of data was measured, the context in which the item of data was measured, who measured the item, other related items of data that were measured, the reason the item of data was measured, relationships of the item to other items, related items that were not measured or recorded, other items with which the data item is shared and the like. The metadata may include information regarding how the item of data came to be and how the item of data acts in its natural state. Related items of data may be measured at different times and places, by different methods and for different purposes. The data may include action state information, activity state information, project state information and relationship information, including data between and/or among individuals.

The data may come from various sources. Sources of data may include data from a wearable body monitor, from sensors/transducers, from communications technologies, from data integration technologies, from software services (such as feeds and web services), from metadata, from manual entry, from user input, from user interfaces (such as from buttons, dials, sliders, graphical user interfaces and the like), from third party sources, from databases, from surveys, from derived data, from records and transaction histories (such as library records, video rental records, media playlists, receipts, financial statements, credit card statements, bank statements and the like) and the like. Data may also be obtained from non-invasive means and passive or indirect data gathering.

Data may be obtained from sensors and/or body monitors. A sensor or body monitor may have a specific shape or form, such as an arm band or garment. A sensor or body monitor may be worn in specific locations, such as on the arm or around the waist. A sensor or body monitor may be wearable. Examples of body monitors other systems, devices, and methods that can be used to generate the data rendering life bits and ultimately lifeotype data are described in described in Stivoric et al., U.S. Pat. No. 7,020,508, issued Mar. 28, 2006, entitled Apparatus for Detecting Human Physiological and Contextual Information; Teller et al., pending U.S. patent application Ser. No. 09/595,660, for System for Monitoring Health, Wellness and Fitness; Teller, et al., pending U.S. patent application Ser. No. 09/923,181, for System for Monitoring Health, Wellness and Fitness; Teller et al., pending U.S. patent application Ser. No. 10/682,759, for Apparatus for Detecting, Receiving, Deriving and Displaying Human Physiological and Contextual Information; Andre, et al., pending U.S. patent application Ser. No. 10/682,293, for Method and Apparatus for Auto-Journaling of Continuous or Discrete Body States Utilizing Physiological and/or Contextual Parameters; Stivoric, et al., pending U.S. patent application Ser. No. 10/940,889, Stivoric, et al., pending U.S. patent application Ser. No. 10/940,214 for System for Monitoring and Managing Body Weight and Other Physiological Conditions Including Iterative and Personalized Planning, Intervention and Reporting, and Stivoric et al., pending U.S. patent application Ser. No. 11/582,896 for Devices and Systems for Contextual and Physiological-Based Detection, Monitoring, Reporting, Entertainment, and Control of Other Devices, each of which are incorporated, in their entirety, herein by reference.

In an embodiment, the data may be obtained from an apparatus for detecting, monitoring and reporting human status information, comprising a sensor device including at least two sensors selected from the group consisting of physiological sensors and contextual sensors, said sensors each capable of generating a data stream, wherein a first data stream comprises data indicative of at least a first parameter and second data stream comprises data indicative of at least a second parameter of an individual; and a computing device in electronic communication with said sensor device, said computing device receiving at least a portion of said data streams and generating derived data based on said data indicative of at least a first parameter and said data indicative of at least a second parameter, said derived data used to control said computing device. In an embodiment, the data may be obtained from an apparatus for detecting, monitoring and reporting human status information, comprising a sensor device including at least two sensors selected from the group consisting of physiological sensors and contextual sensors, said sensors each capable of generating a data stream, wherein a first data stream comprises data indicative of at least a first parameter and second data stream comprises data indicative of at least a second parameter of an individual; and a computing device in electronic communication with said sensor device, said computing device receiving at least a portion of said data streams and generating derived data based on said data indicative of at least a first parameter and said data indicative of at least a second parameter, said derived data used to control a device separate from said computing device.

Referring to FIGS. 12A-12D, the sensor or body monitor may be disposable, semi-durable or durable. The sensor or body monitor may be highly integrated, semi-integrated or disparate. In an embodiment, a sensor may be highly integrated into a garment. The sensor or body monitor may be non-invasive, semi-invasive or invasive. The sensor or body monitor may be implanted, wearable or proximal. The data may be obtained from one sensor, two sensors or more than two sensors.

The sensor or body monitor may be customized, proprietary or off-the-shelf. The sensor or body monitor may be newly created, a modified existing sensor or body monitor or a previously existing sensor. The sensor or body monitor may be passive, active or a combination of passive and active. The sensor or body monitor may be located in a housing, in communication with a housing or located remotely. The sensor or body monitor may be in remote communication with a central monitoring unit, in direct communication with a central monitoring unit or may be not related to a central monitoring unit. The sensor or body monitor may be utilized in connection with a remote processor, a local processor or without a processor. The sensor or body monitor may be automatic, user augmented, survey augmented or manual.

The sensor or body monitor may be direct, proximal or remote. The sensor or body monitor may be in body, on body or off body. The sensing of the sensor or body monitor may be proximal, physiological or contextual. The sensor or body monitor may be located in a housing, in proximal communication with a housing or remote to a housing. The sensor or body monitor may be used in connection with linear algorithms, non-linear algorithms, regression analysis and/or neural networks. The data obtained from the sensor or body monitor may be raw data, direct data, modified data, heavily modified data or processed data. The data sensed by the sensor or body monitor may be physiological data, contextual data and/or environmental data.

The sensor or body monitor may be implantable. An implantable sensor or body monitor may be a pacing system, such as a heart pacemaker, cardiac pacemaker and the like. An implantable sensor or body monitor may be a carioverter defibulator. An implantable sensor or body monitor may be a blood pressure flow sensor, which may be MEMS-based. The sensor or body monitor may be a sleep apnea recorder, continuous positive air pressure device, ECG, Holter monitor, glucometer, pulse oximeter, blood pressure monitor, sphygmomanometer, heart rate monitor, chest strap or the like. The sensor or body monitor may be disposable, such as a patch. The sensor or body monitor may be capable of sensing physiological parameters such as glucose and other analytes contained in interstitial fluid. The sensor or body monitor may be may include chemical agents, electrotransport, ultrasound, microprojections, microneedles, analog or digital weight scale and the like. The sensor or body monitor may be may be included in fitness equipment such as cardio equipment, weight training equipment, scales, sports equipment, entertainment devices in gyms and the like. The sensor or body monitor may be included in consumer electronics, such as MP3 players and phones. The sensor or body monitor may be included in entertainment devices, such as videogame consoles. The sensor or body monitor may be included in GPS units. The sensor or body monitor may be included in home appliances and home automation devices, which may control lighting, temperature, window coverings, security systems and access control, personal assistance, home theater and entertainment, phone systems and the like. The sensor or body monitor may be included in other device automation, such as a car, MP3 player and the like.

Figure 13:
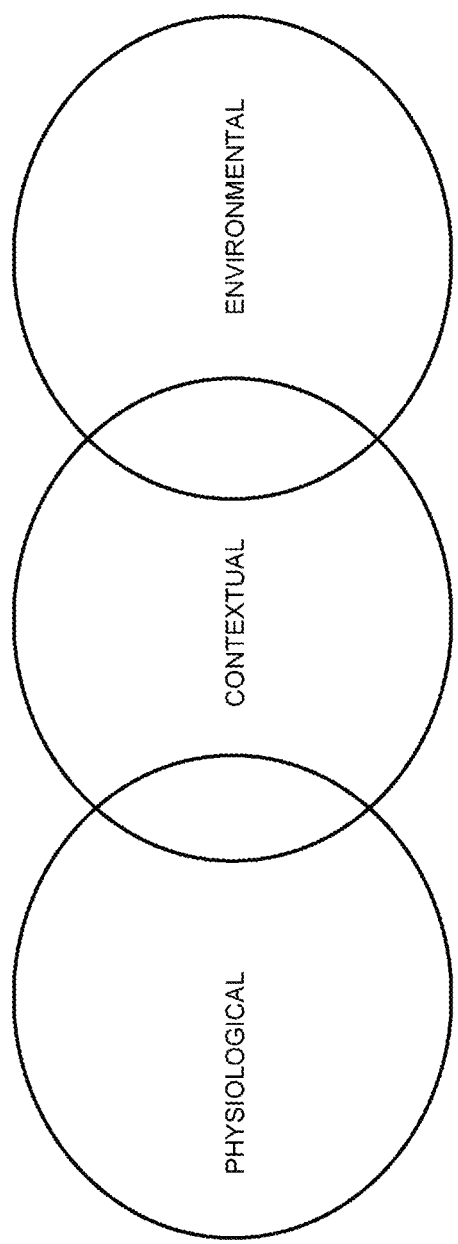
FIG. 13 depicts the relationship among physiological, contextual and environmental data.
Figure 14:
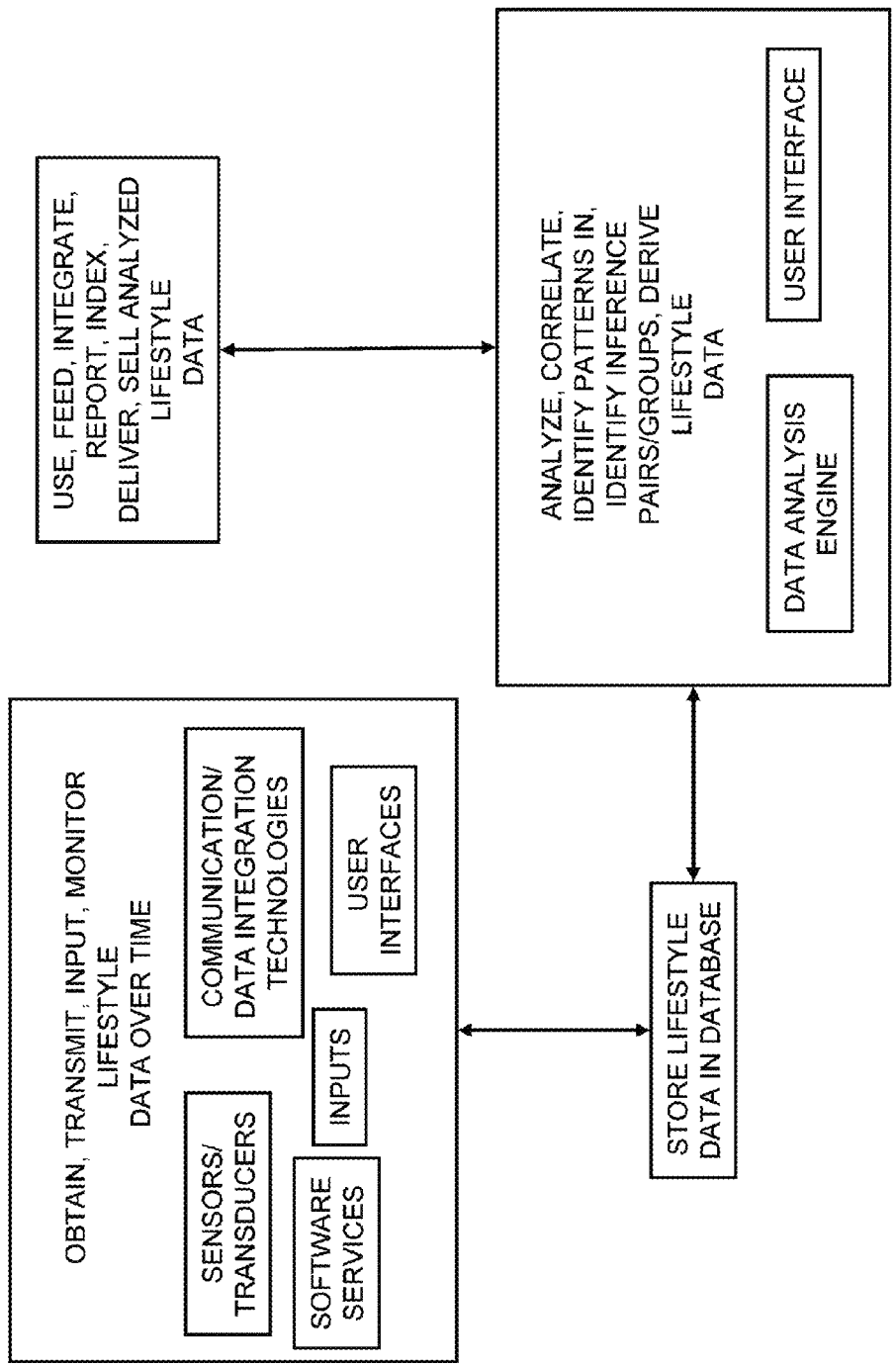
FIG. 14 depicts a process flow for identifying lifeotypes.
Figure 15:
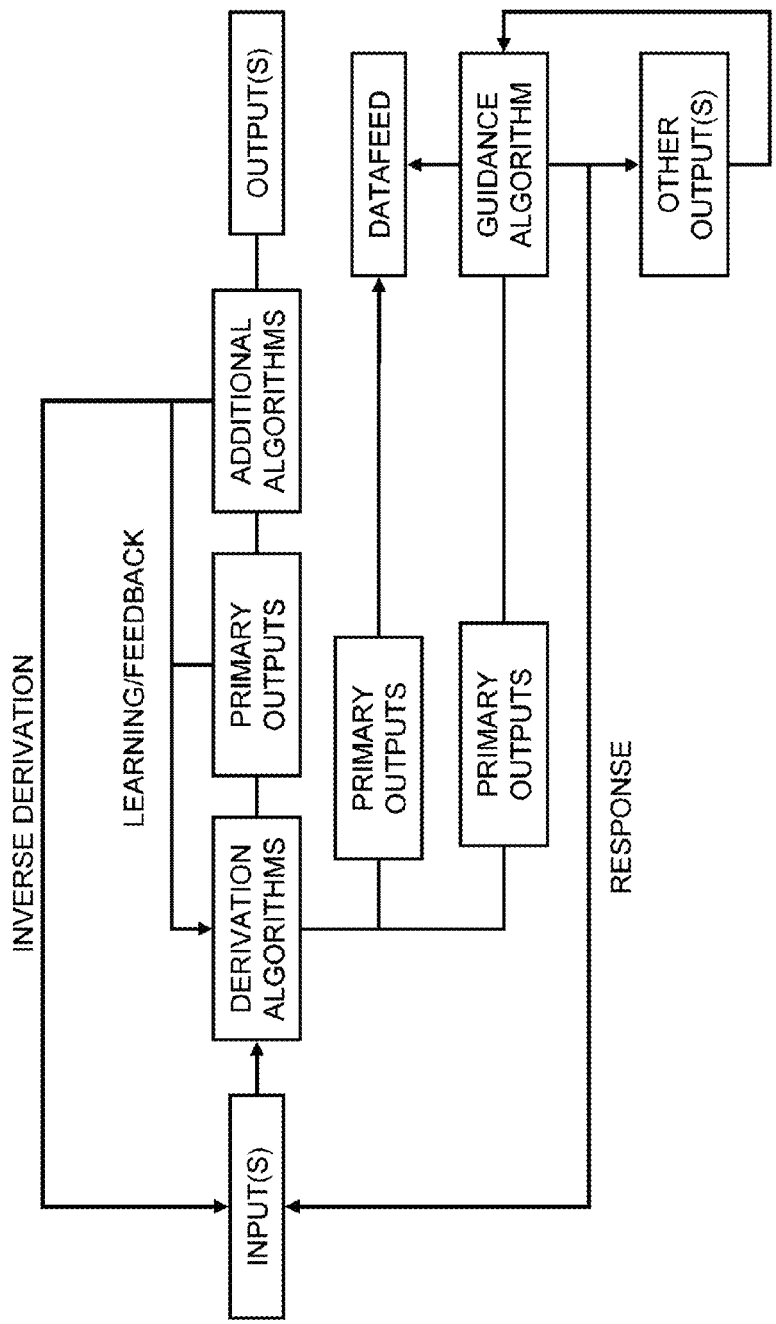
FIG. 15 depicts a process flow for analyzing lifeotypes.
Figure 16:
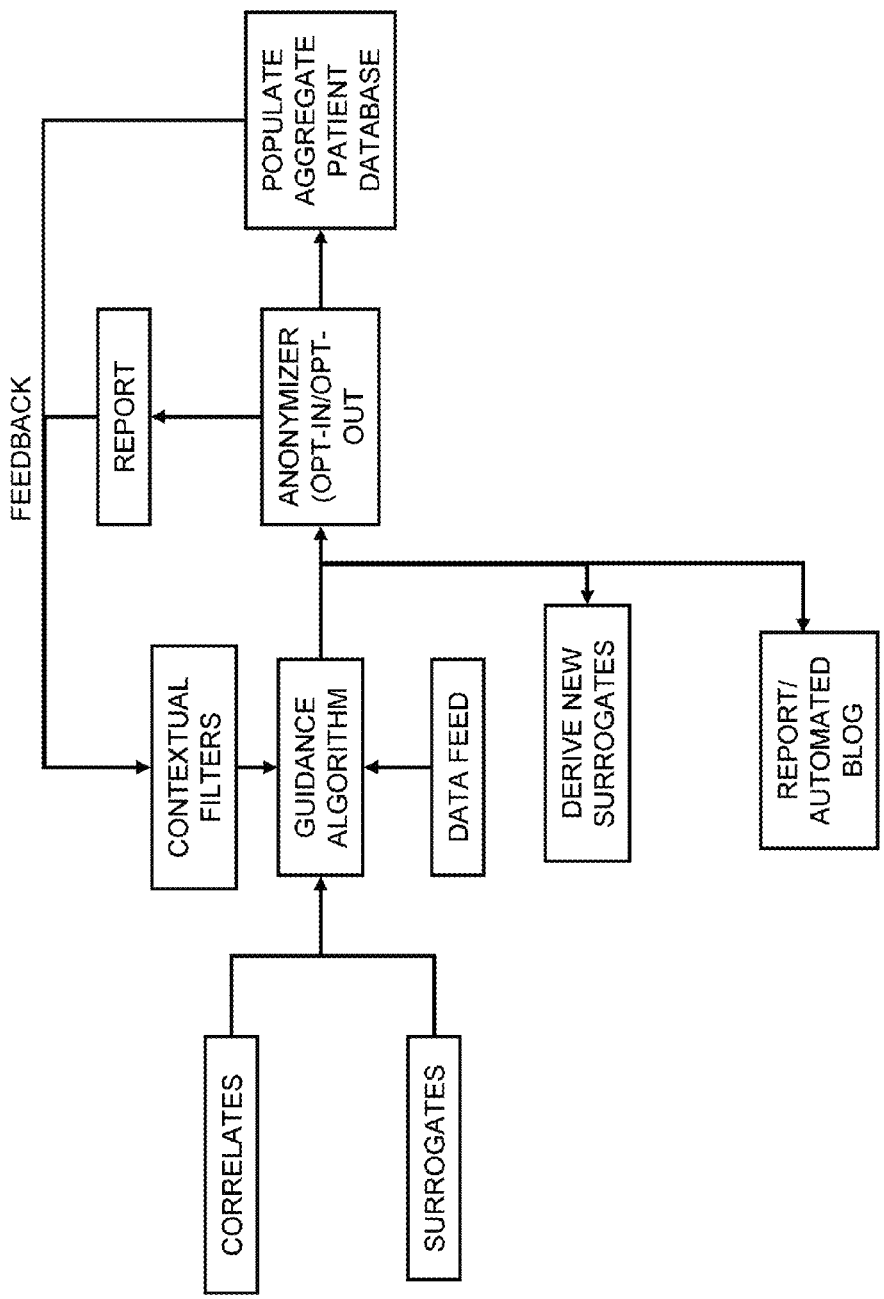
FIG. 16 depicts a process flow for analyzing lifeotypes.
Figure 17:
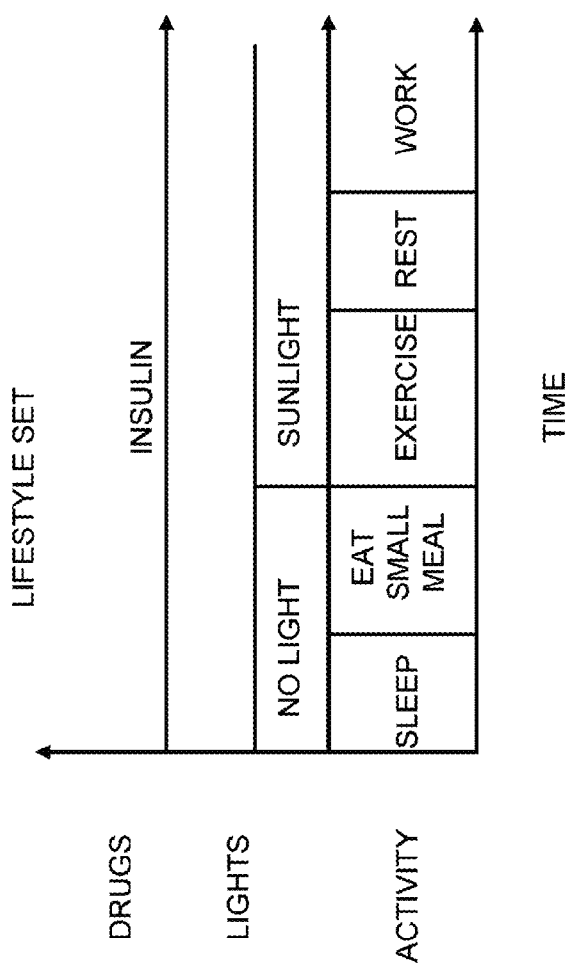
FIG. 17 depicts a lifeotype state diagram.

Referring to FIG. 13, data may be physiological data, contextual data and/or environmental data. Physiological data may come directly from the body and may be measured in a fairly direct fashion. In an embodiment, physiological data may be heart rate, respiration rate or whether an individual is asleep or not asleep. Contextual data may include some connotation of context. Contextual data may be a subset of environmental data, such as temperature near the body. Environmental data may include information about the environment the body is in, such as ambient temperature. The sensor or body monitor may be any one or more physiological sensors, contextual sensors and/or environmental sensors. Other types of contextual, physiological and environmental data are disclosed in pending U.S. patent application Ser. No. 11/582,896 for Devices and Systems for Contextual and Physiological-Based Detection, Monitoring, Reporting, Entertainment, and Control of Other Devices, each of which are incorporated, in its entirety, herein by reference.

Referring back to FIG. 12A-12D, the data sensed by the sensor or body monitor may be human status data, analytical status data or physiological status data. The data may be not derived, may be derived, may be a derived third parameter or may be modified by a first or second parameter. The data may be direct, compressed or filtered. The data may be a surrogate or third parameter. The data sensed by the sensor or body monitor may be direct data, surrogate data or a combination of direct and surrogate data. The data may be condition data. The condition may be composed of a number of parameters and may be composed of a number of conditions. The data obtained from the sensor or body monitor may related to a body parameter, body condition and/or body state. The sensor or body monitor may contain or be used in connection with an I/O, which may be on the sensor device or body monitor, proximal or in electronic communication with the sensor device or body monitor or remote to the sensor device or body monitor. The output of the sensor or body monitor may be or may form the basis for a report, index, trend or prediction. Feedback may be provided based on the data sensed by the sensor or body monitor. The feedback may be in the form of a list, coaching or behavior modification.

In an embodiment, the data may be obtained from a group of individuals waiting for heart transplants. The data may include medical values of the true declining cardiac output of the individuals. The data may also include changes in cardiac output or other body conditions when individuals are moved up or down the waiting list for a new heart. The data may include information regarding which individuals died before a heart was ready for them and the details of each death. This data may relate to life bit and life byte information (such as EE) to find a life byte that changes in a way that will allow for sorting of individuals on the heart transplant waiting list to minimize deaths of people on the list and to maximize the chances of survival after the operation, or other metrics of success.

In an embodiment, the data may include data relating to, or the platform may analyze a subpopulation composed of, a group of individuals that have some known and unusual outcome, conditions or situation. For example, the condition may be a rare mental disease, such as a split personality. The platform may enable identification of one or more life bytes that cluster this group; that is, separate them from the rest of the population. In an embodiment, the group may be individuals with MS and the life byte may be subtle but measurable changes in their activity lengths and patterns relative to their norms in the year just before they are diagnosed with MS.

In an embodiment, the platform may allow for identification of a group of individuals that have some known and unusual life byte. The platform may then be used to, or may itself, look for what outcomes or situations each individual shares with others from this group. For example, the platform may find that 0.1% of the population exercises more than 4 hours a day every week and yet never exercises more than 1 day a week. The platform may identify characteristics that the people with that lifebyte have in common. For example, the platform may identify that they all die before 60 years of age.

The platform may be used to conduct event studies and experiments. In an embodiment, the platform may be used to identify a group of individuals that have a certain outcome or characteristic, such as, for example, high stress. The platform may also be used to identify certain other events or interventions that happened to certain subgroups of the group of individuals. In this way that effects of the events or interventions can be studied. As a result, the database can be used to determine the effects of the intervention on the group of people, without additional experimentation. The platform may allow a user to form a hypothesis and then examine or watch related groups of individuals in the database to confirm or reject the hypothesis. The hypothesis may be modified over time based on changes in the data, such as the subsequent effects of the events and interventions of interest. The hypothesis may be reinforced, broken down and rebuilt. This may be an iterative process.

The platform may be used for predictions. In an embodiment, a user may describe or input their life bits, life bytes and other relevant information and the platform may determine lifeotypes or predict health, wealth, happiness outcomes and the like. The predictions may be based on information for individuals with similar life bits, life bytes, lifeotypes and related information. In another embodiment, the platform may allow a user to explore the effects of certain changes on lifeotypes and outcomes. For example, the platform may allow a user to answer the following question: if I changed my life bytes in this way, what should I expect in terms of changed health, wealth, happiness and the like?

Figure 26A:
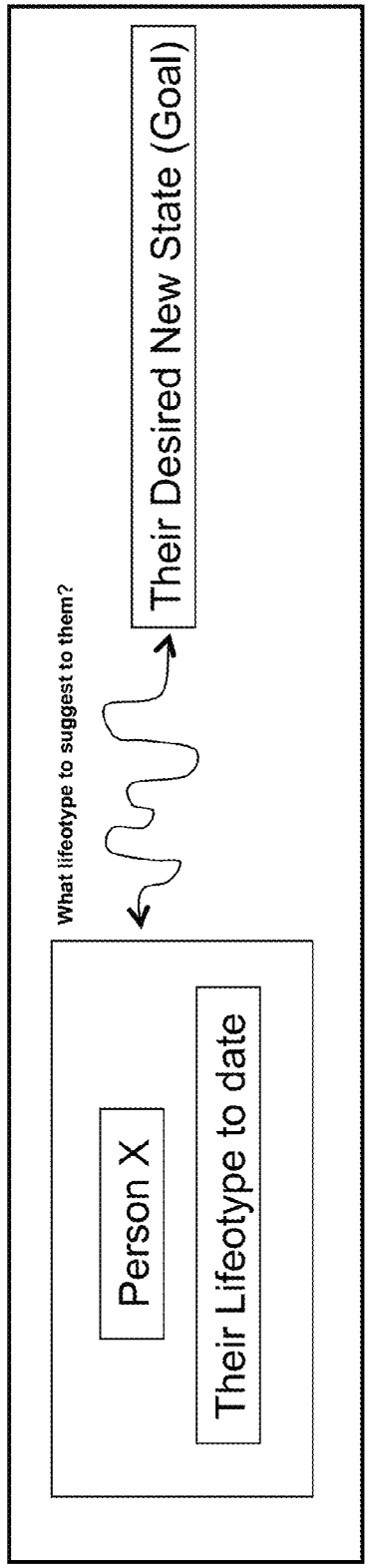
FIGS. 26A and 26B depict a particular embodiments of affecting behavior through lifeotypes.
Figure 26B:
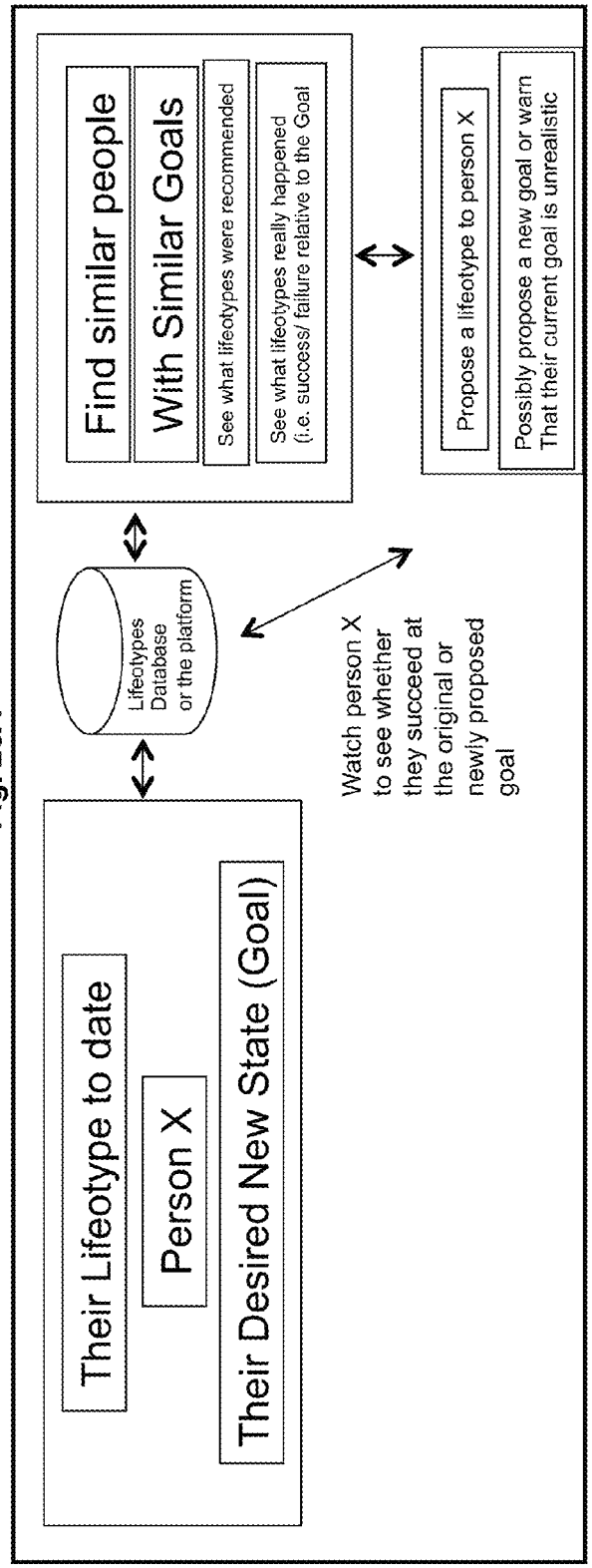

The platform may enable maximization along certain dimensions. Referring to FIGS. 26A-26B, in an embodiment, the platform may allow a user to "hill climb" to the local maximum that seems like a reasonable set of changed life bytes for a particular person such that it will maximize her health, wealth, happiness and the like. The user may be able to assign various weights to the various outcomes to indicate their relative importance to her. The platform may base the optimization, at least in part, on data relating to other individuals, such as what is a reasonable set of suggestible life byte changes for this person based on other similar people and whether or not similar people have been able to change their lifeotypes in this way.

The platform may allow for comparisons. In an embodiment, the platform may allow users to compare their life bit, life byte, lifeotype and other information and outcomes to other individuals or groups of individuals, such as similar individuals or groups of similar individuals. In an embodiment, the platform may enable a one legged man in the deep South who sleeps poorly and is overweight to compare himself to similar individuals, whether currently existing or based on past data, who are also trying to lose weight.

Life bits, life bytes, lifeotypes and/or related information may be used to predict, determine or ascertain other characteristics or preferences of a user or group of users. In an embodiment, fife bits, life bytes, lifeotypes and/or related information regarding a user's activity, activity, sleep patterns, body position and motoring times and length may be used as the inputs to predict the movies or books or cars the user will like.

The platform may allow for geospatial and visual presentation of life bits, life bytes, lifeotypes and/or related information. In an embodiment, a Google-Earth style interface may be used to display life bits, life bytes, lifeotypes and/or related information. The interface may show life bits, life bytes, lifeotypes and/or related information for a particular population or the entire world in a visually appealing and explorable way. In an embodiment, the platform may superimpose life bits, life bytes, lifeotypes and/or related information over a 3D globe so that a user can see where people are awake, asleep, active, sedentary, stressed, calm and the like.

The platform and life bits, life bytes, lifeotypes and/or related information may be used for financial analysis and/or to predict information that is monetizable. In an embodiment, the platform, life bits, life bytes, lifeotypes and/or related information may be used to predict changes in the stock market, or particular securities or groups of securities, based on changes in life bits, life bytes, lifeotypes and/or related information. In an embodiment, the life bits, life bytes, lifeotypes and/or related information may be from around the country or a particular region. In an embodiment, the platform may aggregate the life bits, life bytes, lifeotypes and/or related information into indexes, such as a "people are getting sadder/pessimistic" and a "people are getting happier/optimistic" index. The platform may then use those indexes or indicators to predict near term and long term trends in the overall market, or a subset of the market. In another embodiment, the platform may enable prediction of individual stock trends from specific changes in life bits, life bytes, lifeotypes and/or related information. For example, if people start jogging more, it may be advisable to stock in running shoe companies, such as Nike. If people start walking more it may be advisable to buy more stock in Weight Watchers. In another embodiment, the platform, life bits, life bytes, lifeotypes and/or related information may be used to predict information relating to sporting events. For example, the information may be useful for betting on sporting events. The platform may allow for aggregation of information across many people connected to the sporting event.

The platform may be used for epidemiology applications. In an embodiment, the platform, life bits, life bytes, lifeotypes and/or related information may be used to predict the onset of a flu outbreak in a city 12 to 24 hours before it is otherwise seen by watching for subtle shifting patterns in life bits, life bytes, lifeotypes and/or related information, such as higher estimated core temperature or lower activity, adjusting for other relevant factors such as location, time of day, weather patterns and the like. In another embodiment, the platform may be used to identify patterns of behaviors, life bits, life bytes, lifeotypes and/or related information that lead to a certain outcome, such as a positive outcome. For example, sleeping 9 hours per night and exercising every day before noon may result in weight loss. In an embodiment, this information may be used to create a service business.

The platform may be used for data business applications. In an embodiment, access to life bits, life bytes, lifeotypes and/or related information may be sold or licensed. In an embodiment life bits, life bytes, lifeotypes and/or related information may be sold. In an embodiment, a particular aggregate view of certain life bits, life bytes, lifeotypes and/or related information may be sold to academics for the purpose of conducting outcome studies. This may allow the studies to be performed on a much shorter time scale of a few minutes as opposed to several years. The platform may also allow for identification of groups of interest. In an embodiment, the platform may allow for identification of individuals with certain life bits, life bytes, lifeotypes and/or related information of interest. The platform may enable a user to contact those people to seek additional information. In embodiments, the people may be paid or given other consideration to provide the missing or additional information. In an embodiment, the platform may allow a user to identify a group of people who take a particular pill, are of a particular ethnicity, and have a particular stress level. The user may want to know the fasting glucose level of these people, but that data is not available. The platform may enable the user to, directly or indirectly, contact all or a portion of these people, or one or more of their representatives, to obtain the fasting glucose level information. The people or their representatives may be paid for the information. The newly obtained information may then be used in other applications.

The platform may be used for planning applications. In an embodiment, the platform may be used to automate budgeting and city planning. In an embodiment, instead of giving each state and city money based on how much the state or the American Automobile Association says the roads are utilized, life bits, life bytes, lifeotypes and/or related information may be used to make the determination. The determination may be made on a periodic basis, such as quarterly or annually, and the budget adjusted. The platform may be used for similar applications in the healthcare field. In an embodiment, the platform may utilize behavioral census information in connection with the determinations.

Figure 27A:
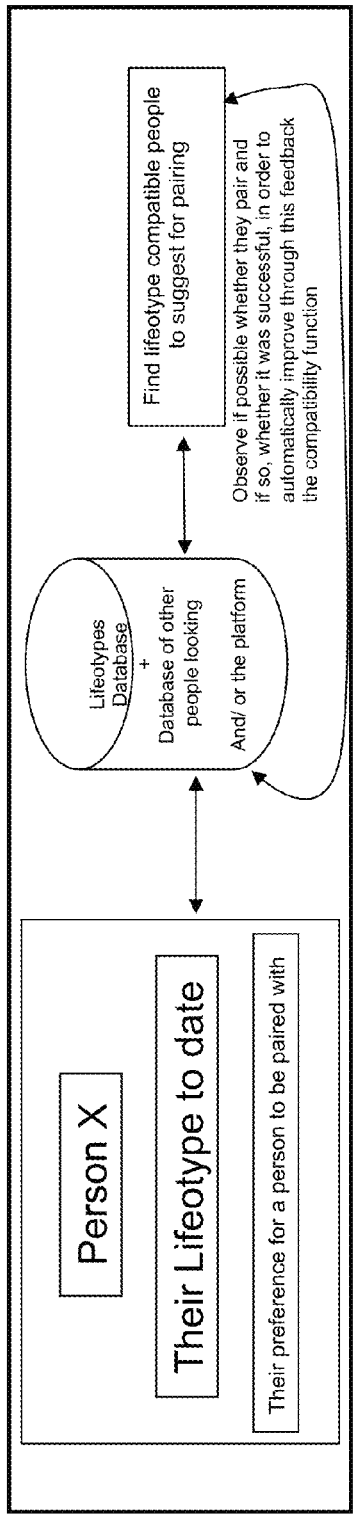
FIGS. 27A and 27B depict a particular embodiment of lifeotype information being used for compatibility analysis.
Figure 27B:
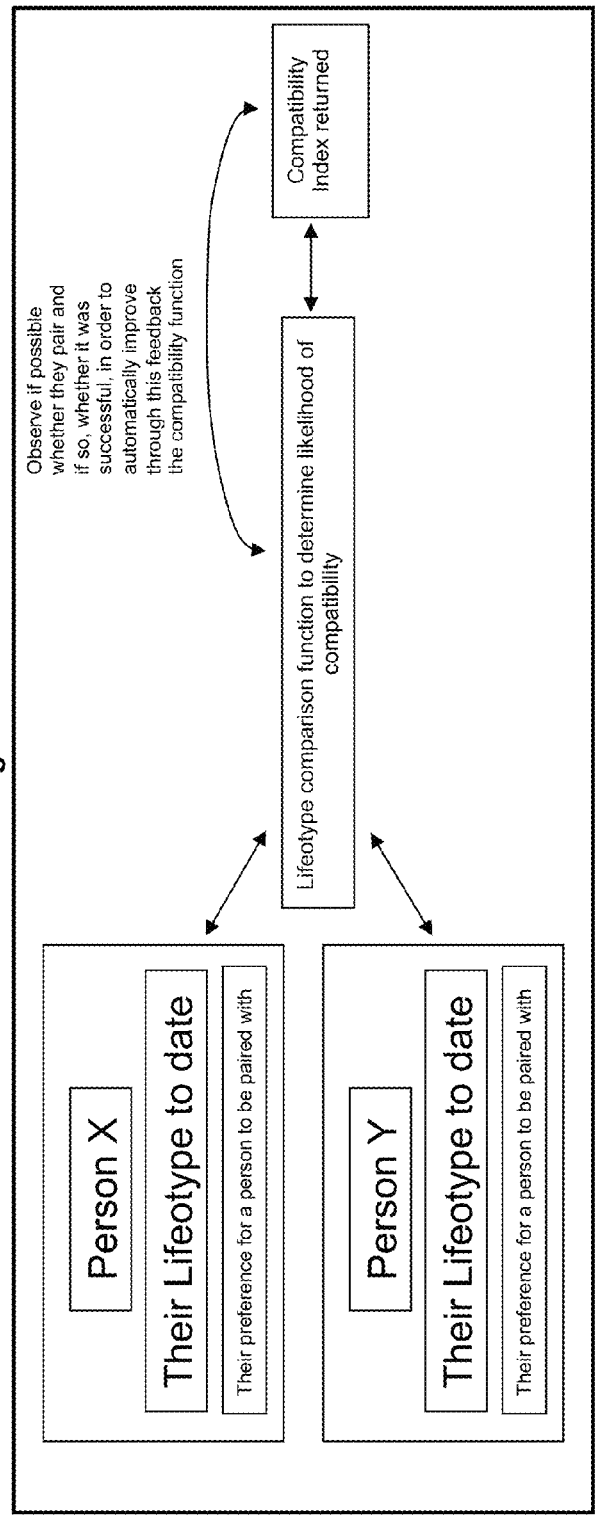
Figure 28A:
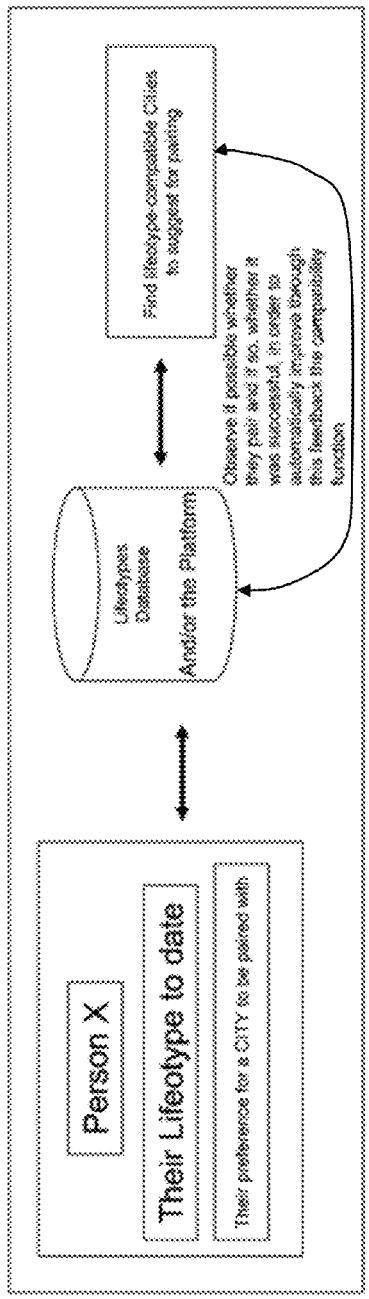
FIGS. 28A and 28B depict a particular embodiment of lifeotype information being used for compatibility analysis.
Figure 28B:
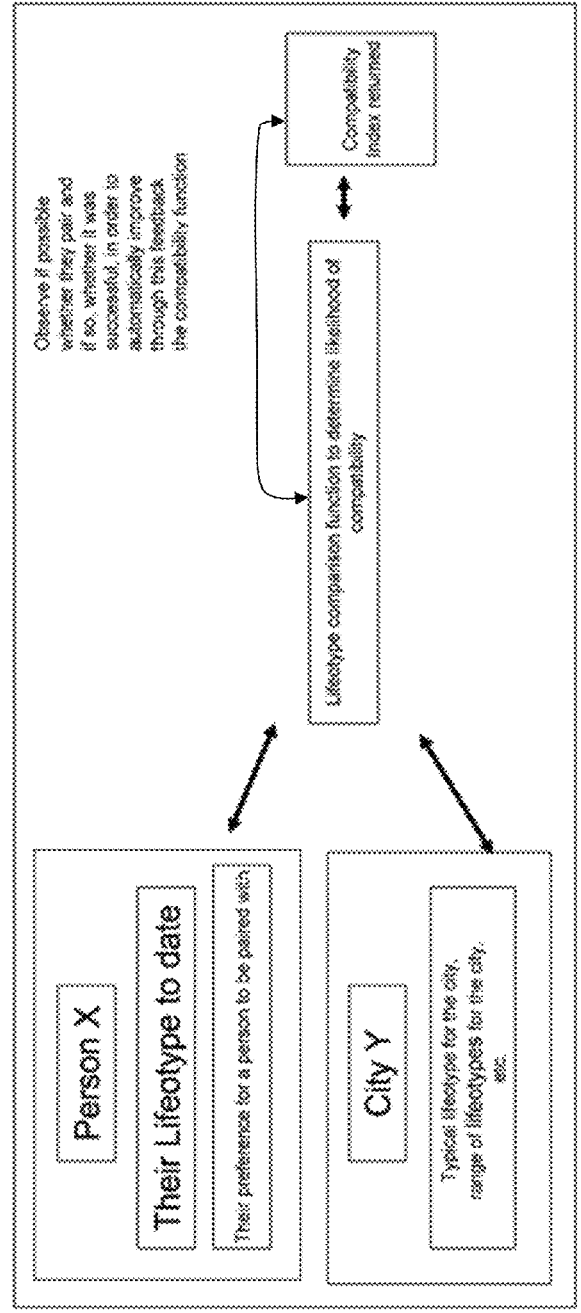

The platform may be used for social and social networking applications. In an embodiment, referring to FIG. 27A-27B, life bits, life bytes, lifeotypes and/or related information may be used for match making. A dating website or company may match people based on life bits, life bytes, lifeotypes and/or related information. For example, a person who goes to bed at 8 pm and wakes at 5 am is likely not to be compatible with someone who goes to be at 2 am regularly. In another embodiment, referring to FIGS. 28A-28B, the platform may determine a user's probability of locating a person with a particular lifeotype or range of lifeotypes in a particular location, such as a particular bar, neighborhood, city or country. For example, a dating website or business may use the platform, life bits, life bytes, lifeotypes and/or related information to assess whether a particular city has compatible lifeotypes for a particular person and if so in what quantities. This determination may be used to informing vacationing and relocation decisions. For example, the person may want to vacation in an area in which she has a high chance of meeting someone with a compatible lifeotype.

In an embodiment, a healthcare professional may summarize, or provide information, including life bits, life bytes, lifeotypes and/or related information, relating to, the types of patients she typically sees or the types of patients she is good at seeing. This information may be aggregated with information obtained from patients, such as ratings, reviews, life bits, life bytes, lifeotypes and/or related information. The platform may enable a user, such as a patient, to choose a healthcare provider based on this information. In an embodiment, the platform may allow a patient to choose or recommend to a patient a certain healthcare provider that is good at treating people with the same lifeotype as the patient. The healthcare provider may be any of the healthcare providers described herein, including a doctor, nurse, pharmacist, physical therapist, weight management specialist and the like. The healthcare professional may also be a more general service provider such as a personal trainer, yoga instructor or the like. In another embodiment, the healthcare professional may be a an institution or organization, such as a hospital, university, health maintenance organization, dentist office and the like.

In certain embodiments, the platform may enable the study of how certain life bits, life bytes and other information impact and/or effect the evolution of lifeotypes. This information may be used to impact or affect lifeotypes. In an embodiment, the impact of a particular television show on a group of lifeotypes over time may be studied. Watching the television show may form a segment of life byte information. The show may be a program about weight loss, such as a contest to lose weight named "The Biggest Loser." It may be determined that watching the program aids individuals who are between 10 and 45 pounds overweight with weight loss. It may also be determined that watching the program frustrates people who are more than 60 pounds overweight. This information may be used to affect the relevant life bytes and lifeotypes by showing the program or similar programs to certain groups of people, determined based on life bits, life bytes, lifeotypes and/or related information. The process may be consensual, with each person consenting to participation in the program.

In an embodiment, the relationship between life bits, life bytes, lifeotypes and/or related information and teaching and learning may be determined. Life bits, life bytes, lifeotypes and/or related information along with the relationships to teaching and learning may be used to separate students into groups subject to different teaching techniques to alter the efficacy of the teaching. In an embodiment, life bits, life bytes, lifeotypes and/or related information may be used to alter or optimize a method, system, process, work flow, organizational structure, structure, organization and the like. Life bits, life bytes, lifeotypes and/or related information collected from different people involved in or at different points in the method, system, process, work flow, organizational structure, structure, organization and the like may be used to alter or optimize the method, system, process, work flow, organizational structure, structure, organization and the like. In an embodiment, elderly people and the staff at an assisted living facility may be wearing body monitors. Using the monitors it may be possible to determine when an elderly person soils his or her diaper and this information may be collected and aggregates across all of the elderly people. Using the monitors, or by other means, it may be possible to determine the frequency with which the staff changes the soiled diapers. For example, it may be determined that the staff make rounds to change diapers twice per day. The two patterns may be brought together to assess the typical delay between soiling and changing of a diaper and possibly improve the situation by altering the pattern and reducing the delay.

In an embodiment, life bits, life bytes, lifeotypes and/or related information may be used to tailor the delivery of advertising. For example, a person with a physically fit lifeotype that spends time biking, may have bicycle ads focused at them. In another example, if two women always go walking together they may be good candidates for a women's only gym, such as Curves. In an embodiment, life bits, life bytes, lifeotypes and/or related information may be used for career counseling. Life bits, life bytes, lifeotypes and/or related information may be collected in relation to various jobs and careers. Information concerning the satisfaction, ability, performance, happiness and the like of people in certain professions may be collected and linked to life bits, life bytes, lifeotypes and/or related information. This information may be used to generate norms or profiles of certain profession and lifeotypes pairs or groupings which may be used for career counseling. In an embodiment, the platform may allow a user to determine which job she should accept in order to maximize her happiness and productivity.

In embodiments, life bits, life bytes, lifeotypes and/or related information may be used to model or study transmission of certain diseases and conditions. In an particular embodiment, life bits, life bytes, lifeotypes and/or related information from many people in a particular area may be used to build more detailed models of the transmission of particular disease or condition whose onset is detectable in the life bits, life bytes, lifeotypes and/or related information of the people. The disease or condition may be a cold, flu, infection or the like.

In embodiments, lifeotype information may be used for recruiting. In an embodiment, a company may determine use life bits, life bytes, lifeotypes and/or related information to determine that people with certain lifeotypes function better at the company and may use this information to inform hiring decisions. In embodiments, a company may use life bits, life bytes, lifeotypes and/or related information to build models of the kinds of lifeotypes that seem to drive retention and success at work in order to try to promote those lifeotypes in the company. For example, if it turns out that people who sleep more than 8 hours per day tend not to ever be promoted at a particular company, but those who sleep less than 6 hours per night tend to burn out and quit, and those who fall in the middle stay at the company 90% of the time from year to year and the promotion rate is 35% from year to year, then the company may suggest or require time in bed to be changed from 7 to 9 hours to 6 to 8 hours. In embodiments, life bits, life bytes, lifeotypes and/or related information may be used to monitor and affect morale in a workplace, school, military environment, prison or the like.

Referring to FIGS. 14 through 17, lifeotypes may be identified and analyzed in a variety of ways. The Platform may identify, generate and create lifeotypes. The analysis layer may identify, generate and create lifeotypes. The following techniques may be used to identify and analyze lifeotypes: iterative optimization, genetic programming, stochastic simulations, model generation and model use (including dynamic probabilistic networks), simulated annealing, Markov methods, reinforcement learning, partial programming, stochastic beam search, model based search, goal-based search, goal-based methods, feedback loops and artificial intelligence. The Platform and/or analysis layer may learn. The Platform and/or the analysis layer may determine the number of life bits and life bytes to include in a lifeotype. This determination may be based on many factors, such as user selection, optimization of data processing or the number of traits required to obtain uniqueness. Feedback loops may identify additional life bits and life bytes, or recommendations for new life bits and life bytes to seek data in connection with. The processes involved may be dynamic.

Identifying lifeotypes may involve identifying parameters that may be sensed. This may largely be determined by what is available. Identifying lifeotypes may involve identifying parameters that may be derived. This will be determined at least in part by what is useful for other applications. Identifying lifeotypes may involve identifying patterns in the derived data. In an embodiment, the pattern may be many nights of low sleep as a pattern of "prolonged sleep deprivation." In an embodiment, the pattern may be many exercise events per week being called an "active person." In an embodiment, the pattern may be more than 4 hours of exercise per day being identified as an "exercise bulimic." In an embodiment, the steps for identifying lifeotypes may involve identifying what is it about the world that is desired to be understood or predicted. For example, information concerning prolonged sleep deprivation. The next step may be determining if there are patterns in the derived data that can be discovered through human intervention and description, automatic discovery by a computer or both. The relationship of the patterns in the derived data to the topic to be understood may then be assessed. If there is a strong relationship the analysis may be sufficient. If there is not a strong relationship, the analysis may involve determining if there are new derivable parameters that would be of assistance. If the data is available these parameters may be added and the steps repeated. If this data is not available it may be requested or surrogates may be identified. If this can not be done or the raw data is not available, then the question may be asked "what could be added to the raw data pool (i.e. what new parameters could be directly sensed or calculated or gathered in some way) such that the analysis can be performed? If such a set of new raw values in would help and could be gathered then either add them or do what it takes (i.e. adding the sensors to new body monitors) so that at some point in the future the data will have these new values and the process can be repeated.

In an embodiment, lifeotypes may be created, identified, discovered and the like by a lifeotype discovery module. The lifeotype discovery module may utilize a novelty detector, for example, in the domain where physiological data is collected and a large body of such data exists for many individuals. Any variable that, for some subset of individuals, is statistically outside the norms for the population could be of interest. In an embodiment, for a large dataset, an infinite number of features may be defined of varying complexity. This continuum can be thought of as starting with single variable reports about an individual (e.g. their average daily physical activity is low) to relative measures (e.g. their average daily physical activity is low for their age) to complex pattern based interactions (e.g. their daily physical activity after a night of poor sleep is high for their age). The Platform may determine which lifeotypes have utility. In one embodiment, the lifeotypes selected may be those that have some predictive power with respect to other lifeotypes, as determined by an analysis module.

In an embodiment, feature discovery may proceed by starting with the simplest single variable features (e.g. total values per day of sleep, energy expenditure, or physical activity and the like) and examining whether statistically significant relationships exist to other measures of interest (e.g. health outcomes, disease states, weight loss, stress level, and the like). The user may set up these different classes of lifeotypes (e.g. input and output) or the Platform may try all pairs. In this example, only features that are sufficiently strongly correlated would become true or saved lifeotypes. Another embodiment would utilize a random walk across pattern space (instead of using an ordered list), utilizing techniques from the stochastic beam search literature, evolutionary computation, simulated annealing, Markov Chain, Monte Carlo and the like. The invention machine, in one embodiment, can be constantly searching over the database to find relationships between patterns and outcomes that exceed a given statistical level. A related embodiment allows the human users of the system to "prime" certain patterns to be tested for first and/or serve as starting points for the search.

The Platform, analysis layer, sensors, systems and methods may be calibrated, such as by using algorithm to improve another. In an embodiment, a GSR measurement can be used to more correctly interpret a heart rate measurement. As a result, even in the absence of the GSR measurement, based on the past GSR data, a more accurate heart rate measurement may be obtained. This process may also allow for calibration of slow changes in a user over time. For example, a user may wear more clothing in the winter than in the summer. Calibration may be done through the use of a training pack and/or calibration pack. The training and/or calibration pack may be a component of an item of fitness equipment. In an embodiment, the training pack may contain sensors which may measure heart rate. The data collected by the heart rate sensors may be used to calibrate the algorithm used to determine energy expenditure from other sensors. The heart rate sensors may be more sensitive and a correction algorithm may update or calibrate the determination of energy expenditure. In an embodiment, a location pack may provide location and other contextual information, such as, in the car, in the wearer's home gym, and the like. The location and contextual data can be used to calibrate the determination of energy expenditure. Contextual data may also be used to inform or adjust measurements and/or algorithms. A marker may be used for calibration.

The Platform and/or analysis layer may analyze and process lifeotypes and related data. The Platform and/or analysis layer may identify lifeotype patterns and/or correlations across different populations, sub-populations, groups or sub-groups or across different lifeotypes, life bits and life bytes. The correlations may be overtime. The Platform and/or analysis layer may classify a population by sex, sexual orientation, race, ethnicity, culture, age, conditions, geographic region, medical conditions, activity levels, participants in a certain game or sport and the like. The Platform and/or analysis layer may identify relevant lifeotypes, life bits, life bytes, parameters, other data and the like. In an embodiment, the Platform and/or analysis layer may identify sub-populations in disparate sections of the world which share certain lifeotypes. For example, people in Helsinki and those in a mountain valley region in California may share certain lifeotypes, life bits and life bytes as they both live in a cloudy climate.

The Platform and/or analysis layer may identify pattern-inference pairs or groups. In an embodiment, the Platform and/or analysis layer may identify that a person who does X dies within Y or a person who does activity V is likely to contract condition W. The pattern-interference pairs may take into account time and/or geography. The Platform may allow for predictions of the future or identification and extension of trends. The Platform may allow a user to determine how making a change in the past would affect a current situation. The Platform and/or analysis layer may allow for self-testing. Platform and/or analysis layer may predict future outcomes for an individual and show likely default outcomes given current lifeotype expression. The Platform and/or analysis layer may allow what-if testing. The Platform and/or analysis layer may utilize probabilities in the prediction of the future. For example, stopping smoking decreases chances of throat cancer and increases the chances of short-term stress.

The Platform and/or analysis layer may generate many correlations, conclusions, results, pairs and the like and create a database of them which may be analyzed by the Platform and/or the analysis layer. The Platform and/or analysis layer may publish reports and suggest future studies. Platform and/or analysis layer may make recommendations. The Platform and/or analysis layer may generate treatment programs. The Platform and/or analysis layer may generate sub-populations or sub-groups for certain purposes. The Platform and/or analysis layer may derive data. The Platform and/or analysis layer may utilize iterative optimization. The Platform and/or analysis layer may utilize genetic programming. The Platform and/or analysis layer may utilize feedback loops. The Platform and/or analysis layer may utilize cycling back. The Platform and/or analysis layer may utilize artificial intelligence. The Platform and/or analysis layer may actively search for more information. The Platform and/or analysis layer may make requests of its users. In an embodiment the Platform and/or analysis layer may ask a user to provide three more blood samples.

The Platform and/or analysis layer may be mined as an invention machine. The Platform and/or analysis layer may utilize the concepts of an invention machine, such as by being a goal-driven iterative engine searching for solutions. The Platform and/or analysis layer may identify trends in lifeotypes and in information accessed or provided to users. The Platform and/or analysis layer may use a loop to identify additional life bits and life bytes, or recommendations for new life bits and life bytes to seek data in connection with. The Platform and/or analysis layer may discover new life bits, life bytes, derived data, surrogates and the like. The Platform and/or analysis layer may be used for predicting. In an embodiment the Platform and/or analysis layer may be used to predict the success of research programs, success of projects, success of business initiatives, future disease states, stocks to buy and the like. The Platform and/or analysis layer may be used for guided information gathering. Further, the Platform will reveal new types of information that allow for the creation of particular assessment times and protocols. For instance, it may be determined that viewing the continuous sensed data of an individual for 15 minutes upon waking will give insight into whether that person is at risk for heart disease. In this way, the Platform can make specific predictions about individuals from specific sources and types of data, which the Platform itself has determined to be optimal.

In an embodiment, the analysis may include identifying high value lifeotypes. The Platform may examine a library of lifeotypes as a model of the world with probabilistic outcomes and perform behavior learning using any of a number of techniques to produce an optimal strategy to obtain a desired outcome. As an example, for a particular individual (say, a 35-year old smoker who also exercises vigorously three times a week and eats poorly), the system may analyze the\particular lifeotype and determine that the most useful (and likely to be successful) strategy would be to cut back on smoking by 50% and eat better, rather than quitting smoking entirely. The system may determine this by considering many different action-strategies, using the stored data to simulate the effects, and searching over the action space to find an optimal policy. Reinforcement learning and the class of program search strategies may also allow the solution of this behavior optimization strategy.

Lifeotypes may be based on relative measures. There may be relative lifeotypes, relative life bytes and relative life bits. Changes from a baseline or norm may be recorded in connection with a relative lifeotype, relative life byte and/or relative life bit. Lifeotypes, including relative lifeotypes, may map to a diagnostic measure, such as non-invasive glucose, pulse pressure from heat flux, skin temp, galvanic skin response and the like. The Platform may assist with understanding the lifeotype associated with a particular life byte sequence, set of life bytes and/or set of life bits. The Platform may also assist with determining the life byte sequence, set of life bytes and/or set of life bits associated with a particular lifeotype. This process may be analogous in certain respects to the protein folding problem. The Platform and/or analysis layer may utilize successive measures (e.g. one week recordings 4 times a year) to detect early the signs of a disease, such as heart disease. Coaching and/or human input may be part of the analysis. The Platform and/or analysis layer may view or provide views of slices and/or aggregations of the data. This may generate automatic and accurate population models. The Platform and/or analysis layer may utilize and/or contain databases, disk-based databases, distributed databases, store and forward databases, peer to peer databases and the like.

Many different types of users or groups of users may use the Platform and/or lifeotypes and related concepts. These users or groups of users may be consumers of the Platform and/or lifeotypes and related information. A user may be a medical or scientific user, such as a scientist, researcher, doctor, healthcare professional, healthcare worker, caregiver, academic, educational institution, institution, hospital, other healthcare facilities, patient, an infant, a child, an adolescent, an adult, an elderly person and the like.

A user may be a lifestyle user, such as an athlete, personal trainer, gym, fitness club, sports team, youth group and the like. A user may be an entertainment user, such as a gamer, celebrity, fan and the like. A user may be a business user, such as a marketer, advertiser, insurer, actuary, personnel in a health maintenance organization, data business, enterprise software business, financial services business, security business, investment industry business, an administrative user and the like. A user may be someone who is curious. A user may be a policy maker, public health official, epidemiologist, government and the like. A user may be the World Health Organization, National Institutes of Health and the like. A user may be a consumer, employer, workplace, employee and the like. A user may be a community, social network and the like. A user may also be an entity, such as a company, or a computer system, such as a computer system that is making use of the Platform. A user may be a system or method that is making use of the Platform and/or lifeotypes or related information.

The Platform may be applied in many ways including for medical applications, filtering data, publishing, report generation, policy making, insurance-related applications, search, self-assessment, entertainment, applications relating to interactive spaces, novelty, controlling a device, operating a device, controlling a third parameter, monitoring a workplace, security, marketing, advertising, human resources, military uses, law enforcement, first responders, sports recruiting, analytics, consulting, reviews, content presentation, data integration, data sales, reporting, concierge services, registries, royalty systems, artificial intelligence, sales, product design, therapy, advice, predictions, coaching, comparisons, financial applications, e-commerce, voting, politics, crime scene investigation, forensics, identifying related persons, clinic trials, tagging and the like. In discussing the application of the Platform, the term lifeotype may also include lifebits, lifebytes and/or lifebyte sequences. Any of the applications of the Platform may be implemented as a system, method, apparatus, application and/or service.

The Platform may be utilized for medical applications, such as medical monitoring. In an embodiment, the Platform may be used to monitor patients. The patients in an emergency room or in the waiting room of the emergency room may be outfitted with wearable monitors. Using the monitors, various lifeotypes of the patients can be ascertained. This information may be used for treatment. Healthcare providers can also monitor changes in the lifeotypes of patients and treat them before they crash. Using the Platform and lifeotype information a healthcare provider may be able to predict when a patient is going to crash and treat the patient before that time. The Platform may be integrated with existing monitoring systems in the emergency room and display lifeotype, life bits, life bytes and lifestyle data along side traditional monitoring systems. The Platform may be used in triage situations. Dynamic or low resolutions lifeotypes, as discussed herein, may be more relevant in medical emergency or triage conditions. In an embodiment, the monitoring method may involve determining a condition of a body, comprising continuously measuring the pulse of the body; continuously measuring the heat flux from the body; inferring from the measurements of the pulse and the heat flux the nature of an activity of the body; and delivering information about the condition of the body that depends on the nature of the activity. In an embodiment, the monitoring may be in connection with a monitoring device, such as a sensor device, metabolic halter and the like. The data may be provided to a healthcare professional who may use the data in connection with a patent appointment, such as for a physical. In an embodiment, the data may include data regarding energy expenditure, glucose levels and the like. In an embodiment, the data may be used in connection with monitoring and managing diabetes.

In an embodiment, the monitoring may be in connection with a medical trial, such as a pharmaceutical trial or the like. The monitoring may facilitate the collection of data and may result in the collection of a wider and deeper range of data and data that is more objective than data obtained by traditional means. The monitoring device may measure metabolism and data concerning metabolic rate changes may be collected. In another example, the monitoring device may measure energy expenditure, heart rate and galvanic skin response and also included a glucometer and accelerometer. The sensors may be non-invasive. The data may be used in connection with diabetes and an algorithm may determine relative levels of glucose based on the data. The glucose levels may be compared to energy expenditure levels to detect any inconsistencies. The data may be collected over time. The result may be the ability to track relative levels of glucose and alert an individual when necessary. In an embodiment, the systems and methods may be used in an intensive care unit to track VO2 and energy expenditure. In an embodiment, the systems and method may be used to assess whether patients are receiving adequate nutrients. For example, the systems and methods may be used to assess whether patients in a hospital are being over or under fed. In an embodiment, the systems and methods may be used in connection with heart transplant patients to measure the strength of the heart overtime. In an embodiment the systems and methods may be used to measure energy expenditure in connection with fiber maloma or fibromyalgia. In an embodiment, the systems and methods may be used to monitor or control drug delivery. In an embodiment, energy expenditure and another parameter may be used to solve for a missing parameter or assess an inverse relationship on measured parameters. For example, energy expenditure and weight may be used to solve for glucose and heart rate. In another example, with hypertension, a marker and energy expenditure, the systems and methods may be able to determine blood pressure. In embodiments, the systems and methods may adapt, self-calibrate, calibrate based on past data, learn over time, reinforce learning and the like.

In an embodiment, the Platform may facilitate determining an inverse, causation and/or cumulative relationship. In an example, a person it may be determined that a person who has not slept in 36 hours and has not eaten in 10 hours, is likely to be fatigued. A cumulative condition may be a condition where an individual's condition may be deduced from the individual's behavior over some previous period of time. In an embodiment, techniques for determining an inverse, causation and/or cumulative relationship may be used by first-responders (e.g. firefighters, police, soldiers and the like). In an example, the wearer of a sensor device may be subject to extreme conditions and if heat flux is too low for too long but skin temperature continues to rise, the wearer is likely to be in danger. In another embodiment, the inverse, causation and/or cumulative relationship may be determining why a baby is crying. The factors that may be considered include temperature, heart rate, orientation, activity type, state of sleep, crying and the like. In another embodiment, the inverse, causation and/or cumulative relationship may be determining why a patient, such as a patient in an assisted living environment, is not getting well. In another embodiment, the inverse, causation and/or cumulative relationship may be determining why a person in an emergency room is crashing. Factors that may be considered include sensor data, data from at least a two sensor array, hunger, temperature, fatigue and the like.

In a detailed embodiment, the Platform may be used to monitor certain parameters in connection with diabetes. The Platform may monitor energy level and determine glucose levels and provide guidance. The Platform may advise the patient, a doctor, healthcare provider or the like to adjust an insulin pump or to modify energy expenditure via lifestyle changes. The Platform may also consider markers, such as markers relevant to type I diabetes, markers relevant to type II diabetes, genetic markers and the like. The Platform may also monitor weight, cardiac status, vascular effects, perfusion to periphery (such as feet), profusion of small blood vessels and the like. The Platform may also monitor surrogate measure or derive new surrogate measures. The Platform may optimize inputs and outputs, such as by considering time related factors.

The Platform may be utilized for medical decision making. In an embodiment, the Platform may be used to inform decisions regarding treatment. Medical decisions can be based in whole or in part on lifeotypes and related data. The Platform may allow a user to plot lifeotypes against intraventions. Lifeotypes and related data can be used to assist medical professionals and patients with treatment choice. The Platform may enable identification of prior patients with similar lifeotypes and may enable review of the decision trees for those patients. In an embodiment, the Platform may track the decision tree of a particular patient. In this regard, the Platform may help to predict the outcome and likely effects of a treatment plan. The process may be automated and the Platform may derive the advice. Using the Platform a patient may be able to determine which healthcare provider has the most successful treatment and/or rehabilitation record for the patient's lifeotype. Using the Platform the patient may be able to obtain user ratings from other patients.

The Platform may be utilized for medical studies and/or diagnosis. The Platform may be used to better delineate known diseases, conditions and syndromes and to identify new diseases, conditions and syndromes. The Platform may be used to identify new treatments. The Platform may be used for therapy. The Platform may be used to identify groups or cohorts for therapy based on lifeotype. Support groups or clinical trial cohorts may be created based on lifeotype. A patient may be paired or grouped with other individuals who have or are dealing with similar issues or are in a similar state of health. A patient may be paired or grouped with other individuals who have survived a particular condition or disease or who have improved their condition. A user may connect with others or review their data to determine what they did to achieve a particular goal. The Platform may analyze and predict the likelihood that the therapy or treatment will work for another, using lifeotype data.

The Platform may be used to determine the efficiency of medical providers. The Platform may be used to determine the efficiency of a particular healthcare professional or of a department or functional unit, such as an emergency room, nursing station, intensive care unit, laboratory, neonatal ward and the like. The Platform may be used to determine and track the success rates and patient ratings of a particular medical provider. The Platform may be used to track treatment success and patient ratings in general. The Platform may be used to deliver content based on lifeotypes and related information. In an embodiment, a patient may be provided with personalized healthcare content based on lifeotype and related data. In another embodiment, a search may be customized based on lifeotype data. The Platform may allow for the creation of content in real time. The Platform may generate blogs based on lifeotypes and related data. As discussed below, the content may be advertising.

The Platform may be utilized for disease management. The Platform may perform lifeotype-based risk calculation in disease management to prevent or manage a disease, such as heart disease. The Platform may be used for drug titration. The Platform may, or enable a user to, preemptively identify disease treatment and prescribe treatment. In an embodiment, a person may have a hypertension-related lifeotype. The Platform may determine that exercise may benefit this person based on the lifeotype information. The Platform may provide personalized feedback to the person. The Platform may generate a report. The Platform may assist with modifying the behavior of the person. The Platform may generate a program guide and/or provide a program guide to the person. Based on exercise and nutrition, the Platform may predict blood pressure, disease state, severity or changes in any of the foregoing. The relationship may be cause and effect or inverse/reverse diagnosis. A hypertension marker may serve as a calibrator. Lifeotype information may be used to inform drug delivery. The Platform may be applied to wellness, health, diagnosis, condition management and the like.

With respect to choosing drugs and dosages, the data described herein and changes to that data including lifeotype data could be used in much the same way as a persons genetic profile is used in pharmacogenomics. For example, an individual could be assessed with the systems and devices described herein one time, or at intervals to determine the correct dosage.

In an embodiment, the Platform may be used in connection with the diagnosis of heart disease by providing a wearable body monitor disposable on the upper arm of a patient; deriving electrocardiogram from sensors associated with the wearable body monitor; comparing the electrocardiogram with at least one electrocardiogram of a member of a healthy population; and based on the comparison, making an assessment as to the probability that the patient has heart disease. In an embodiment, the Platform may be used in connection with managing stress by providing a wearable body monitor having at least two sensors for sensing conditions of the body; and deriving an indicator of stress from the data streams of the two sensors.

In an embodiment, the Platform may be used in connection with supporting care giving by providing a person with a wearable body monitor, the monitor including a plurality of sensors for sensing conditions of the person's body; automatically inferring the nature of the activity of the person from the output of the plurality sensors; and providing a caregiver for the person with information about the activity. In an embodiment, the Platform may be used in connection with therapeutic methods by inferring a condition of the wearer of a wearable body monitor from the output of a plurality of sensors that are associated with the wearable body monitor; and based on the inferred condition, recommending a time for the administration of a therapy that is related to the inferred condition.

In an embodiment, the Platform may be used in connection with patches and disposable sensors that may both sense body conditions and, in a closed loop, possibly without human intervention, administer a therapy which may change the body's state. In an embodiment, the Platform may be used in connection with an apparatus worn against the body with at least one sensor, a processor, that senses the presence of a headache, and that may administer a pain-relief medication through the skin. The determination to administer the medication, determination of the dose and the like may consider lifeotype information. In an embodiment, the Platform may be used in connection with an apparatus worn against the body with at least one sensor, a processor that senses the imminence of panic-attack, and that administers a claming agent through the skin. The determination to administer the agent, determination of the dose and the like may consider lifeotype information. In an embodiment, the Platform may be used in connection with an apparatus worn against the body with at least one sensor, a processor that senses the presence of stress and that administers a tactile reminder to promote bio-feedback for stress reduction. The determination to administer the feedback, determination of the duration and intensity of the feedback and the like may consider lifeotype information. In an embodiment, the Platform may be used in connection with an apparatus worn against the body with at least one sensor, a processor that senses the presence of a heart attack or stroke and that administers a blood thinning medication through the skin. The determination to administer the medication, determination of the dose and the like may consider lifeotype information.

In an embodiment, a marker may be used in connection with the Platform for medical applications. The marker may be a marker related to the risk of lung cancer, such as consuming vegetables. The marker may be related to certain proteins and indicate information regarding exercise, diabetes, bone density and the like. The marker may be a genetic marker. The marker may take into account environmental factors. In an embodiment, a relevant marker may be identified and an individual may be provided with a monitor. The monitor may collect information relevant to the marker. The monitor may assist with administration of a program or regime. The monitor may assess compliance and adjust variables based on the level of compliance. The data collected by the monitor may be provided to a healthcare professional. The healthcare professional may use the data in connection with a physical. The data may indicate a reduction in a condition. The data may be used to provide feedback or to calibrate the system. The system and method may be used in connection with various conditions, such as diabetes, obesity and the like. In the aggregate the system and method may function as a health census for a population, group or nation and the like.

The Platform may include or function as a data filter. The Platform may enable data to be sorted or viewed based on lifeotypes and related data. Using the Platform, it may be possible to obtain validated results in a particular space for a particular lifeotype, even though that space was not tested directly. In an embodiment, a study on one topic may have had many results relevant to another topic, which is now relevant for another purpose. Using the Platform, the data can be sorted and viewed based on the other topic (with controls if necessary) and conclusions may be drawn about that topic. The Platform may facilitate auto-generation of control groups and datasets for appropriate cross-validation. Using the Platform, it may be possible to identify, based on lifeotype information, data sets that are a subset or cross section of another data set obtained for a different purpose, that may be relevant to other studies.

Figure 29A:
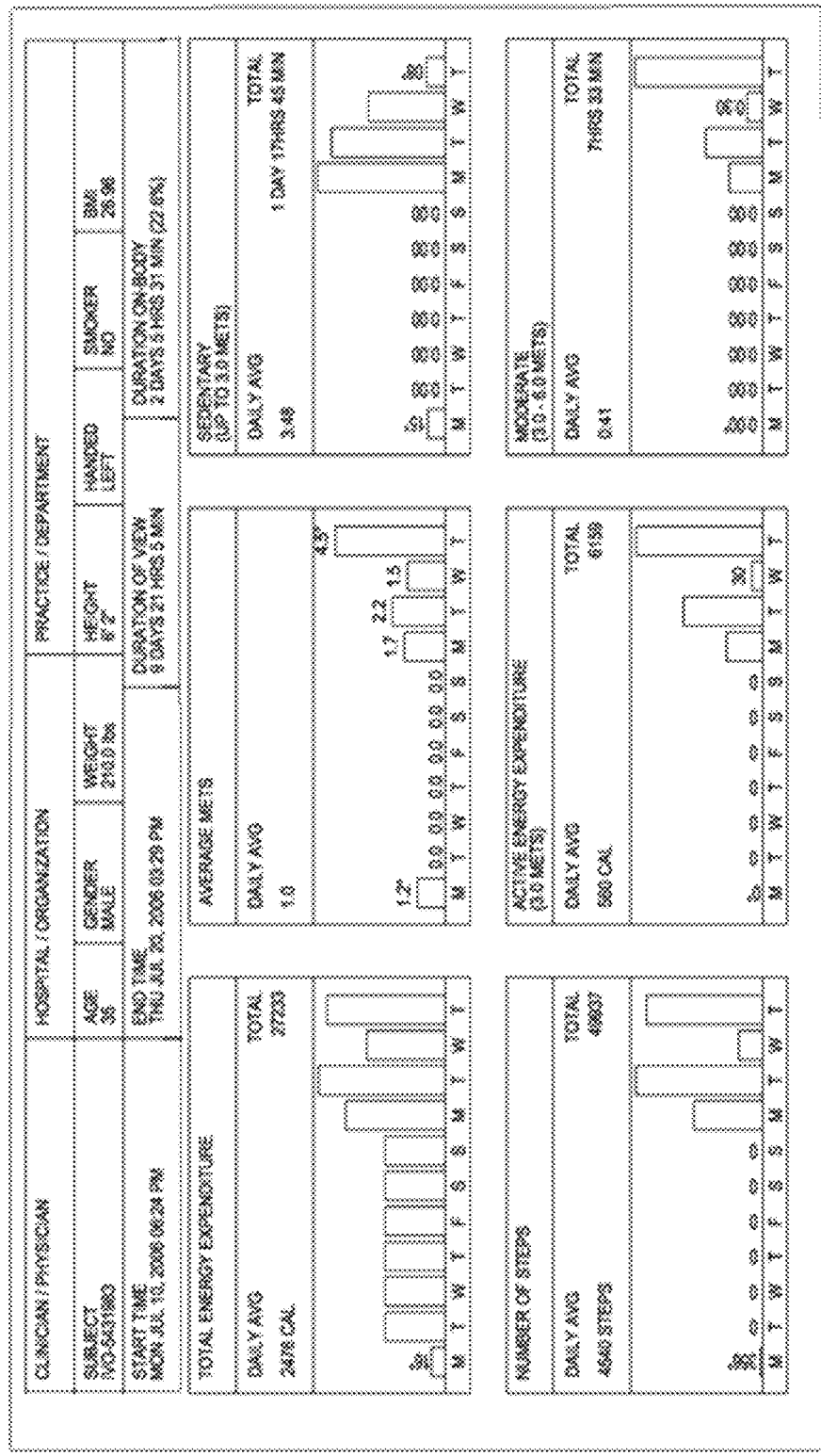
FIGS. 29A and 29B depict a particular embodiment of a report.
Figure 29B:
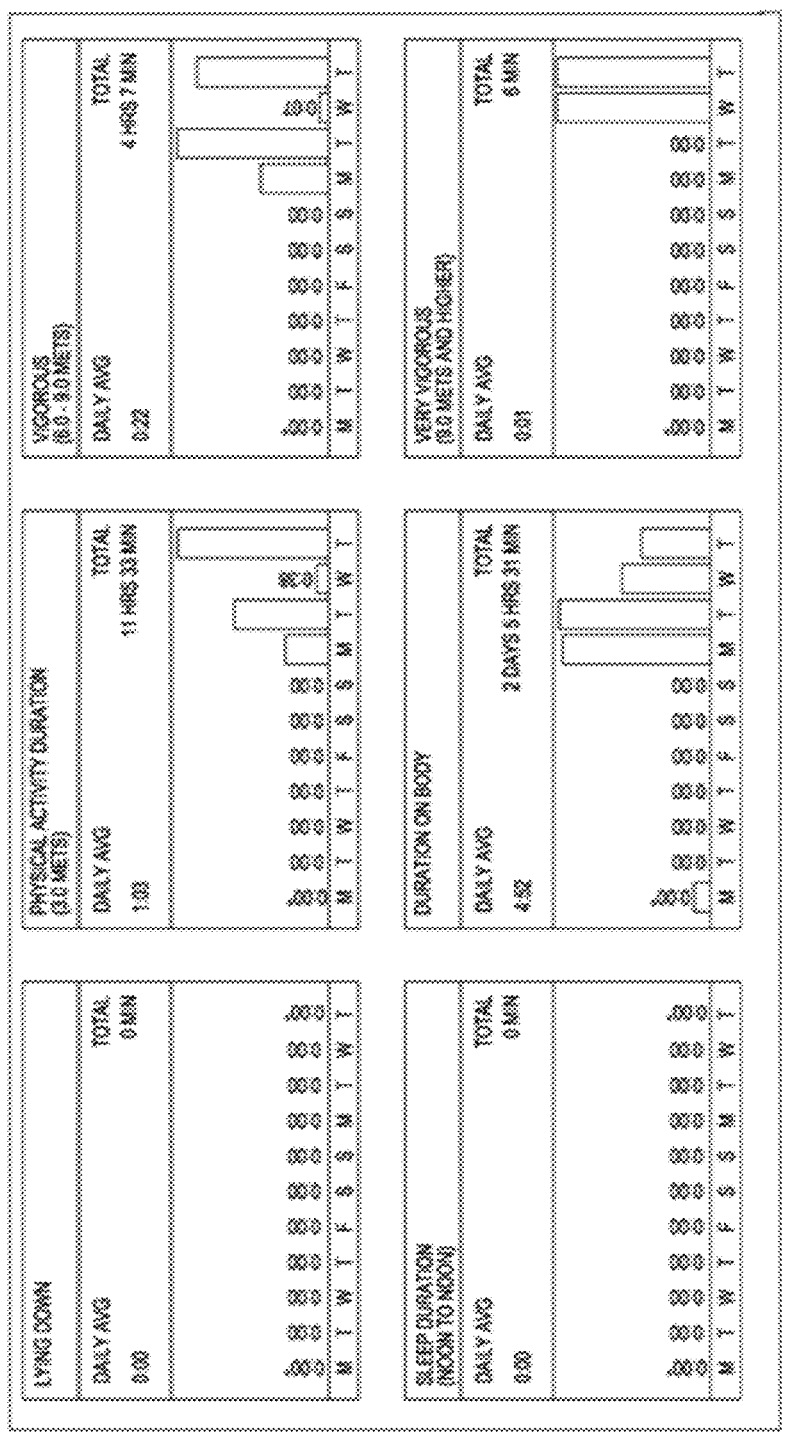

The Platform may be utilized for publishing. In an embodiment, the Platform may auto-publish material based on lifeotypes. The material may be reports, results, outcomes, studies and the like. In an embodiment, a report may be of the form of FIGS. 29A-29B. In an embodiment, the Platform may auto-complete forms, such as medical records, insurance forms and the like. The Platform may publish to a doctor, patient, family, employer, insurer and the like. The Platform may suggest a revised treatment or decision pattern. The Platform may include a publishing engine, which may auto-publish material. The publishing engine may make the determination to publish based on set parameters. In an embodiment, a patient may ask a question and if the results are interesting enough then the application may publish the response, such as in the form of a scientific paper, on the internet, making it available to other people. In an embodiment, the publication engine may publish material in the following scenario: if 80% of patients with a particular lifeotype choose option A, and 20% of patients with the same lifeotype choose option B, but option B actually produces better results. The publishing rule may be that when the outcome is counter intuitive, the publishing engine is to publish a paper automatically, provided that all correlations are above 0.9 and the sample size is 1000 or more people. The Platform and/or publication engine may utilize correlations, aggregation and statistics. The Platform and/or publication engine may personalize healthcare content based on lifeotype and related data. The Platform and/or publication engine may customize a search for a website based on lifeotype data. The Platform and/or publication engine may create blogs based on lifeotype and related data. The Platform and/or publication engine may create a spatial map of lifeotypes, which may be tied to location, emotions and other information.

The Platform may be utilized for policy making. In embodiments, the Platform may be used to study problems and issues with a healthcare system, such as a country, state or provincial healthcare system. The Platform may be used to assist policy makers spending healthcare budgets. The Platform may assist with determination of where to spend insurance money. The Platform may be utilized for insurance-related applications. Actuarial tables, probability tables and mortality tables may be based on lifeotypes. The Platform may be used in connection with insurance sales. In embodiments, the Platform may assist with underwriting insurance policies based on lifeotypes. The Platform may assist with the determination of where to spend insurance money based on lifeotypes. Using the Platform, lifeotypes may be used to affect underwriting, insurance pricing, annuity pricing, pricing of defined benefit plans, benefits, determination of coverage, identification of pre-existing conditions and the like. The Platform may form a part of a service of associating lifeotypes with overall life expectancy or with insured conditions.

The Platform may be utilized in connection with a search function. Lifeotypes may be used to filter, order and/or cluster search results. The search function may present content based on lifeotypes. The search function may be based on a page rank style analysis of link structures based on lifeotypes. The search functionality may be a search engine which may account for lifeotype.

The Platform may be utilized for self-assessment. In an embodiment, the Platform may recommend dietary decisions. The Platform may allow a user to review the success of different dietary plans for individuals with similar lifeotypes. The Platform may allow a user to compare the user's own results on different plans. The Platform may allow a user to track what is working for the user and for others based on lifeotype. The Platform may allow for consideration of an Atkins diet and may consider data from a BodyBugg device. The Platform may allow a user to monitor food intake and/or nutrition and assess effects based on lifeotype. The Platform may allow a user to monitor fitness and/or lifestyle choices and assess effects based on lifeotype. The Platform may enable behavior modification based on lifeotype. The Platform may assist a user in training for a goal. The Platform may affect or maximize a user's success with respect to any project. In an embodiment, the Platform may assist a user with a dietary regimen by deriving an indication of a calories consumed from the output of a wearable sensing device that includes a pulse meter and a heat flux meter; and wirelessly sending information about calories consumed to a personal digital assistant of the patient. In an embodiment, the Platform may assess fitness by providing a wearable body monitor having a pulse sensor and a heat flux sensor; deriving an activity type from the outputs of the pulse sensor and the heat flux sensor; and based on the activity type and the outputs, assessing the fitness level of the wearer.

The Platform may be utilized for entertainment-related applications. Social networking may be organized by lifeotype. In an embodiment, a social networking website, such as myspace.com, may present content and facilitate social networking or create groups based on lifeotype. Internet audio and video, such as on Youtube.com or Break.com, may be organized or indexed and/or presented based on lifeotype. Lifeotypes may be used as an index for content, media, entertainment, leisure and the like. The Platform may be used to unite people based on lifeotypes. The Platform may be used for dating applications. Dates may be arranged or introductions may be made based on lifeotype information. The Platform may be used for competition. The Platform may identify groups of competitors based on lifeotypes. The Platform may allow for the operation of a device, such as an entertainment device, based on lifeotype. In certain embodiments, lifeotypes may be used as tags. In other embodiments, tags may be interpreted based on lifeotypes.

The Platform may be used for gaming. In an embodiment, lifeotypes may be used in connection with holodeck type applications. In an embodiment, lifeotypes may be used in connection with massively multiplayer games. A player's character(s) in a game, such as an online, multiplayer or other game, may be affected by the player's lifeotype and actions in the real world. In this way, lifeotypes and related information may restrict, enable or define the character(s). If a player becomes more fit, his character(s) in the game may be able to run faster and jump higher. If a player improves his diet his character(s) may become stronger. If a player's lifeotype changes, similar changes may happen to this character(s) in the game. In an embodiment, the Platform may provide a behavior feedback and/or modification program, with virtual or real coaching, to guide an individual towards his character in a game, such as a video game. The Platform may tailor experiences to a user. In an embodiment, the Platform may tailor the game and/or experience to the user based on lifeotypes and related information. In an embodiment, a user may wear an armband for a week and the system may gather data and calibrate the experience based on the information collected. The Platform may also allow a user to replay experiences of others. In an embodiment, the Platform may also enable the virtual courtship of online-sex-partners. In order to win the affections of someone online, a user may be required to "deserve" them in the real-world. This application may be an extension of an adult friend finder application.

The Platform and lifeotype information may be used for entertainment with interactive spaces as discussed herein. The Platform and lifeotype information may be used for sports-related application. The participants in a sports or gaming league may be chosen based on lifeotypes and related data. The teams for a sport or game may be chosen based on lifeotypes and related data. Other cohorts or groupings may be chosen based on lifeotypes and related data. Lifeotypes and related data may be used to tag entertainment content by lifeotype. Lifeotypes and related data may be used to censor or scale content. In an embodiment, an individual may be shown a less stressful version of a movie as a result of this lifeotype. For example, his lifeotype may be characterized by a weak circulatory system and a pre-disposition toward heart attacks. Content may be delivered based on lifeotypes and related data. Content may be print media, such as books, news and the like, along with online analogs. Content may also be audio, music, video, games, video games, blogs, podcasts, images, art, fine art and the like.

Lifeotypes and related information may be used in connection with or to create interactive spaces. A space may be affected based on the combination of lifeotypes in the space and the proximity of certain lifeotypes. Lifeotypes may function as a filter that affects a certain space or environment. Attributes or features of a space may be modified based on lifeotypes or changes in lifeotypes. Variables of a space which may be modified include brightness, color, volume, sounds, temperature, air quality, pressure, distance between objects (such as furniture), protection from outside, status of entries, status of exits, presence of objects, absence of objects and the like. In an embodiment, the lights in a room or section of a room may be dimmed when a person with a lifeotype including susceptibility to migraines enters the room or section of the room. In another embodiment, the space may be a buffet in a cafeteria. The buffet may re-configure the food offerings to present sugar free food choices to a person with a diabetic lifeotype. In another example, the lights in a space may be dimmed and music may be played or modified if two compatible lifeotypes enter a space. In an embodiment, users may be equipped with stress meters and the space may be a meeting room or auditorium and the Platform may provide feedback to a given user or others in the room.

Lifeotypes and related information may also be used for novelty purposes. In an embodiment celebrity lifeotypes may be offered for sale or used for comparison purposes. Horoscopes may also be based on lifeotypes and related information. In another embodiment, the popularity of lifeotypes may also be presented. A user may be able to see how popular his lifeotype is and may be provided with a list of famous people with the same lifeotype or with compatible or antithetic lifeotypes. Lifeotypes may also be used to impact or control a device or another parameter. In an embodiment, a sensor, processor, computing device or the like may be controlled based on lifeotype. A user may have a lifeotype for which the Platform determines another parameter should be measured and the Platform may turn on another sensor to measure that parameter. In an embodiment, lifeotypes and related information may trigger an event or control of another device.

Lifeotypes and related information may be used for workplace monitoring. A workplace can be monitored or surveyed for lifeotypes and related information. In an embodiment, an employer may monitor employees, such as by outfitting each employee with a wearable sensor device, to determine when employees are stressed, and when a breakdown is likely to occur, based on lifeotypes and related data. In another embodiment, the military may use lifeotype information to assess and monitor morale and identify potential problems and issues. In embodiment, lifeotype information may be used to assist with monitoring a worker by providing a wearable body monitor, the wearable body monitor including a plurality of sensors and a facility for inferring the nature of the activity of the worker from the outputs of the sensors; and providing a report generating facility for reporting the activities of the worker over a period of time. Lifeotypes and related information may also be applied in security-related applications. Lifeotypes may be used to monitor prisoners, such as to predict a prison uprising. Lifeotypes may also be used to interpret the stress levels of border guards and security guards to predict potential security breaches. Lifeotypes and the Platform may be used for anti-terrorism applications. In another embodiment, the anxiety level of a truck driver, boxer and others may be monitored.

Lifeotypes and the Platform may be used for marketing and advertising. Marketing and advertising may be targeted based on lifeotypes and related information. Lifeotypes and related information can be combined with location and contextual data to further customize an advertisement. A marketer or advertiser may determine if a product works or is likely to work for a target person or group based on lifeotypes and related data. Using the Platform and/or sensors or body monitors, a user can verify receipt of an advertisement or marketing message and also determine the target person or group's response to the advertisement or message. In an embodiment, the Platform may permit a marketer to determine if the target person laughed at the advertisement. Lifeotypes and related information may be self-reinforcing and may realize network effects. The more lifeotypes and related data that are generated the more valuable the Platform and the information becomes. Once there is a base of data for comparison and the like, more people will want to use the Platform, systems and methods to take advantage of the data.

The Platform and lifeotype information may be used for recruiting purposes. The Platform and lifeotype information may be used for human resources related applications. In an embodiment, lifeotypes and related data may be used as part of the interview process, for recruiting, determining compensation, workforce management, performance evaluation, retirement planning, determining benefits, planning for succession and the like. The Platform and lifeotypes may also be used in connection with recruiting for the military, law enforcement, fire fighting, paramedics, first responders and the like. The Platform and lifeotypes may also be used to assess morale and for profiling and advancement. Lifeotypes and related information may be used to determine eligibility for certain ranks and missions. In an embodiment, the special forces may have certain lifeotype-related entrance criteria. The Platform and lifeotypes may also be used in sports recruiting. In embodiments, the Platform and lifeotypes may also be used to locate and/or draft athletes.

Lifeotypes and related information may be purchased and sold. An individual may want to know his lifeotype or learn of changes in his lifeotype, and he may purchase this information. Individuals may also sell their lifeotype information, such as to other individuals, third parties, data warehouses and the like. Lifeotypes may be sold with comparative or interpretive information regarding lifeotypes in general or specific lifeotypes. Lifeotypes may be sold with user manuals or other content regarding one or more lifeotypes. Analytics and consulting may be provided in connection with lifeotypes. In embodiments, analytics and consulting services may be provided in connection with identification and analysis of lifeotypes. Lifeotypes and related information may also be used in connection with content presentation and censoring. In an embodiment, a less intense version of a movie or a movie with an altered ending may be presented based on the lifeotype of the viewer. Reviews of content, products, services and the like may also be presented based on lifeotypes. Lifeotypes and related information may be used to sort, filter and present reviews. In an embodiment, an average rating of a particular fitness product may be presented to a user, but the rating may consist of an average of only those ratings from individuals with the same lifeotype as the user.

The Platform may be integrated with other systems that handle data. The other systems may include medical systems, healthcare systems, entertainment systems, security systems, alarm systems, financial systems, transactional systems, automobile systems, home networks, home theatre systems, wireless networks, workplace information technology systems, airport systems, airline systems, transportation environment systems, systems in recreational environments, such as sports arenas, concert halls and theatres, and the like. Lifeotype data and related data may be sold to data businesses. Lifeotype data and related data may be used for data analysis, data mining, data warehousing and the like. In embodiments, a user may purchase a seat for use of the database. In embodiments, a user may purchase analysis and services in connection with the data. In embodiments, users may purchase tailored datasets for studies. Users may include researches, governments, health care organizations, such as the World Health Organization, National Institutes of Health, the Center for Disease Control and the like, academics, industry, private sector participants, commercial users, individuals and the like.

The Platform may include an artificial intelligence engine. The artificial intelligence engine may utilize data or make use of experiences based on lifeotype data, such as by indexing information based on lifeotype. The Platform may generate reports, indexes, predictions and the like. The Platform may generate Dunn and Bradstreet type reports based on lifeotypes. The Dunn and Bradstreet type reports may relate to a company, users of a particular product, fans of a particular show, fans of a particular sports team, audience and the like. The Platform may allow for the identification of related persons based on lifeotypes. Family trees may be built based on lifeotype information. Lifeotypes may evolve overtime and across generations. The Platform may be used to study the evolution of lifeotypes. The evolution of lifeotypes may be studied in relation to genetic evolution information. Lifeotypes and related information may also be used in crime scene investigation and forensics. Lifeotype information may also be registered with a registry. In an embodiment, lifeotype information for criminals in a certain area may be registered with a lifeotype registry maintained by law enforcement.

Lifeotypes and related information may form part of a royalty system. In an embodiment, a user may receive a payment if he or she chose to opt-in to a lifeotype information sharing program. A person may receive a royalty each time his lifeotype data is accessed. A person may receive a royalty each time his lifeotype data is used in a study. A user may participate in the royalty system on an anonymous basis. A user may choose to opt-in or opt-out of an information sharing program. The system may provide incentives for a user to opt-in.

Advertising may be targeted based on lifeotype. Bidding for ad placement may be based on lifeotype. Lifeotype may be used as another demographic, psychographic or the like. Lifeotypes may be used as a way to personalize ads. Lifeotypes and related information may be used for the timing, placement and targeting of ads. In an embodiment, an advertisement for an analgesic may be shown on a cell phone as a person is experiencing back ache. In another embodiment, the Platform may identify a person as experiencing arousal, then anger and then depression, and delivery a Viagra advertisement to that person. A loyalty or rewards program may be based on lifeotypes. The prizes for which points may be redeemed may be based on lifeotypes. Different lifeotypes may receive different amounts of points as a reward for a purchase, action or the like. A sales pitch may be targeted based on lifeotypes and related information. The lifeotype profiles of customer set may be analyzed. Return on investment may be tied to lifeotype. A product may be designed based on lifeotypes. In an embodiment, multiple versions of a product may be created based on lifeotype and versions for the three most common lifeotypes may be produced.

Lifeotypes and related information may be used for therapy related applications. Lifeotypes and related information may be used to target therapy. Therapies may be tailored by lifeotype. The effects of therapies may be assessed based on lifeotypes. The Platform may determine the efficacy of a therapy based on lifeotypes and related information. Recommendations and reviews may be based on lifeotypes and related information. Lifeotypes and related information may be used in connection with the provision of advice. The delivery of advice may be tailored based on lifeotypes. In an embodiment, an open-minded person may receive advice with more recommendations than someone with a more stubborn lifeotype. The content of the advice may be tailored or filtered based on lifeotype information. Marriage advice may be provided based on lifeotypes and related information. Statistics of martial success may be calculated based on lifeotypes and related information. The compatibility of spouses may be reviewed based on lifeotype information. Career advice may be provided based on lifeotypes and related information. Recruiting and job seeking advice may be based on lifeotypes and related information.

Lifeotypes and related information may be used for generating predictions and coaching. In embodiments, a prediction may be of the status of a particular trait five years in the future and the prediction may be based on lifeotypes. In embodiments, the coaching may be in connection with a goal and/or an activity, such as a sport, hobby, for academics and the like. Lifeotypes and related information may be used for comparisons. In an embodiment, the current status of a user may be compared to the status of the user at some time in the past. The Platform may analyze what a user was doing when he performed well in the past and may make suggestions to return the user to his past performance state or to improve on that state. The Platform may also determine what level or status is typical for a user and may inform a user when he is back to normal. In an embodiment, the Platform may determine whether a user has returned to his normal state following an injury and rehabilitation. The Platform may enable comparisons to individuals who have achieved a particular goal. In an embodiment, a basketball player may be compared to Michael Jordan, in terms of lifeotype. The Platform may generate a coaching strategy based on differences in lifeotypes. The Platform may calculate the probability that the basketball player will reach his goal, which may be playing as well as Michael Jordan. The Platform may provide feedback or behavior modification and may include a coaching engine. In an embodiment, coaching may be informed by one or more guidance algorithms. A guidance algorithm may consider derived and/or sensed data, a condition in connection with derived and/or sensed data, an environmental factor in connection with derived and/or sensed data and the like. In an embodiment, coaching may include guidance in relation to diagnostic goals, prescriptive goals, alerts, reports, predictions and the like. In embodiment, the coaching engine and/or the Platform may learn via learning algorithms considering data regarding an individual, a population, genetics, evolution, neural nets and the like.

The Platform and lifeotypes and related information may be utilized for financial applications. In an embodiment, lifeotypes and related information may be used to assess principals and key economic people in a company. The Platform may aggregate lifeotype profiles across populations for analysis. The Platform may identify target markets, business prospects and the like based on lifeotype. The Platform and lifeotypes and related information may be utilized for e-commerce applications. In embodiments, life bits may be obtained from e-commerce transactions. In embodiments, lifeotypes may be used in connection with e-commerce advertising, such as for targeted advertising and product placement. In embodiments, auctions or reverse auctions may be cataloged based on lifeotypes. Portals may also be based on lifeotypes and related information. In an embodiment, a portal may be tailored to a particular lifeotype or group of lifeotypes.

The Platform and lifeotypes and related information may be utilized for concierge services. In an embodiment, the concierge service may be an "On Star" service based on lifeotypes and related information. In embodiments, the concierge service interface may be wearable with service based on lifeotypes. In an embodiment, the concierge service may function as an assistant, guardian angel, protector and the like. Lifeotypes and related information may be included in a registry of lifeotype services. Voting and politics may be informed by lifeotypes and related information. Candidates may be assessed based on lifeotypes and related information. In an embodiment, a person of a particular lifeotype, such as a very active, outdoor oriented lifeotype, may be well served by voting for a candidate with a similar lifeotype as that person may be more in tune with environmental issues that matter to the person. Recommendations of which candidate to vote for may be generated based on lifeotypes and related information. The Platform may enable automatic exclusions and/or incentives structures based on lifeotypes. In an embodiment, a user may not be able to drink, drive, eat in a particular location and the like based on lifeotype. In an embodiment, a user may be provided with an incentive to eat at a particular location, such as a health food restaurant. Tax breaks may also be provided based on lifeotypes, such as to encourage good, healthy, lawful and other behavior.

The Platform may include one or more user interfaces. The Platform may include a user interface for input of data and selection of parameters and attributes. The Platform may include a user interface for viewing data, processing data, viewing results and the like. The Platform may include a user interface for mapping. Lifeotype information may be superimposed on or presented using a map, such as Google Maps. In an embodiment, derived data may be placed on a map so that geographic clusters with similar characteristics or groups of individuals with similar lifeotypes may be located. The mapping may include an indication of demographic and socioeconomic data. The mapping interface enables visualization of lifeotype data, identification of trends and the combination of biology, motion and location.

The user interface may enable visualization of data and/or results. The visualization may be two-dimensional, three-dimensional, four-dimensional and/or multi-dimensional, including interactive-type spaces, methods, devices, and systems disclosed in Stivoric et al., pending U.S. patent application Ser. No. 11/582,896 for Devices and Systems for Contextual and Physiological-Based Detection, Monitoring, Reporting, Entertainment, and Control of Other Devices, each of which is incorporated, in its entirety, herein by reference. The user interface may enable presentation of spatial representations of lifeotypes. The user interface may enable presentation of a web of inter-related lifeotypes. The user interface may enable presentation of a lifeotype along with other data concerning the lifeotype. In an embodiment, the user interface may display continuous physiological data relating to users who have elected to opt-in to a data sharing program. The continuous physiological data may be shared anonymously or openly. Parts of the continuous physiological data may be selectable. The continuous physiological data may be queried through the user interface. The queries may be freeform, directed or suggested, including near relationship suggestions or hints. The query results may be weighted by their pertinences, popularity, likelihood of success or strength in correlation.

Figure 18:
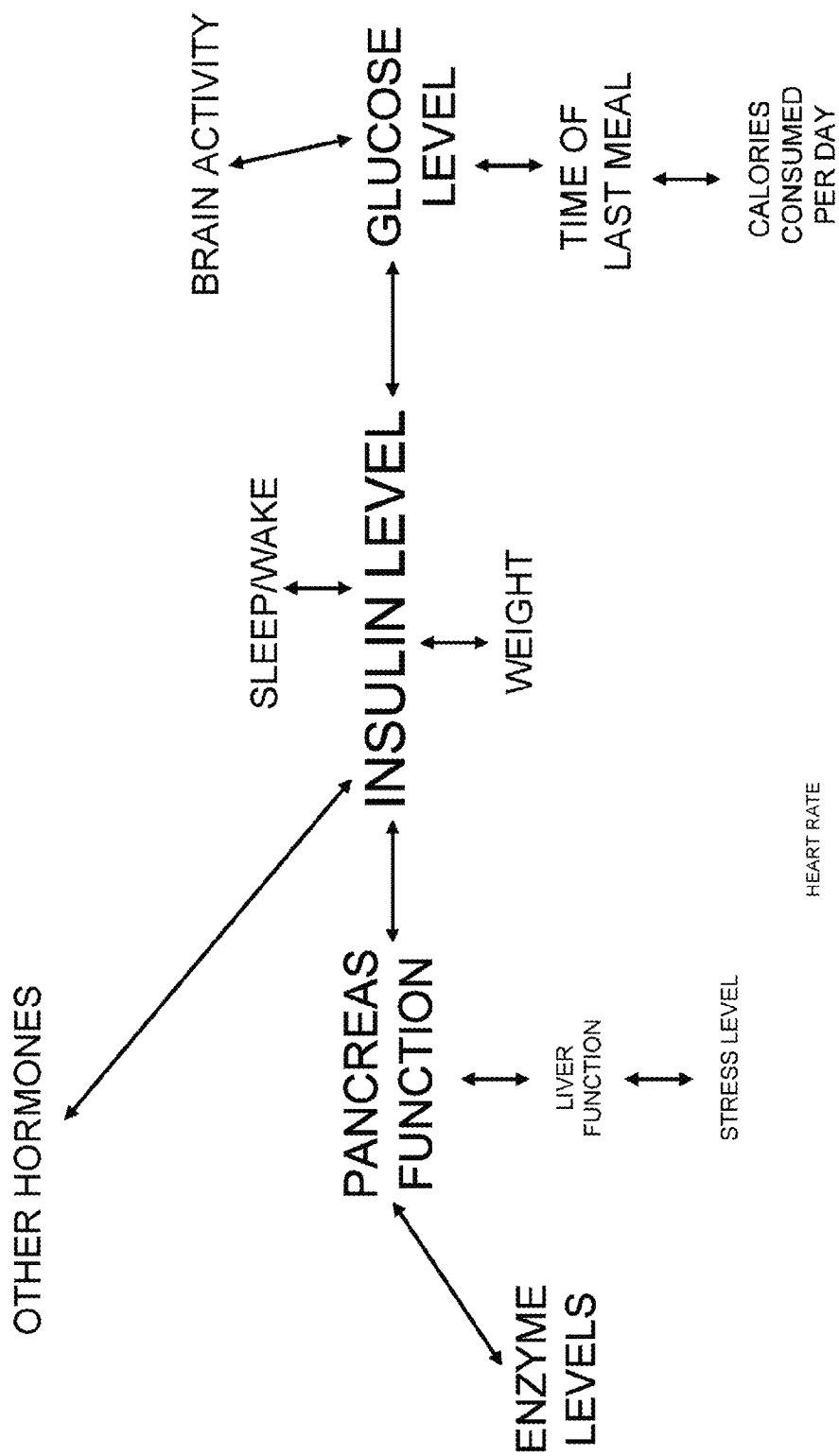
Figure 19A:
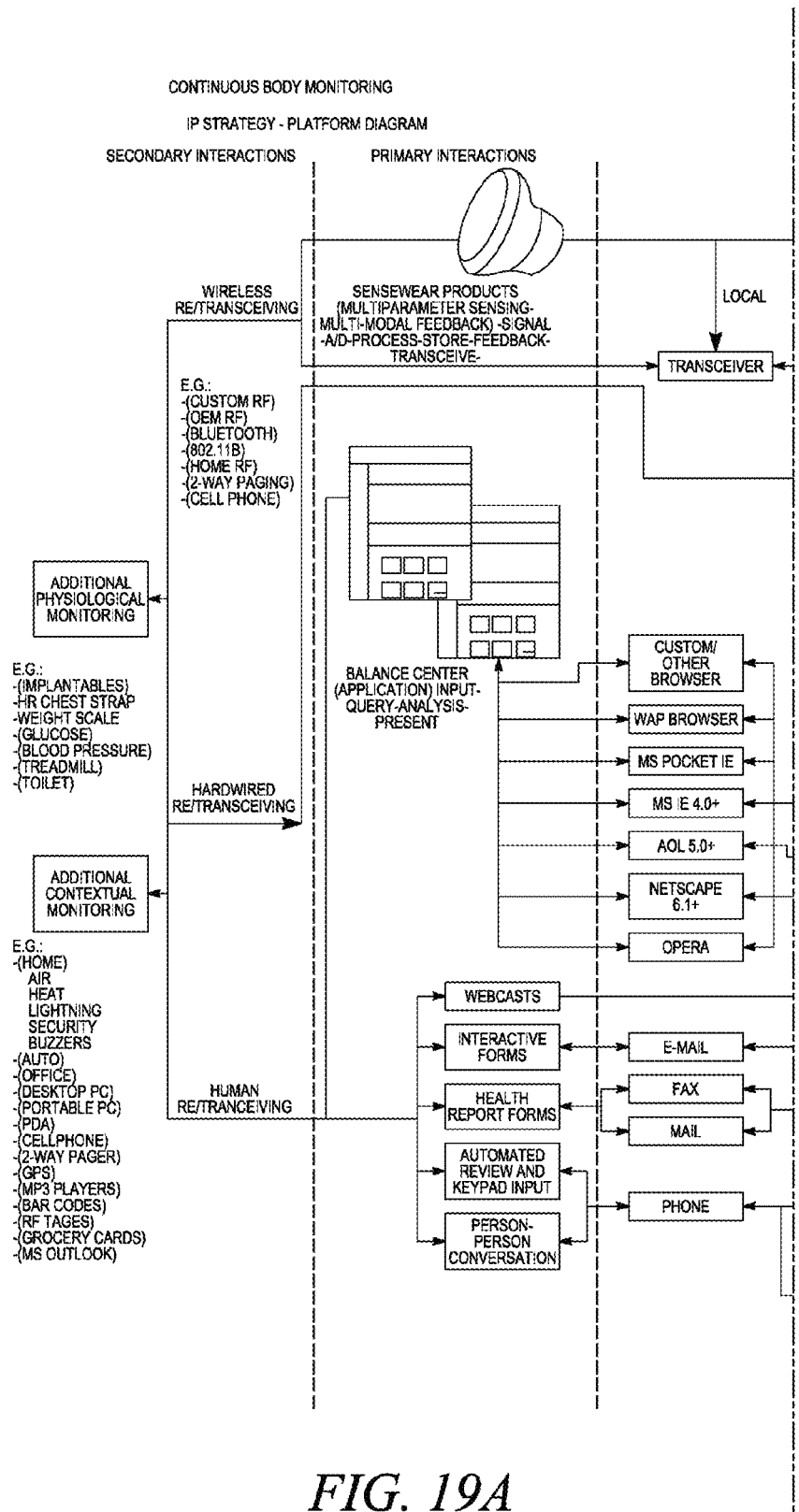
FIGS. 19A, 19B and 19C depict an embodiment of the architecture of the Platform.
Figure 19B:
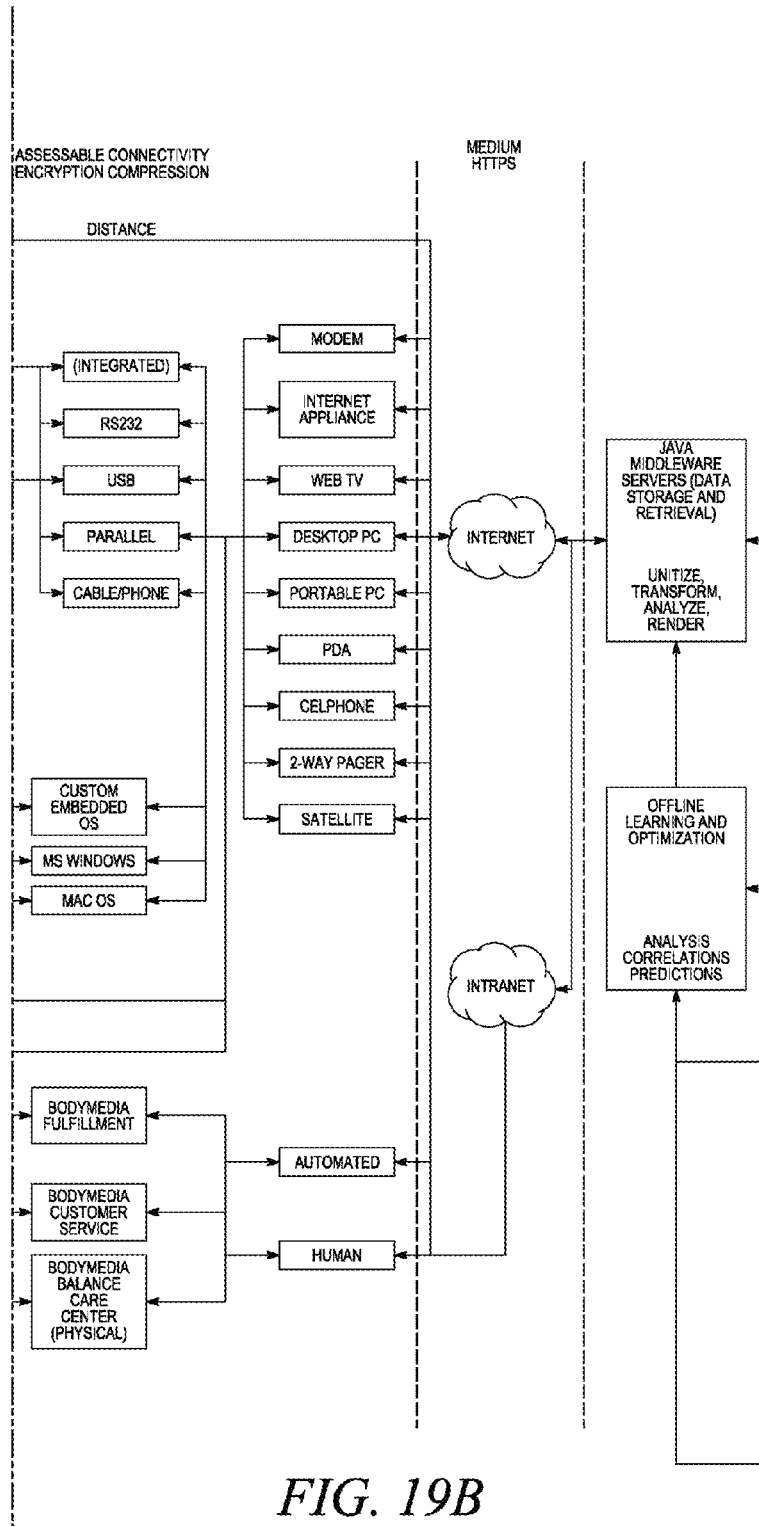
Figure 19C:
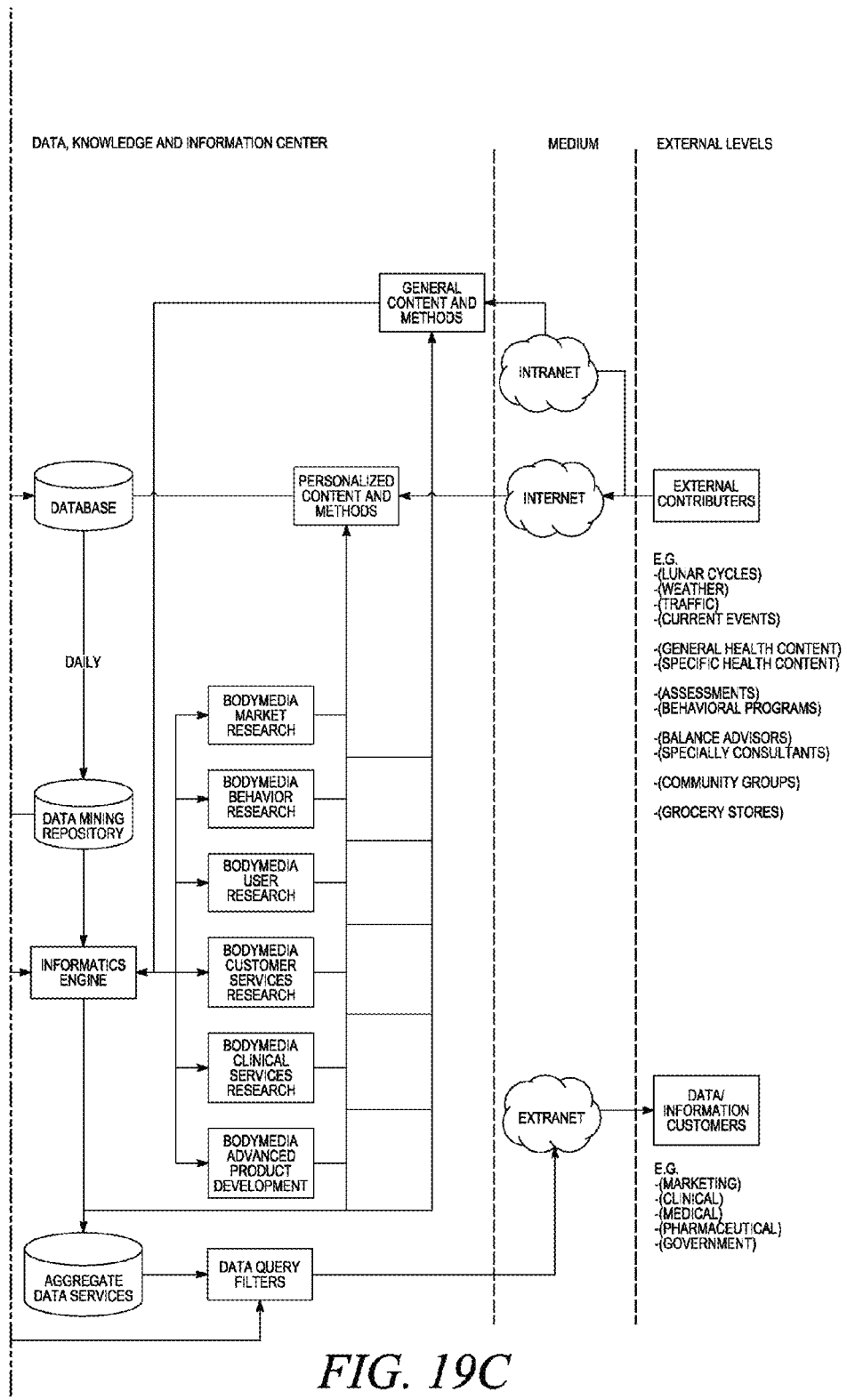

The user interface may present lifeotypes and related information using one or more spider map or the like. Referring to FIG. 18, a spider map or the like may depict life bits, life bytes, lifeotypes and related information, along with relationships among the depicted items. The spider map or the like may depict degrees of relevance and inter-relatedness in terms of color, size (as in FIG. 18), depth, distance (such as the distance between items and the degrees of separation of items) and the like. For a particular item, directly related items may be linked to the item with a line, and other items with more degrees of separation may appear smaller, in a darker color, greyed out or the like. As a new item of interest is selected, the spider map or the like may re-center on that new item of interest. The user interface may allow filters and search parameters to be applied to a spider map or the like.

The user interface may also be used to highlight and explore certain facts, such as facts that are already known to the user. A user may use the Platform and/or interface to create a visualization of a fact already known to the user. The visualization may help the user to understand the fact and explore the relationship of that fact with other items of data.

In an embodiment, the Platform may determine a particular lifeotype for a particular user. A user may review the results in the context of a population in the user's area or in another area, such as by superimposing the results on a Google Earth type application. The user may be able to identify clusters of people in the world with similar lifeotypes. For example, the user may determine that a cluster of people with his lifeotype live in Pittsburgh and another cluster live in Oslo. The user interface may allow the user to superimpose other information which may enable the user to identify other trends. For example, the interface may allow the user to superimpose weather data, and the user may determine that Pittsburgh and Oslo have similar sunlight and precipitation patterns. The Platform may also suggest other relevant or explanatory information. In an embodiment, the Platform may determine that economic bracket is relevant and may display socioeconomic data on the map in the background. The interface may allow for identification of clusters of people with similar lifeotypes and related data, such as sleeping six hours, similar body mass index and similar economic brackets. The interface may also present near relationships, such as in the form of a spider map or the like. Certain sections of the map may be greyed out or appear in the background. The interface may also suggest other related queries or bring other relevant information to the attention of the user. The interface may allow a user to compare lifeotypes and related information relevant to him or a person or group of interest to norms, others individuals or groups, to the person or subject himself or itself at another point in time, to subsets, to subsets at other points in time. The interface may also allow for the addition of constraints, restrictions, filters and the like, which may be implicit, hidden or explicit.

The Platform may be implemented or provided using various architectures, systems and methods. FIGS. 19A through 23B depict several possible embodiments of the Platform.

The Platform may include or be implemented using a server and/or server farm. The server may be a rackmount, tower, blade, desktop, portable, handheld and/or wearable server. The server may be a uni-processor or multi-processor server. The server may form a part of a monolithic computer, cluster computer, distributed computer, super computer, shared computing environment or the like. The server may be a Java, .NET or the like middleware server, such as for data storage and retrieval. The server may be characterized by offline learning and optimization, such as through analysis, correlation, prediction and the like.

The Platform may be composed of or contain various applications. An application may be compiled or interpreted. An application may be a standalone application, an embedded application, a stored procedure (such as in a database), a library (which may be static or shared) and the like. An application may be a server-side application or a client-side application, such as Ajax. An application may be a mashup, a widget or the like. The Platform may be implemented using a service-oriented architecture. At least one component, facility or layer of the Platform may be accessible as a service, such as a web service, and may be accessible from anywhere in the world. The service oriented architecture may be implemented using REST, RPC, DCOM, CORBA, Web Services, WSDL, BPEL, WS-CDL, WS-Coordination and the like.

The Platform may be implemented in a way compatible with or using a Web 2.0 environment. The Platform may be implemented as a Web 2.0 application. The Platform may include Web 2.0 applications. The Platform may enable Web 2.0 applications that emphasize online collaboration and sharing among users. The Platform may be implemented using a network, such as any of the networks described herein. The Platform may be local, shared or a combination of the two. The Platform may be implemented using a local network, a broad network or a combination of the two. The Platform may be local or fully distributed.

The Platform may be implemented using a three-tier (or n-tier) architecture. The architecture may include an application server, which may be a J2EE server (such as Tomcat, JOnAS, Servlet, JSP and the like) or may utilize CGI, mod_perl, ASP, .NET and the like. The architecture may include a database server. The database may be a relational database, object database, stream database, flat database, network database, hierarchical database or the like. The Platform may include a database or database facility wherein data units are constructed to represent time based representation of a plurality of derived parameters, such as derived vital signs and the like. The data may be obtained from a body monitor, via data integration or the like. The data may be obtained by a feed or pulled from sources. The data may be obtained by push and/or pull means. The database may be a distributed database, federated database, online database, parallel database, real time database, spatial database, statistical database, time series database or the like. The network associated with the database may be one or more of the following network types: DAS, SAN, NAS, HSM, ILM, SAT, FAN and the like. The architecture may include a transaction processing management system.

Figure 21:
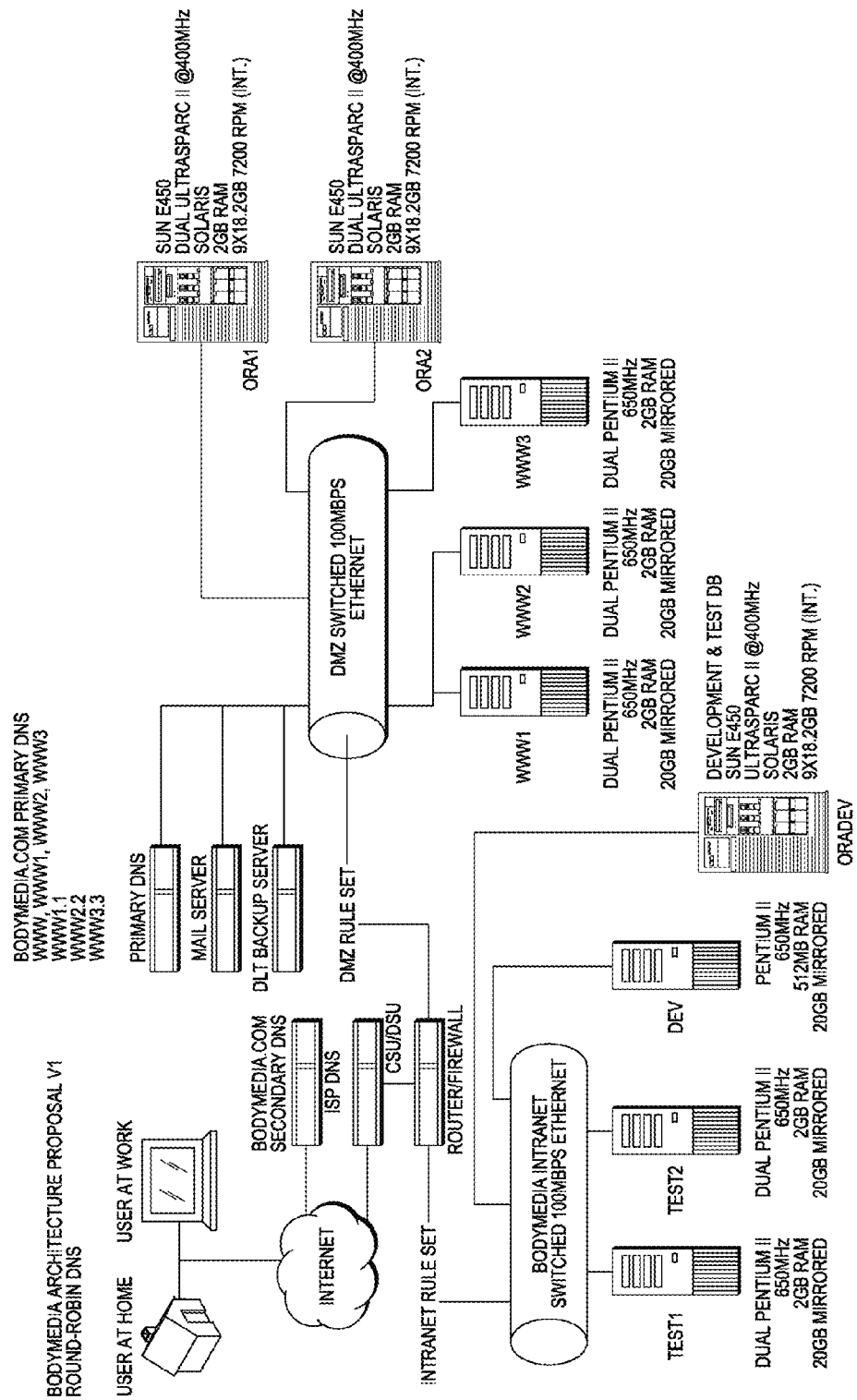
FIG. 21 depicts an embodiment of the architecture of the Platform using round-robin DNS load balancing.
Figure 22:
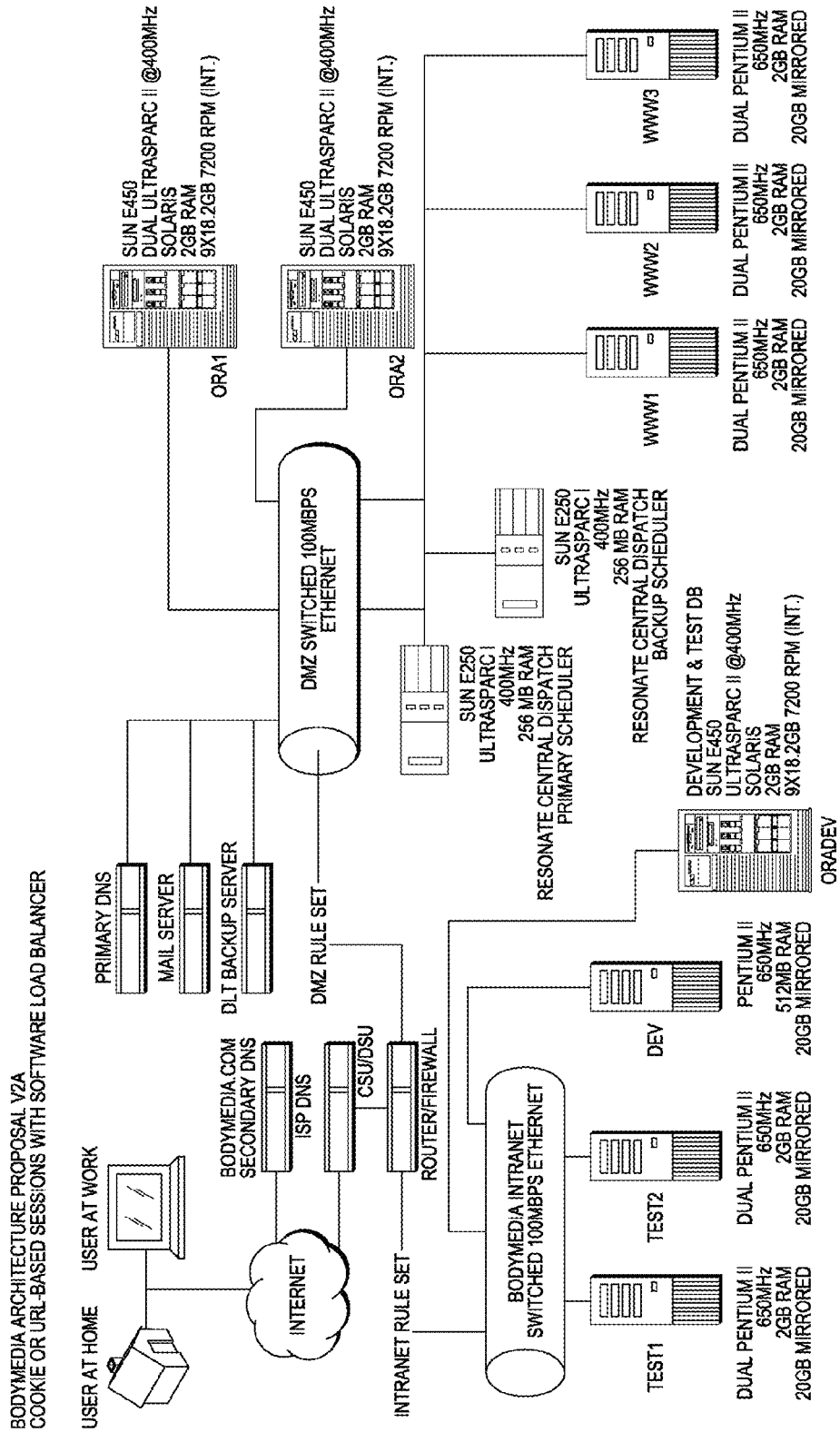
FIG. 22 depicts an embodiment of the architecture of the Platform using cookie or URL-based sessions with a software load balancer.
Figure 23A:
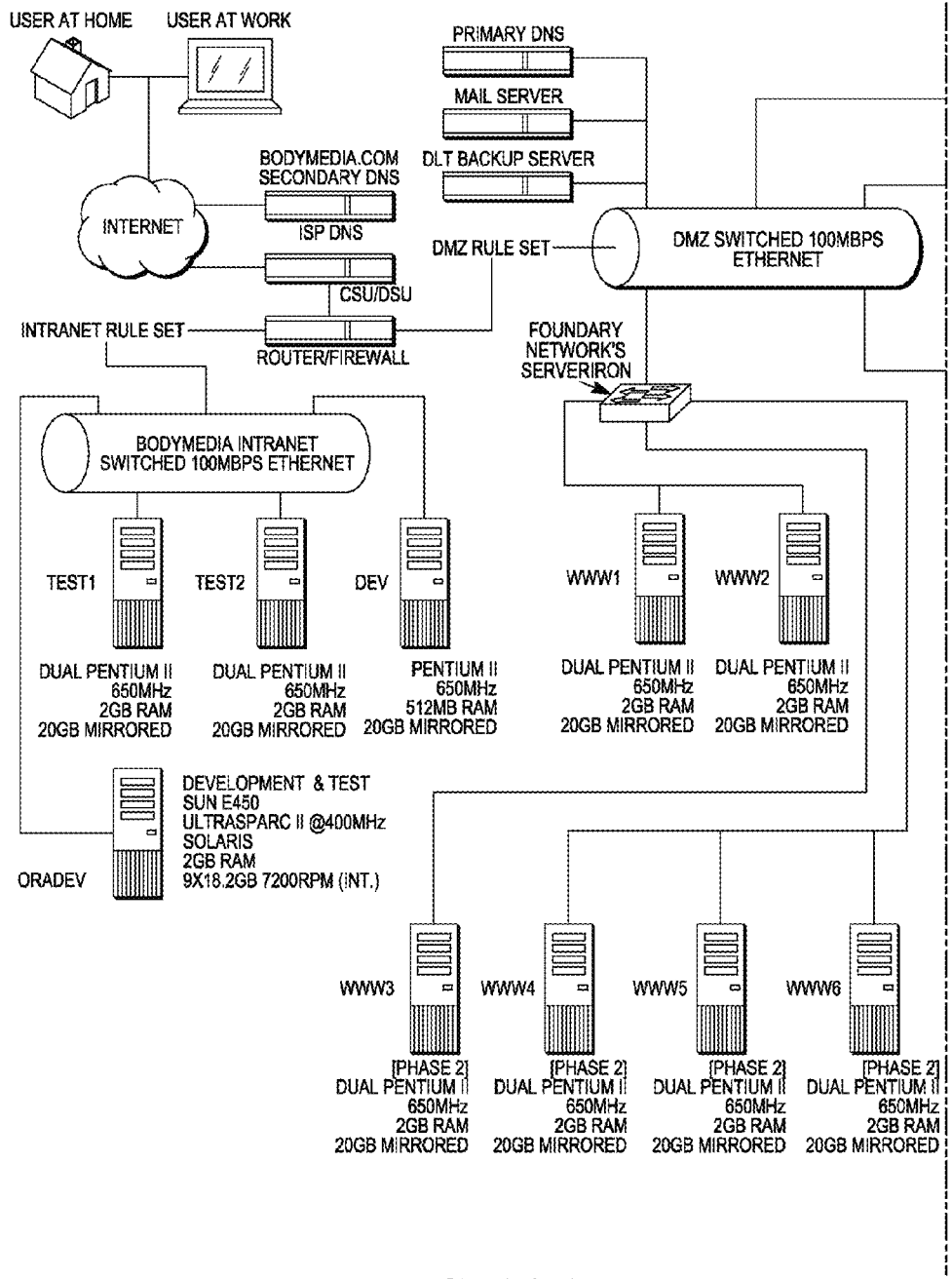
FIGS. 23A and 23B depict an embodiment of the architecture of the Platform using cookie-based sessions with a hardware load balancer.
Figure 23B:
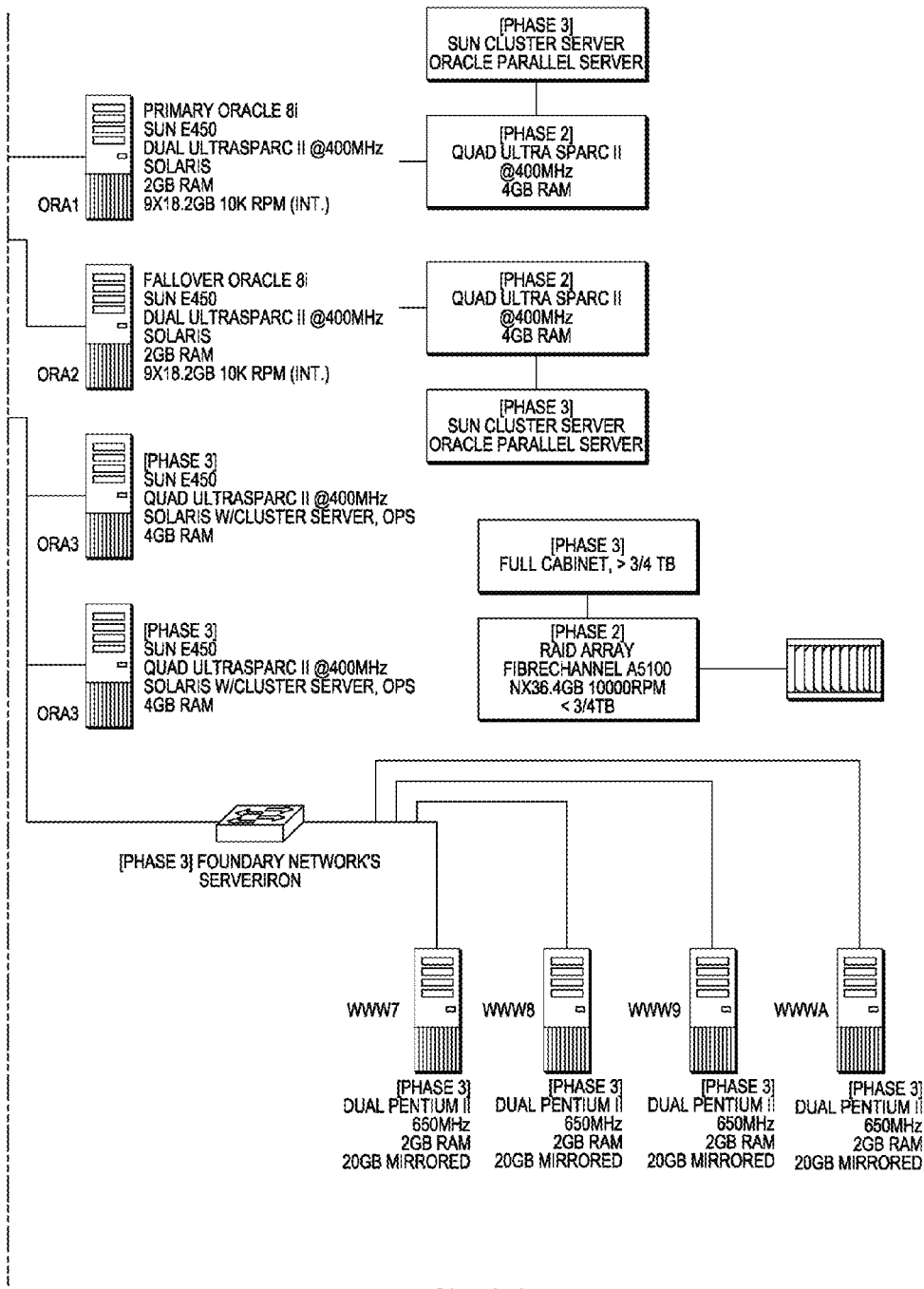

The architecture may include a web server, such as Apache, IIS and the like. The architecture may include one or more client-side applications. A client-side application may be a standalone application, widget, plug-in, in-browser script (such as Javascript) and the like. The architecture may include a firewall. The firewall may be based on, or include functionality for, port forwarding, SPI, NAT, dynamic DNS, IP tunnel, VPN, DMZ and the like. The architecture may include a load balancer. Referring to FIG. 21, the architecture may be a round-robin DNS. Referring to FIG. 22, the architecture may be a cookie or URL-based session with software load balancer. Referring to FIGS. 23A-23B, the architecture may be based on cookie-based sessions with a hardware load balancer. The architecture may include a switch, router, hub or the like, which may be based on VLAN, LAN or the like.

Figure 20:
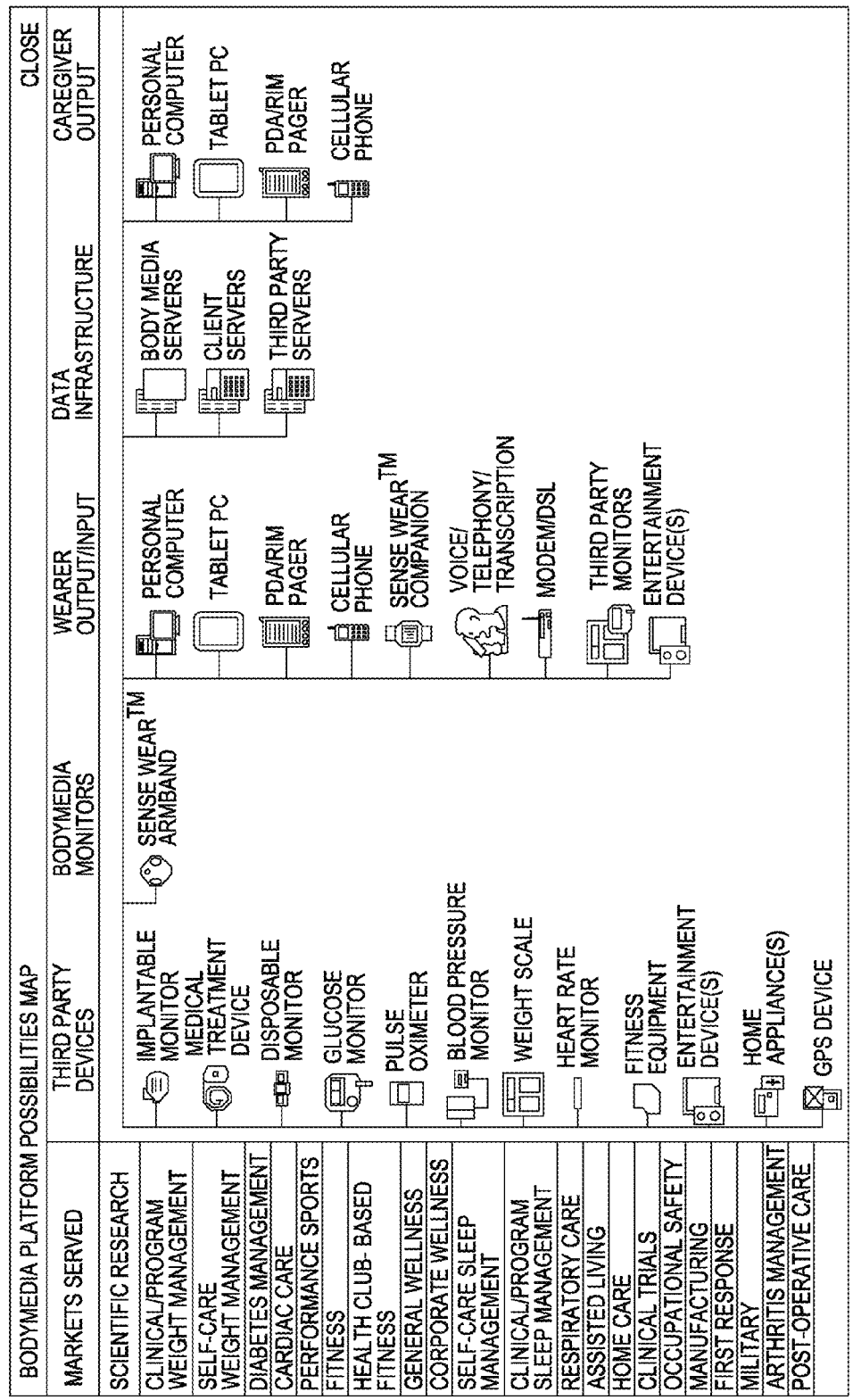
FIG. 20 depicts an embodiment of the architecture of the Platform.

The Platform may include a data mining repository, data warehouse or the like. The Platform may include or make use of capabilities for extraction, transformation and loading of data. Referring to FIG. 6, the Platform may include interfaces to other systems, applications and services. An interface may be provided through an internet, extranet or the like, such as by using CSU, DSU or the like. An interface may be provided in a wired manner, such as through an Ethernet or the like, or in a wireless manner, such as through IrDA, free-space optical communication, cellular, IEEE 802 or the like. An interface may be provided through a personal area network, local area network, metropolitan area network, wide area network and the like. Referring to FIG. 20, interfaces may be provided to various systems and devices, such as implantable monitors, medical treatment devices, disposable monitors, glucose monitors, pulse oximeters, blood pressure monitors, weight scales, heart rate monitors, fitness equipment, entertainment devices, home appliances, GPS devices, SenseWear armbands, personal computer tablet PCs, PDAs, pagers, wireless email devices, Blackberries, Treos, smart phones, cellular phones, SenseWear companions, voice systems, telephony systems, VoIP systems, transcription systems, modems, high speed internet access systems, third party monitors, internal servers, client servers, third party servers and the like.

The Platform may include data administration functionality. Referring to FIG. 6, the Platform may include security, logging, conditional access and authentication functionality. The architecture may include security functionality, such as conditional access, authentication, intrusion detection and prevention and the like. The architecture may include logging functionality. The architecture may include backup and recovery functionality. The backup and recovery functionality may be enabled using magnetic table, hard disk, optical disc, solid state storage and the like. The backup and recovery functionality may be implemented on-line, off-line or a combination of the two. The backup and recovery functionality may be provided offsite, remotely, onsite or in a combination. The architecture may include means for redundancy and failover. Certain information or aspects of the Platform may be restricted to local use, while others may be fully shared.

The Platform may include data facilities. Data may be any of the data described herein. Data may come from any of the sources described herein. Data may be housed in databases, datamarts, data warehouses and the like. The data may be directly supplied, such as directly downloaded, may flow through the internet, may be distributed and the like. Interfaces to data and data sources may include ODBC, JDBC and the like.

The Platform may include a central monitoring unit. The Platform may utilize a central monitoring unit, or the central monitoring unit may implement all or a portion of the Platform. The architecture of the platform may enable data processing.

The elements depicted in flow charts and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these, and all such implementations are within the scope of the present disclosure. Thus, while the foregoing drawings and description set forth functional aspects of the disclosed systems, no particular arrangement of software for implementing these functional aspects should be inferred from these descriptions unless explicitly stated or otherwise clear from the context.

Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated, or otherwise clear from the context.

The methods or processes described above, and steps thereof, may be realized in hardware, software, or any combination of these suitable for a particular application. The hardware may include a general-purpose computer and/or dedicated computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

The invention claimed is:

1. A computer-system-implemented method of predicting the mental state for an individual based on the individual's traits, the computer system having at least one programmed processor to implement the method, the method comprising:

continuously collecting data components of an individual from a wearable sensor device;

collecting another set of data components of the individual from a source separate from the wearable device;

accessing a database by said computer system comprising data structures of other individuals, wherein said data structures of other individuals are related to known human traits;

the computer system—

(i) assembling a data structure for the individual that includes at least one component from the collected data components from the wearable sensor device and at least one of said another set of data components;

(ii) accessing said database to determine a similarity of the data structure for the individual with data structures of other individuals;

(iii) based on the determination, assigning a human trait to the individual; and (iv) based on the trait of the individual using an engine to consider derived and sensed data from the wearable sensor device to predict the mental state of the individual based on the assigned trait.

2. The method of claim 1, wherein the mental state is a healthy state.

3. The method of claim 1, wherein the mental state is an unhealthy state.

4. The method of claim 3, wherein the mental state is a disease state.

5. The method of claim 1, wherein the mental state is a mood of the individual.

6. The method of claim 1, wherein said another set of data components is selected from the group consisting of: derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data.

7. The method of claim 1, wherein said set of data components from a wearable sensor device is selected from the group consisting of: derived data, analytical status data, contextual data, continuous data, discrete data, time series data, event data, raw data, processed data, metadata, third party data, physiological state data, psychological state data, survey data, medical data, genetic data, environmental data, transactional data, economic data, socioeconomic data, demographic data, psychographic data, sensed data, continuously monitored data, manually entered data, inputted data, continuous data and real-time data.

8. The method of claim 1, wherein at least one data component collected from a wearable sensor device is a data component that is derived from a plurality of sensors that is distinct from the output of any single sensor.

9. The method of claim 1, wherein the assembled data structure that includes at least one component from the collected data components from the wearable sensor device includes at least one data component collected from a wearable sensor device is a data component that is derived from a plurality of sensors that is distinct from the output of any single sensor.

* * * * *